US011471401B2

(12) United States Patent
Garibyan et al.

(10) Patent No.: US 11,471,401 B2
(45) Date of Patent: Oct. 18, 2022

(54) INJECTABLE SLURRIES AND METHODS OF MANUFACTURING THE SAME

(71) Applicant: The General Hospital Corporation, Boston, MA (US)

(72) Inventors: Lilit Garibyan, Newton, MA (US); William A. Farinelli, Boston, MA (US); Richard Rox Anderson, Boston, MA (US); Emilia Javorsky, Watertown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/535,493

(22) Filed: Nov. 24, 2021

(65) Prior Publication Data

US 2022/0079874 A1 Mar. 17, 2022

Related U.S. Application Data

(63) Continuation of application No. 16/288,073, filed on Feb. 27, 2019, which is a continuation-in-part of application No. 15/505,042, filed as application No. PCT/US2015/047301 on Aug. 27, 2015, now abandoned, application No. 17/535,493, filed on Nov. 24, 2021, which is a continuation of application No. 17/188,359, filed on Mar. 1, 2021, which is a continuation of application No. 15/505,042, filed as application No. PCT/US2015/047301 on Aug. 27, 2015, now abandoned, application No. 17/535,493, filed on Nov. 24, 2021, which is a continuation of application No. 17/236,567, filed on Apr. 21, 2021, which is a continuation of application No. 15/505,039, filed as application No. PCT/US2015/047292 on Aug. 27, 2015, now abandoned.

(60) Provisional application No. 62/121,472, filed on Feb. 26, 2015, provisional application No. 62/121,329, filed on Feb. 26, 2015, provisional application No. 62/042,979, filed on Aug. 28, 2014.

(51) Int. Cl.
*A61K 9/00* (2006.01)
*A61K 33/00* (2006.01)
*A61K 47/10* (2017.01)
*A61P 9/00* (2006.01)

(52) U.S. Cl.
CPC ............ *A61K 9/0019* (2013.01); *A61K 33/00* (2013.01); *A61K 47/10* (2013.01); *A61P 9/00* (2018.01)

(58) Field of Classification Search
CPC .......... A61K 9/0019; A61K 33/00; A61P 9/00
See application file for complete search history.

(56) References Cited

U.S. PATENT DOCUMENTS

| | | | |
|---|---|---|---|
| 4,883,665 A | 11/1989 | Miyazima et al. | |
| 4,986,079 A | 1/1991 | Koseki et al. | |
| 5,005,364 A | 4/1991 | Nelson | |
| 5,143,063 A | 9/1992 | Fellner | |
| 5,507,790 A | 4/1996 | Weiss | |
| 5,769,879 A | 6/1998 | Richards et al. | |
| 6,126,684 A | 10/2000 | Boyden et al. | |
| 6,244,052 B1 | 6/2001 | Kasza | |
| 6,413,444 B1 * | 7/2002 | Kasza ..................... | A61F 7/12 62/340 |
| 6,430,957 B1 | 8/2002 | Inada et al. | |
| 6,962,601 B2 | 11/2005 | Becker et al. | |
| 7,367,341 B2 | 5/2008 | Anderson et al. | |
| 7,422,601 B2 | 9/2008 | Becker et al. | |
| 7,507,234 B2 | 3/2009 | Utley et al. | |
| 7,897,141 B2 | 3/2011 | Wheatley et al. | |
| 8,505,315 B2 | 8/2013 | Kasza et al. | |
| 8,715,622 B2 | 5/2014 | Wheatley et al. | |
| 8,840,608 B2 | 9/2014 | Anderson et al. | |
| 9,980,076 B1 | 5/2018 | Avram et al. | |
| 10,582,960 B2 | 3/2020 | Avram et al. | |
| 2002/0021741 A1 * | 2/2002 | Faries, Jr. .............. | G01K 11/12 374/E11.018 |
| 2002/0107199 A1 | 8/2002 | Walker | |
| 2003/0032996 A1 | 2/2003 | Hallman | |
| 2003/0181897 A1 | 9/2003 | Thomas et al. | |
| 2004/0068309 A1 | 4/2004 | Edelman | |
| 2004/0176755 A1 | 9/2004 | Lafontaine | |
| 2004/0210212 A1 | 10/2004 | Maurice et al. | |
| 2004/0215295 A1 | 10/2004 | Littrup et al. | |

(Continued)

FOREIGN PATENT DOCUMENTS

| | | |
|---|---|---|
| CN | 204468406 U | 7/2015 |
| CN | 105640642 A | 6/2016 |
| EP | 2561886 A1 | 2/2013 |
| JP | 2003-534366 A | 11/2003 |
| JP | 06-510758 A | 3/2006 |
| JP | 2010-508130 A | 3/2010 |
| JP | 2011-516168 A | 5/2011 |
| JP | 2017-526684 A | 9/2017 |
| WO | WO 90/03795 A1 | 4/1990 |
| WO | WO 93/00930 A1 | 1/1993 |

(Continued)

OTHER PUBLICATIONS

International Search Report and Written Opinion for International Application No. PCT/US2020/043280 dated Nov. 9, 2020.

(Continued)

*Primary Examiner* — Andrew S Rosenthal
(74) *Attorney, Agent, or Firm* — Wolf, Greenfield & Sacks, P.C.

(57) ABSTRACT

A method for treating vascular diseases is provided. The method includes fabricating a sterile ice slurry including water and ice particles, cooling the sterile ice slurry to a predetermined temperature, and injecting the sterile ice slurry into a desired tissue region. The desired tissue region includes perivascular adipose tissue.

30 Claims, 48 Drawing Sheets

(56) References Cited

U.S. PATENT DOCUMENTS

| | | | |
|---|---|---|---|
| 2005/0123666 A1* | 6/2005 | Vaghela | A23G 9/44 426/565 |
| 2005/0203598 A1 | 9/2005 | Becker et al. | |
| 2005/0251120 A1 | 11/2005 | Anderson et al. | |
| 2006/0079869 A1 | 4/2006 | Bischof et al. | |
| 2006/0161232 A1 | 7/2006 | Kasza et al. | |
| 2006/0235375 A1 | 10/2006 | Littrup et al. | |
| 2007/0010861 A1 | 1/2007 | Anderson et al. | |
| 2007/0056313 A1 | 3/2007 | Kasza et al. | |
| 2007/0106247 A1 | 5/2007 | Burnett et al. | |
| 2008/0183164 A1 | 7/2008 | Elkins et al. | |
| 2008/0236186 A1 | 10/2008 | Kasza et al. | |
| 2008/0247957 A1 | 10/2008 | Wheatley | |
| 2008/0279783 A1 | 11/2008 | Wheatley et al. | |
| 2008/0300571 A1 | 12/2008 | Lepivert et al. | |
| 2009/0028797 A1 | 1/2009 | Wheatley et al. | |
| 2009/0118722 A1 | 5/2009 | Ebbers et al. | |
| 2009/0234325 A1 | 9/2009 | Rozenberg et al. | |
| 2009/0255276 A1 | 10/2009 | Kasza et al. | |
| 2009/0301107 A1 | 12/2009 | Kammer et al. | |
| 2010/0036295 A1 | 2/2010 | Altshuler et al. | |
| 2010/0113615 A1 | 5/2010 | Boyden et al. | |
| 2010/0137304 A1 | 6/2010 | Gilday et al. | |
| 2010/0152880 A1 | 6/2010 | Boyden et al. | |
| 2010/0179527 A1 | 7/2010 | Watson et al. | |
| 2011/0009748 A1 | 1/2011 | Greene et al. | |
| 2012/0323232 A1 | 12/2012 | Wolf et al. | |
| 2013/0011332 A1 | 1/2013 | Boyden et al. | |
| 2013/0184695 A1 | 7/2013 | Fourkas et al. | |
| 2013/0190744 A1 | 7/2013 | Avram et al. | |
| 2013/0324989 A1 | 12/2013 | Leung et al. | |
| 2014/0200511 A1 | 7/2014 | Boyden et al. | |
| 2014/0303697 A1 | 10/2014 | Anderson et al. | |
| 2016/0151200 A1 | 6/2016 | Kammer et al. | |
| 2016/0175141 A1* | 6/2016 | Wu | A61F 7/12 607/105 |
| 2017/0274011 A1 | 9/2017 | Garibyan et al. | |
| 2017/0274078 A1 | 9/2017 | Garibyan et al. | |
| 2018/0250056 A1 | 9/2018 | Avram et al. | |
| 2019/0053939 A1 | 2/2019 | Garibyan et al. | |
| 2019/0183558 A1 | 6/2019 | Anderson et al. | |
| 2019/0192424 A1 | 6/2019 | Garibyan et al. | |
| 2021/0236639 A1 | 8/2021 | Garibyan et al. | |
| 2021/0244817 A1 | 8/2021 | Garibyan et al. | |

FOREIGN PATENT DOCUMENTS

| | | |
|---|---|---|
| WO | WO 2001/05372 A2 | 1/2001 |
| WO | WO 01/91720 A2 | 12/2001 |
| WO | WO 03/078596 A2 | 9/2003 |
| WO | WO 2008/015380 A2 | 2/2008 |
| WO | WO 2008/055243 A2 | 5/2008 |
| WO | WO 2009/009540 A1 | 1/2009 |
| WO | WO 2009/047362 A2 | 4/2009 |
| WO | WO 2009/102367 A2 | 8/2009 |
| WO | WO 2009/146053 A1 | 12/2009 |
| WO | WO 2011/100692 A1 | 8/2011 |
| WO | WO 2013/059133 A1 | 4/2013 |
| WO | WO 2015/019257 A1 | 2/2015 |
| WO | WO 2016/033380 A1 | 3/2016 |
| WO | WO 2016/033384 A1 | 3/2016 |
| WO | WO 2017/147367 A1 | 8/2017 |
| WO | Wo 2018/044825 A1 | 3/2018 |
| WO | WO 2021/151019 A1 | 7/2021 |

OTHER PUBLICATIONS

International Preliminary Report on Patentability for Application No. PCT/US2020/043280, dated Feb. 3, 2022.
International Search Report and Written Opinion for International Application No. PCT/US2015/047292 dated Dec. 7, 2015.
International Preliminary Report on Patentability dated Mar. 9, 2017 for Application No. PCT/US2015/047292.
Partial European Search Report dated Mar. 22, 2018 for Application No. EP 15836780.5.
Extended European Search Report dated Jun. 26, 2018 for Application No. EP 15836780.5.
International Search Report and Written Opinion for International Application No. PCT/US2015/047301 dated Dec. 14, 2015.
International Preliminary Report on Patentability dated Mar. 9, 2017 for Application No. PCT/US2015/047301.
Partial European Search Report dated Mar. 24, 2020, for Application No. EP 17847238.6.
Extended European Search Report dated Dec. 7, 2020 for Application No. EP 17847328.6.
International Search Report and Written Opinion dated Nov. 3, 2017 for Application No. PCT/US2017/048995.
International Preliminary Report on Patentability dated Mar. 14, 2019 for Application No. PCT/US2017/048995.
Extended European Search Report dated Aug. 26, 2019 for Application No. EP 17757262.5.
International Search Report and Written Opinion dated May 15, 2017 for Application No. PCT/US2017/019268.
International Preliminary Report on Patentability dated Sep. 7, 2018 for Application No. PCT/US2017/019268.
International Search Report and Written Opinion for International Application No. PCT/US2021/014789 dated May 18, 2021.
International Search Report and Written Opinion dated Apr. 12, 2011 for Application No. PCT/US2011/024766.
International Preliminary Report on Patentability dated Aug. 30, 2012 for Application No. PCT/US2011/024766.
[No Author Listed], Isotonic (https://biologydictionary.net/isotonic/) accessed Jun. 21, 2018, pp. 1-4 (Year: 2018).
[No Author Listed], Polysorbate-20 (https://web.archive.org/web/20130315082056/http://www.ewg.org:80/skindeep/ingredient/705137/POLYSORBATE-20/) available Mar. 15, 2013, pp. 1-3 (Year: 2013).
[No Author Listed], World Fine Chemicals Handbook. Institute of Science and Technology Information, Ministry of Chemical Industry, Ed. May 31, 1986;187-90.
Abbott et al., Front. Pharmacol. Conference Abstract: Structure and function of the blood-brain barrier. Pharmacology and Toxicology of the Blood-Brain Barrier: State of the Art, Needs for Future Research and Expected Benefits for the EU. Feb. 11-12, 2010. (doi:10.3389/conf.fphar.2010.02.00002).
Amasheh et al., Claudin-2 expression induces cation-selective channels in tight junctions of epithelial cells. J Cell Sci. Dec. 15, 2002;115(Pt 24):4969-76. doi: 10.1242/jcs.00165.
Antonijevic et al., Perineurial defect and peripheral opioid analgesia in inflammation. J Neurosci. Jan. 1995;15(1 Pt 1):165-72. doi: 10.1523/JNEUROSCI.15-01-00165.1995.
Armitage et al., Toxic and osmotic effects of glycerol on human granulocytes. Am J Physiol. Nov. 1984;247(5 Pt 1):C382-9. doi: 10.1152/ajpcell.1984.247.5.C382.
Ash, Chronic peritoneal dialysis catheters: overview of design, placement, and removal procedures. Semin Dial. Jul.-Aug. 2003;16(4):323-34.
Ballabh et al., The blood-brain barrier: an overview: structure, regulation, and clinical implications. Neurobiol Dis. Jun. 2004;16(1):1-13. doi: 10.1016/j.nbd.2003.12.016.
Barnard, The effects of extreme cold on sensory nerves. Ann R Coll Surg Engl. May 1980;62(3):180-7.
Begley, Delivery of therapeutic agents to the central nervous system: the problems and the possibilities. Pharmacol Ther. Oct. 2004;104(1):29-45. doi: 10.1016/j.pharmthera.2004.08.001.
Binshtok et al., Inhibition of nociceptors by TRPV 1-mediated entry of impermeant sodium channel blockers. Nature. Oct. 4, 2007;449(7162):607-10. doi: 10.1038/nature06191.
Blasig et al., Occludin protein family: oxidative stress and reducing conditions. Antioxid Redox Signal. Sep. 1, 2011;15(5):1195-219. doi: 10.1089/ars.2010.3542. Epub May 5, 2011.
Blasig et al., On the self-association potential of transmembrane tight junction proteins. Cell Mol Life Sci. Feb. 2006;63(4):505-14. doi: 10.1007/s00018-005-5472-x.

(56) References Cited

OTHER PUBLICATIONS

Brink et al., Abdominoplasty with direct resection of deep fat. Plast Reconstr Surg. May 2009;123(5):1597-603. doi: 10.1097/PRS.0b013e3181a07708.
Calandria, Cryoanalgesia for post-herpetic neuralgia: a new treatment. Int J Dermatol. Jun. 2011;50(6):746-50. doi: 10.1111/j.1365-4632.2010.04792.x.
Carruthers et al., Cryolipolysis and skin tightening. Dermatol Surg. Dec. 2014;40 Suppl 12:S184-9. doi: 10.1097/DSS.0000000000000229.
Colegio et al., Claudin extracellular domains determine paracellular charge selectivity and resistance but not tight junction fibril architecture. Am J Physiol Cell Physiol. Jun. 2003;284(6):C1346-54. doi: 10.1152/ajpcell.00547.2002. Epub Apr. 16, 2003.
Conaway, Ice packs in diabetic neuropathy. Phys Ther Rev. Aug. 1961;41:586-8.
Coyne et al., Role of claudin interactions in airway tight junctional permeability. Am J Physiol Lung Cell Mol Physiol. Nov. 2003;285(5):L1166-78. doi: 10.1152/ajplung.00182.2003. Epub Aug. 8, 2003.
Cukierman et al., Residues in a highly conserved claudin-1 motif are required for hepatitis C virus entry and mediate the formation of cell-cell contacts. J Virol. Jun. 2009;83(11):5477-84. doi: 10.1128/JVI.02262-08. Epub Mar. 18, 2009.
Cuschieri et al., Hypertonic preconditioning inhibits macrophage responsiveness to endotoxin. J Immunol. Feb. 1, 2002;168(3):1389-96. doi: 10.4049/jimmunol.168.3.1389.
Ding et al., Association between non-subcutaneous adiposity and calcified coronary plaque: a substudy of the Multi-Ethnic Study of Atherosclerosis. Am J Clin Nutr. Sep. 2008;88(3):645-50.
Dogan et al., Microstructural Control of Complex-Shaped Ceramics Processed by Freeze Casting. CFI Ceramic Forum International. May 2002;79(5);E35(1-4).
Dua et al., Liposome: Methods of Preparation and Applications. Int J. Pharm Stud Res. Apr. 2012; 3(2): 14-20.
Foster et al., Sympathetic but not sensory denervation stimulates white adipocyte proliferation. Am J Physiol Regul Integr Comp Physiol. Dec. 2006;291(6):R1630-7. doi: 10.1152/ajpregu.00197.2006. Epub Aug. 3, 2006.
Fox et al., Abdominal visceral and subcutaneous adipose tissue compartments: association with metabolic risk factors in the Framingham Heart Study. Circulation. Jul. 3, 2007;116(1):39-48. Epub Jun. 18, 2007.
Fried et al., Peginterferon alfa-2a plus ribavirin for chronic hepatitis C virus infection. N Engl J Med. Sep. 26, 2002;347(13):975-82. doi: 10.1056/NEJMoa020047.
Fruhstorfer et al., The effects of thermal stimulation on clinical and experimental itch. Pain. Feb. 1986;24(2):259-69.
Fujita et al., Clostridium perfringens enterotoxin binds to the second extracellular loop of claudin-3, a tight junction integral membrane protein. FEBS Lett. Jul. 7, 2000;476(3):258-61. doi: 10.1016/s0014-5793(00)01744-0.
Fujita et al., Permeability characteristics of tetragastrins across intestinal membranes using the Caco-2 monolayer system: comparison between acylation and application of protease inhibitors. Pharm Res. Sep. 1998;15(9):1387-92. doi: 10.1023/a:1011997404306.
Furuse et al., A single gene product, claudin-1 or -2, reconstitutes tight junction strands and recruits occludin in fibroblasts. J Cell Biol. Oct. 19, 1998;143(2):391-401. doi: 10.1083/jcb.143.2.391.
Furuse et al., Claudin-based tight junctions are crucial for the mammalian epidermal barrier: a lesson from claudin-1-deficient mice. J Cell Biol. Mar. 18, 2002;156(6):1099-111. doi: 10.1083/jcb.200110122. Epub Mar. 11, 2002.
Furuse et al., Occludin: a novel integral membrane protein localizing at tight junctions. J Cell Biol. Dec. 1993;123(6 Pt 2):1777-88. doi: 10.1083/jcb.123.6.1777.
Gage et al., Experimental cryosurgery investigations in vivo. Cryobiology. Dec. 2009;59(3):229-43. doi: 10.1016/j.cryobiol.2009.10.001. Epub Oct. 13, 2009.

Garaulet et al., Relationship between fat cell size and number and fatty acid composition in adipose tissue from different fat depots in overweight/obese humans. Int J Obes (Lond). Jun. 2006;30(6):899-905.
Garbay et al., Myelin synthesis in the peripheral nervous system. Prog Neurobiol. Jun. 2000;61(3):267-304.
Garibyan et al., Neural Selective Cryoneurolysis with Ice Slurry Injection in a Rat Model. Anesthesiology. Jul. 2020;133(1):185-194. doi: 10.1097/ALN.0000000000003124.
Garibyan et al., Subcutaneous Fat Reduction with Injected Ice Slurry. Plast Reconstr Surg. Apr. 2020;145(4):725e-733e. doi: 10.1097/PRS.0000000000006658.
Ge et al., Calculations of Freezing Point Depression, Boiling Point Elevation, Vapor Pressure and Enthalpies of Vaporization of Electrolyte Solutions by a Modified Three-Characteristic Parameter Correlation Model. J Sol Chem. Jul. 9, 2009;38(9):1097-17.
Ge et al., Estimation of Freezing Point Depression, Boiling Point Elevation, and Vaporization Enthalpies of Electrolyte Solutions. Ind Eng Chem Res. Jan. 15, 2009;48(4):2229-35.
Gradinger et al., Abdominoplasty. The Art of Aesthetic Surgery: Principles and Techniques. Foad Nahai ed., 1st Ed. 2005. 74 pages.
Graham et al., Characteristics of a human cell line transformed by DNA from human adenovirus type 5. J Gen Virol. Jul. 1977;36(1):59-74. doi: 10.1099/0022-1317-36-1-59.
Grant et al., Perineural antinociceptive effect of opioids in a rat model. Acta Anaesthesiol Scand. Aug. 2001;45(7):906-10. doi: 10.1034/j.1399-6576.2001.045007906.x.
Hackel et al., Transient opening of the perineurial barrier for analgesic drug delivery. Proc Natl Acad Sci U S A. Jul. 17, 2012;109(29):E2018-27. doi: 10.1073/pnas.1120800109. Epub Jun. 25, 2012.
Halkier-Sorensen et al., The relevance of low skin temperature inhibiting histamine-induced itch to the location of contact urticarial symptoms in the fish processing industry. Contact Dermatitis. Sep. 1989;21(3):179-83.
Hamamoto et al., Antimicrobial activity and stability to proteolysis of small linear cationic peptides with D-amino acid substitutions. Microbiol Immunol. 2002;46(11):741-9. doi: 10.1111/j.1348-0421.2002.tb02759.x.
Han et al., Efficacy and safety of high concentration lidocaine for trigeminal nerve block in patients with trigeminal neuralgia. Int J Clin Pract. Feb. 2008;62(2):248-54. Epub Nov. 23, 2007. (Abstract Only).
Hargreaves et al., A new and sensitive method for measuring thermal nociception in cutaneous hyperalgesia. Pain. Jan. 1988;32(1):77-88.
Hauser, International Medical Editorial Board Consensus Statement on the Use of Prolotherapy for Musculoskeletal Pain. Journal of Prolotherapy. Dec. 2011; 3(4): 741-848.
Hirakawa et al., Loss and recovery of the blood-nerve barrier in the rat sciatic nerve after crush injury are associated with expression of intercellular junctional proteins. Exp Cell Res. Apr. 1, 2003;284(2):196-210. doi: 10.1016/s0014-4827(02)00035-6.
Ikenouchi et al., Tricellulin constitutes a novel barrier at tricellular contacts of epithelial cells. J Cell Biol. Dec. 19, 2005;171(6):939-45. doi: 10.1083/jcb.200510043.
Junger et al., Hypertonicity regulates the function of human neutrophils by modulating chemoattractant receptor signaling and activating mitogen-activated protein kinase p38. J Clin Invest. Jun. 15, 1998;101(12):2768-79. doi: 10.1172/JCI1354.
Kanda et al., Chronic inflammatory demyelinating polyneuropathy: decreased claudin-5 and relocated ZO-1. J Neurol Neurosurg Psychiatry. May 2004;75(5):765-9. doi: 10.1136/jnnp.2003.025692.
Kasza et al., Medical Ice Slurry Coolants for Inducing Targeted-Organ/Tissue Protective Cooling. Argonne National Labratory. Jun. 2008. 9 pages.
Kauffeld et al., Ice Slurry Applications. Int J Refrig. Dec. 1, 2010;33(8):1491-1505.
Kondoh et al., A novel strategy for the enhancement of drug absorption using a claudin modulator. Mol Pharmacol. Mar. 2005;67(3):749-56. doi: 10.1124/mol.104.008375. Epub Dec. 15, 2004.

(56) References Cited

OTHER PUBLICATIONS

Krause et al., Structure and function of claudins. Biochim Biophys Acta. Mar. 2008;1778(3):631-45. doi: 10.1016/j.bbamem.2007.10.018. Epub Oct. 25, 2007.
Kucenas et al., CNS-derived glia ensheath peripheral nerves and mediate motor root development. Nat Neurosci. Feb. 2008;11(2):143-51. doi: 10.1038/nn2025. Epub Jan. 6, 2008.
Labuz et al., Immune cell-derived opioids protect against neuropathic pain in mice. J Clin Invest. Feb. 2009;119(2):278-86. doi: 10.1172/JCI36246. Epub Jan. 12, 2009.
Lampe et al., Rapid Induction of Heterogeneous Ice Nucleation in a Biologically Compatible Coolant. Int J Transp Phenom. 2011;12(3-4):307-317.
Langert et al., Strategies for Targeted Delivery to the Peripheral Nerve. Front Neurosci. Nov. 27, 2018;12:887. doi: 10.3389/fnins.2018.00887. eCollection 2018.
Lapid, Syringe-Delivered Tumescent Anesthesia Made Easier. Aesthetic Plast Surg. Aug. 2011;35(4):601-2. doi: 10.1007/s00266-010-9625-4. Epub Nov. 24, 2010.
Laverson, Improving abdominoplasty results: reconstruction of the linea alba sulcus by direct fat excision. Aesthet Surg J. Nov.-Dec. 2006;26(6):682-6. doi: 10.1016/j.asj.2006.10.016.
Lenz et al., The freezing threshold of the peripheral motor nerve: an electrophysiological and light-microscopical study on the sciatic nerve of the rabbit. Cryobiology. Oct. 1975;12(5):486-96.
Levin et al., A pilot study of ice-slurry application for inducing laparoscopic renal hypothermia. BJU Int. Jan. 2007;99(1):166-70. Epub Nov. 10, 2006.
Li et al., Changes in the blood-nerve barrier after sciatic nerve cold injury: indications supporting early treatment. Neural Regen Res. Mar. 2015; 10(3): 419-424. doi: 10.4103/1673-5374.153690: 10.4103/1673-5374.153690.
Manasse et al., Myocardial acute and chronic histological modi® cations induced by cryoablation. Eur J Cardiothorac Surg. Mar. 2000;17(3):339-40. doi: 10.1016/sl010-7940(99)00361-9.
Manns et al., Peginterferon alfa-2b plus ribavirin compared with interferon alfa-2b plus ribavirin for initial treatment of chronic hepatitis C: a randomised trial. Lancet. Sep. 22, 2001;358(9286):958-65. doi: 10.1016/s0140-6736(01)06102-5.
Marsland et al., Cryogenic damage to peripheral nerves and blood vessels in the rat. Br J Anaesth. Jun. 1983;55(6):555-8. doi: 10.1093/bja/55.6.555.
Mitchell et al., Degeneration of non-myelinated axons in the rat sciatic nerve following lysolecithin injection. Acta Neuropathol. 1982;56(3):187-93.
Modak et al., Agglomeration Control of Ice Particles in Ice-Water Slurry System Using Surfactant Additives. HVAC&R Res. 2002;8(4):453-66.
Morita et al., Claudin multigene family encoding four-transmembrane domain protein components of tight junction strands. Proc Natl Acad Sci U S A. Jan. 19, 1999;96(2):511-6. doi: 10.1073/pnas.96.2.511.
Mrsny et al., A key claudin extracellular loop domain is critical for epithelial barrier integrity. Am J Pathol. Apr. 2008;172(4):905-15. doi: 10.2353/ajpath.2008.070698. Epub Mar. 18, 2008.
Ohki et al., Interaction of melittin with lipid membranes. Biochim Biophys Acta. Sep. 14, 1994;1194(2):223-32. doi: 10.1016/0005-2736(94)90303-4.
Oku et al., A simple procedure for the determination of the trapped volume of liposomes. Biochim Biophys Acta. Oct. 7, 1982; 691(2): 332-340.
Peltonen et al., Barriers of the peripheral nerve. Tissue Barriers. Jul. 1, 2013;1(3):e24956. doi: 10.4161/tisb.24956. Epub May 30, 2013.
Piña-Oviedo et al., The normal and neoplastic perineurium: a review. Adv Anat Pathol. May 2008;15(3):147-64. doi: 10.1097/PAP.0b013e31816f8519.
Pradel et al., Cryosurgical treatment of genuine trigeminal neuralgia. Br J Oral Maxillofac Surg. Jun. 2002;40(3):244-7.
Pramanick et al., Excipient Selection In Parenteral Formulation Development. Pharma Times. Mar. 2013;45(3):65-77.
Pummi et al., Tight junction proteins ZO-1, occludin, and claudins in developing and adult human perineurium. J Histochem Cytochem. Aug. 2004;52(8):1037-46. doi: 10.1369/jhc.3A6217.2004.
Rathmell et al., Chapter 14—Intercostal Nerve Block and Neurolysis. Atlas of Image-Guided Intervention in Regional Anesthesia and Pain Medicine. 2012. p. 201-203.
Rengachary et al., Effect of glycerol on peripheral nerve: an experimental study. Neurosurgery. Dec. 1983;13(6):681-8. doi: 10.1227/00006123-198312000-00012.
Richner et al., Functional and Structural Changes of the Blood-Nerve-Barrier in Diabetic Neuropathy. Front Neurosci. Jan. 14, 2019;12:1038. doi: 10.3389/fnins.2018.01038. eCollection 2018.
Rousset et al., Presence and cell growth-related variations of glycogen in human colorectal adenocarcinoma cell lines in culture. Cancer Res. Feb. 1979;39(2 Pt 1):531-4.
Sagie et al., Prolonged sensory-selective nerve blockade. Proc Natl Acad Sci U S A. Feb. 23, 2010;107(8):3740-5. doi: 10.1073/pnas.0911542107. Epub Feb. 4, 2010.
Santamaria et al., Tetrodotoxin, epinephrine, and chemical permeation enhancer combinations in peripheral nerve blockade. Anesth Analg. Jun. 2017;124(6):1804-1812. doi: 10.1213/ANE.0000000000002072.
Segev et al., Endocardial cryotherapy as a novel strategy of improving myocardial perfusion in a patient with severe coronary artery disease. Catheter Cardiovasc Interv. Oct. 2003;60(2):229-32. doi: 10.1002/ccd.10621.
Shikanov et al., Microparticulate ice slurry for renal hypothermia: laparoscopic partial nephrectomy in a porcine model. Urology. Oct. 2010;76(4):1012-6. doi: 10.1016/j.urology.2009.12.066. Epub Mar. 31, 2010.
Simons et al., Effect of chemical permeation enhancers on nerve blockade. Mol Pharm. Jan.-Feb. 2009;6(1):265-73. doi: 10.1021/mp800167a.
Sloviter et al., Effects of the intravenous administration of glycerol solutions to animals and man. J Clin Invest. May 1958;37(5):619-26. doi: 10.1172/JCI103644.
Sonoda et al., Clostridium perfringens enterotoxin fragment removes specific claudins from tight junction strands: Evidence for direct involvement of claudins in tight junction barrier. J Cell Biol. Oct. 4, 1999;147(1):195-204. doi: 10.1083/jcb.147.1.195.
Stein et al., Intrinsic mechanisms of antinociception in inflammation: local opioid receptors and beta-endorphin. J Neurosci. Apr. 1990;10(4):1292-8. doi: 10.1523/JNEUROSCI.10-04-01292.1990.
Stevens et al., Molecular and Histological Evidence Detailing Clinically Observed Skin Improvement Following Cryolipolysis. Aesthet Surg J. May 17, 2021;sjab226. doi: 10.1093/asj/sjab226. Online ahead of print.
Stevens, Does Cryolipolysis Lead to Skin Tightening? A First Report of Cryodermadstringo. Aesthet Surg J. Aug. 2014;34(6):NP32-4. doi: 10.1177/1090820X14539699. Epub Aug. 1, 2014.
Sugiritama, Histology of Nervous System. Educational Staff at Medical Faculty of Udayana University. Published Jun. 23, 2009 (available at https://www.slideshare.net/sugiritama/histologic-structure-of-nervous-system).
Suzuki et al., Particle Size Depression and Drag Reduction of Ice Slurry Treated with Combination Additives of Surfactants and Poly(vinyl alcohol). J Chem Eng Jap. 2010;43(6):482-6.
Takahashi et al., Role of C-terminal regions of the C-terminal fragment of Clostridium perfringens enterotoxin in its interaction with claudin-4. ontrol Release. Nov. 2, 2005;108(1):56-62. doi: 10.1016/j.jconrel.2005.07.008. Epub Aug. 8, 2005.
Todd et al., Ionic permeability of the frog sciatic nerve perineurium: parallel studies of potassium and lanthanum penetration using electrophysiological and electron microscopic techniques. J Neurocytol. Aug. 2000;29(8):551-67. doi: 10.1023/a:1011015916768.
Van Eps et al., Distal limb cryotherapy for the prevention of acute laminitis. Clin Tech Equine Pract. Mar. 1, 2004;3(1):64-70.
Vanden Hoek et al., Induced hypothermia by central venous infusion: saline ice slurry versus chilled saline. Crit Care Med. Sep. 2004;32(9 Suppl):S425-31.

(56) References Cited

OTHER PUBLICATIONS

Vietor et al., Perturbation of the tight junction permeability barrier by occludin loop peptides activates beta-catenin/TCF/LEF-mediated transcription. EMBO Rep. Apr. 2001;2(4):306-12. doi: 10.1093/embo-reports/kve066.

Weerasuriya et al., Modification of permeability of frog perineurium to [14C]-sucrose by stretch and hypertonicity. Brain Res. Sep. 21, 1979 ;173(3):503-12. doi: 10.1016/0006-8993(79)90244-0.

Wen et al., Selective decrease in paracellular conductance of tight junctions: role of the first extracellular domain of claudin-5. Mol Cell Biol. Oct. 2004;24(19):8408-17. doi: 10.1128/MCB.24.19.8408-8417.2004.

Winkler et al., Molecular determinants of the interaction between Clostridium perfringens enterotoxin fragments and claudin-3. J Biol Chem. Jul. 10, 2009;284(28):18863-72. doi: 10.1074/jbc.M109.008623. Epub May 8, 2009.

Wong et al., A synthetic peptide corresponding to the extracellular domain of occludin perturbs the tight junction permeability barrier. J Cell Biol. Jan. 27, 1997;136(2):399-409. doi: 10.1083/jcb.136.2.399.

Wong et al., Targeted and reversible disruption of the blood-testis barrier by an FSH mutant-occludin peptide conjugate. FASEB J. Feb. 2007;21(2):438-48. doi: 10.1096/fj.05-4144com. Epub Dec. 13, 2006.

Wu et al., Identification of new claudin family members by a novel PSI-BLAST based approach with enhanced specificity. Proteins. Dec. 1, 2006;65(4):808-15. doi: 10.1002/prot.21218.

Yamamoto et al., Adipose depots possess unique developmental gene signatures. Obesity (Silver Spring). May 2010;18(5):872-878. doi: 10.1038/oby.2009.512. Epub Jan. 28, 2010. Erratum in:Obesity (Silver Spring). May 2010;18(5):1064.

Yang et al., Getting Drugs across Biological Barriers. Adv Mater. Oct. 2017;29(37):10.1002/adma.201606596. doi: 10.1002/adma.201606596. Epub Jul. 28, 2017.

Yao et al., Medical Polymer Materials. Chemical Industry Press. Apr. 30, 2008;908-10.

Zelickson et al., Cryolipolysis for Noninvasive Fat Cell Destruction: Initial Results from a Pig Model. Dermatol Surg. Oct. 2009;35(10):1462-70. doi: 10.1111/j.1524-4725.2009.01259.x. Epub Jul. 13, 2009.

Zimmermann, Ethical guidelines for investigations of experimental pain in conscious animals. Pain. Jun. 1983;16(2):109-110. doi: 10.1016/0304-3959(83)90201-4.

Zollner et al., Painful inflammation-induced increase in mu-opioid receptor binding and G-protein coupling in primary afferent neurons. Mol Pharmacol. Aug. 2003;64(2):202-10. doi: 10.1124/mol.64.2.202.

Zwanziger et al., A peptidomimetic tight junction modulator to improve regional analgesia. Mol Pharm. Jun. 4, 2012;9(6):1785-94. doi: 10.1021/mp3000937. Epub May 10, 2012.

* cited by examiner (Injection Site)

(Room Temperature Hetastarch)

(Cold Hetastarch)

(Control Site)

(Control)

(Cold Slurry)

(Control)

(Cold Slurry)

(Room Temperature
TWEEN® 20 Solution)

(Cold TWEEN® 20 Slurry)

(Control)

(Control)

(Cold Slurry)

(Control)

(Cold Slurry)

(Room Temperature
PEG Solution)

(Cold PEG Slurry)

(Control)

(Control)

(Cold Slurry)

(Control)

(Cold Slurry)

(Pre-Injection)

(14 Days Post-Injection)

(Pre-Injection)

(Pre-Injection)

(8 Weeks Post-Injection)

(8 Weeks Post-Injection)

(Injection Site)

(Injection Depth)

(Slurry at Site of Pharyngeal Fat)

(Broader Area of Fat and Corresponding Depth)

(Warm Normal Saline at +37° C)

(Normal Saline Cold Slurry)

(Warm Normal Saline at +37° C)

(Normal Saline Cold Slurry)

(Normal Saline Slurry + 10% Glycerol)

(Room Temperature Normal Saline + 10% Glycerol)

(Normal Saline Slurry + 10% Glycerol)

(Room Temperature Normal Saline + 10% Glycerol)

(Normal Saline Slurry + 10% Glycerol)

(Room Temperature Normal Saline + 10% Glycerol)

(Normal Saline Slurry + 10% Glycerol)

(Room Temperature Normal Saline + 10% Glycerol)

(Control Mouse – Baseline)

(Control Mouse – 4 Week Follow Up)

(Treated Mouse – Baseline)

(Treated Mouse – 4 Week Follow Up)

INJECTABLE SLURRIES AND METHODS OF MANUFACTURING THE SAME

CROSS-REFERENCES TO RELATED APPLICATIONS

The present application is a continuation of and claims priority to U.S. patent application Ser. No. 16/288,073, filed Feb. 27, 2019, which is a continuation-in-part of U.S. patent application Ser. No. 15/505,042, which is a U.S. National Phase of PCT/US2015/047301, filed on Aug. 27, 2015, which claims priority to U.S. Provisional Patent Application Ser. No. 62/042,979, filed Aug. 28, 2014, U.S. Provisional Patent Application Ser. No. 62/121,329, filed Feb. 26, 2015, and U.S. Provisional Patent Application Ser. No. 62/121,472, filed Feb. 26, 2015. The present application also claims priority to U.S. Patent Application Ser. No. 17/188,359, which is a continuation of U.S. patent application Ser. No. 15/505,042, which is a U.S. National Phase of PCT/US2015/047301, filed on Aug. 27, 2015, which claims priority to U.S. Provisional Patent Application Ser. No. 62/042,979, filed Aug. 28, 2014, U.S. Provisional Patent Application Ser. No. 62/121,329, filed Feb. 26, 2015, and U.S. Provisional Patent Application Ser. No. 62/121,472, filed Feb. 26, 2015. The present application also claims priority to U.S. patent application Ser. No. 17/236,567, which is a continuation of U.S. patent application Ser. No. 15/505,039, which is a U.S. National Phase of PCT/US2015/047292, filed on Aug. 27, 2015, which claims priority to U.S. Provisional Patent Application Ser. No. 62/042,979, filed Aug. 28, 2014, U.S. Provisional Patent Application Ser. No. 62/121,329, filed Feb. 26, 2015, and U.S. Provisional Patent Application Ser. No. 62/121,472, filed Feb. 26, 2015. The entire disclosures of the aforementioned applications are incorporated herein by reference.

BACKGROUND OF THE INVENTION

Although various devices and techniques seek to selectively target certain tissues, there remains a need for higher resolution and specificity in targeting selected tissues while avoiding harm to non-selected tissues.

SUMMARY OF THE INVENTION

One aspect of the invention provides a slurry comprising: a plurality of sterile ice particles having a largest cross-sectional dimension less than about 1.5 mm; and a biocompatible surfactant. In one aspect, the present disclosure provides This aspect of the invention can have a variety of embodiments. The plurality of sterile ice particles can have a largest cross-sectional dimension less than a value selected from the group consisting of: about 1.25 mm, about 1 mm, about 0.9 mm, about 0.8 mm, about 0.7 mm, about 0.6 mm, about 0.5 mm, about 0.4 mm, about 0.3 mm, about 0.2 mm, and about 0.1 mm.

The biocompatible surfactant can be one or more selected from the group consisting of: a solvent, a detergent, a wetting agent, an emulsifier, a foaming agent, and a dispersant. The biocompatible surfactant can be one or more selected from the group consisting of: anionic, cationic, amphoteric, and nonionic. The biocompatible surfactant can be glycerol. The biocompatible surfactant can be urea. The foregoing and other aspects and advantages of the disclosure will appear from the following description. In the description, reference is made to the accompanying drawings which form a part hereof, and in which there is shown by way of illustration a preferred configuration of the disclosure. Such configuration does not necessarily represent the full scope of the disclosure, however, and reference is made therefore to the claims and herein for interpreting the scope of the disclosure.

The plurality of ice particles can constitute between about 0.1% and about 75% of the slurry by weight. The plurality of ice particles can constitute a percentage by weight selected from the group consisting of: between about 0.1% and 1%, between about 1% and 10%, between about 10% and about 20%, between about 20% and about 30%, between about 30% and about 40%, between about 40% and about 50%, between about 50% and about 60%, between about 60% and about 70%, and greater than about 50%. The plurality of ice particles can constitute between about 0.1% and about 50% of the slurry by weight.

The slurry can further include a therapeutic compound.

The therapeutic compound can be selected from the group consisting of: an anesthetic and an analgesic. The therapeutic compound can be a water-soluble anesthetic. The therapeutic compound can be selected from the group consisting of: prilocaine, bupivacaine, prilocaine, tetracaine, procaine, mepivicaine, etidocaine, lidocaine, QX-314, and a non-steroidal anti-inflammatory drugs (NSAID).

The therapeutic compound can be a vasoconstrictor. The vasoconstrictor can be selected from the group consisting of: epinephrine, norepinephrine, a selective adrenergic agonist, a nonselective adrenergic agonist, and a corticosteroid.

The slurry can further include one or more selected from the group consisting of: microbubbles, nanobubbles, and biodegradable solids.

The slurry can further include a toxin. The toxin can be ethanol.

The slurry can be hypertonic. The slurry can be hypotonic.

The slurry can have a mean temperature selected from the group consisting of: about +10° C., about +9° C., about +8° C., about +7° C., about +6° C., about +5° C., about +4° C., about +3° C., about +2° C., about +1° C., about 0° C., about −1° C., about 2° C., about −3° C., about −4° C., about 5° C., about −6° C., about 7° C., about 8° C., about 9° C., about 10° C., about 11° C., about 12° C., about 13° C., about 14° C., about 15° C., between about 15° C. and about 25° C., between about 25° C. and about 50° C., and between about 50° C. and about 75° C.

The slurry can have a mean temperature of about +5° C. or lower.

Another aspect of the invention provides a slurry including: a plurality of sterile ice particles having a largest cross-sectional dimension less than about 1.5 mm; a biocompatible surfactant; and a foam comprising a plurality of gas bubbles.

This aspect of the invention can have a variety of embodiments. The slurry can have a mean temperature selected from the group consisting of: about +10° C., about +9° C., about +8° C., about +7° C., about +6° C., about +5° C., about +4° C., about +3° C., about +2° C., about +1° C., about 0° C., about −1° C., about 2° C., about −3° C., about −4° C., about 5° C., about 6° C., about 7° C., about 8° C., about 9° C., about 10° C., about 11° C., about 12° C., about 13° C., about 14° C., about 15° C., between about 15° C. and about 25° C., between about 25° C. and about 50° C., and between about 50° C. and about 75° C.

Another aspect of the invention provides a slurry including: a plurality of sterile ice particles having a largest cross-sectional dimension less than about 1.5 mm; and a biocompatible excipient.

This aspect of the invention can have a variety of embodiments. The slurry can have a mean temperature selected from the group consisting of: about +10° C., about +9° C., about +8° C., about +7° C., about +6° C., about +5° C., about +4° C., about +3° C., about +2° C., about +1° C., about 0° C., about −1° C., about 2° C., about −3° C., about −4° C., about 5° C., about 6° C., about 7° C., about 8° C., about 9° C., about 10° C., about 11° C., about 12° C., about 13° C., about 14° C., about 15° C., between about 15° C. and about 25° C., between about 25° C. and about 50° C., and between about 50° C. and about 75° C.

Another aspect of the invention provides a slurry including: a plurality of sterile ice particles having a largest cross-sectional dimension less than about 1.5 mm; and a lipolytic agent.

This aspect of the invention can have a variety of embodiments. The lipolytic agent can be a detergent. The detergent can be deoxycholate. The lipolytic agent can be an alcohol. The lipolytic agent can be an organic solvent.

The slurry can have a mean temperature selected from the group consisting of: about +10° C., about +9° C., about +8° C., about +7° C., about +6° C., about +5° C., about +4° C., about +3° C., about +2° C., about +1° C., about 0° C., about −1 C, about 2° C., about −3° C., about −4° C., about 5° C., about −6° C., about 7° C., about 8° C., about 9° C., about 10° C., about 11° C., about 12° C., about 13° C., about 14° C., about 15° C., between about 15° C. and about 25° C., between about 25° C. and about 50° C., and between about 50° C. and about 75° C.

Another aspect of the invention a method of treating a subject. The method includes: injecting a slurry as described herein into a treatment region of the subject.

This aspect of the invention can have a variety of embodiments. The treatment region can be selected from the group consisting of: proximate to a nerve, proximate to subcutaneous adipose tissue, proximate to breast tissue, proximate to visceral fat, fatty tissue proximate to the pharynx, fatty tissue proximate to the palate, fatty tissue proximate to the tongue, proximate to a spinal cord lipoma, proximate to a lipomyelomeningocele, proximate to visceral fat, proximate to lipomastia, proximate to a tumor, proximate to cardiac tissue, proximate to pericardial fat, and proximate to epicardial fat.

The treatment region can include one or more tissues selected from the group consisting of: connective, epithelial, neural, joint, cardiac, adipose, hepatic, renal, vascular, cutaneous, and muscle.

The method can further include measuring a temperature of the slurry prior to injection.

The slurry can be injected via gravity flow. The slurry can be injected via pressure injection. The slurry can be injected through one or more selected from the group consisting of: a syringe, a cannula, a catheter, and tubing.

The method can further include pre-cooling the treatment region prior to the injecting step. The method can further include applying energy adjacent to the target tissue. The method can further include applying suction to the treatment region to remove melted slurry.

The injecting step can include injecting a sufficient volume of the slurry to cause tumescent swelling of the treatment region. The injecting step can be repeated a plurality of times.

The method can further include calculating a desired amount of slurry to be injected based on a desired amount of disruption to the treatment region. The slurry can cool the treatment region adjacent to an injection site at a rate greater in magnitude than about −2° C. per minute.

The method can thicken septa. The septa can be in adipose tissue and/or dermis.

The method can further include mixing the slurry with relatively warmer liquid prior to the injecting step.

The slurry can have a mean temperature selected from the group consisting of: about +10° C., about +9° C., about +8° C., about +7° C., about +6° C., about +5° C., about +4° C., about +3° C., about +2° C., about +1° C., about 0° C., about −1° C., about 2° C., about −3° C., about −4° C., about 5° C., about −6° C., about 7° C., about 8° C., about 9° C., about 10° C., about 11° C., about 12° C., about 13° C., about 14° C., about 15° C., between about 15° C. and about 25° C., between about 25° C. and about 50° C., and between about 50° C. and about 75° C.

The slurry can be hypotonic relative to the treatment region. The slurry can be isotonic relative to the treatment region. The slurry can be hypertonic relative to the treatment region.

Another aspect of the invention provides a method of treating a subject. The method includes: injecting the slurry as described herein having a temperature and cooling capacity sufficient to non-selectively disrupt tissue into a treatment region of the subject.

This aspect of the invention can have a variety of embodiments. The treatment region can be selected from the group consisting of: a prostate, a kidney, a heart, and a fibroadenoma.

The slurry can have a mean temperature selected from the group consisting of: about +10° C., about +9° C., about +8° C., about +7° C., about +6° C., about +5° C., about +4° C., about +3° C., about +2° C., about +1° C., about 0° C., about −1 C, about 2° C., about −3° C., about −4° C., about 5° C., about −6° C., about 7° C., about 8° C., about 9° C., about 10° C., about 11° C., about 12° C., about 13° C., about 14° C., about 15° C., between about 15° C. and about 25° C., between about 25° C. and about 50° C., and between about 50° C. and about 75° C.

The slurry can be hypotonic relative to the treatment region. The slurry can be isotonic relative to the treatment region. The slurry can be hypertonic relative to the treatment region.

Another aspect of the invention provides a method of treating a subject. The method includes injecting a slurry into a treatment region of the subject selected from the group consisting of: proximate to a nerve, proximate to subcutaneous adipose tissue, proximate to breast tissue, proximate to visceral fat, fatty tissue proximate to the pharynx, fatty tissue proximate to the palate, fatty tissue proximate to the tongue, proximate to a spinal cord lipoma, proximate to a lipomyelomeningocele, proximate to visceral fat, proximate to lipomastia, proximate to a tumor, proximate to cardiac tissue, proximate to pericardial fat, and proximate to epicardial fat.

This aspect of the invention can have a variety of embodiments. The slurry can include an ionic component.

The slurry can have a temperature and cooling capacity sufficient to non-selectively disrupt tissue into a treatment region of the subject. The slurry can have a mean temperature selected from the group consisting of: about +10° C., about +9° C., about +8° C., about +7° C., about +6° C., about +5° C., about +4° C., about +3° C., about +2° C., about +1° C., about 0° C., about −1° C., about 2° C., about −3° C., about −4° C., about 5° C., about −6° C., about 7° C., about 8° C., about 9° C., about 10° C., about 11° C., about 12° C., about 13° C., about 14° C., about 15° C., between about 15° C. and about 25° C., between about 25° C. and about 50° C., and between about 50° C. and about 75° C.

Another aspect of the invention provides a method of preparing a slurry. The method includes: freezing a plurality of sterile ice particles having a largest cross-sectional dimension less than about 1.5 mm in one or more micromolds; and mixing the plurality of sterile ice particles with one or more biocompatible liquids.

This aspect of the invention can have a variety of embodiments. The plurality of sterile ice particles can have a substantially uniform shape. The one or more micromolds can be fabricated from one or more materials selected from the group consisting of: polymers, plastics, elastomers, silicons, silicones, and metals. The method can further include applying mechanical strain, stress waves, shock waves, or centripetal force to remove the plurality of sterile ice particles from the one or more micromolds.

The slurry can have a mean temperature selected from the group consisting of: about +10° C., about +9° C., about +8° C., about +7° C., about +6° C., about +5° C., about +4° C., about +3° C., about +2° C., about +1° C., about 0° C., about −1° C., about 2° C., about −3° C., about −4° C., about 5° C., about −6° C., about 7° C., about 8° C., about 9° C., about 10° C., about 11° C., about 12° C., about 13° C., about 14° C., about 15° C., between about 15° C. and about 25° C., between about 25° C. and about 50° C., and between about 50° C. and about 75° C.

Another aspect of the invention provides a slurry comprising: a plurality of sterile ice particles having a largest cross-sectional dimension less than about 1.5 mm; and an ionic component selected from the group consisting of: hydrogen ions, lactate, phosphate, zinc ions, sulfur ions, nitrate, ammonium, hydroxide, iron ions, barium ions.

In some aspects, the slurries disclosed herein may be used to treat vascular disease. In some aspects, the present disclosure provides a method for treating vascular disease that includes fabricating a sterile ice slurry including water and ice particles, cooling the sterile ice slurry to a predetermined temperature, and injecting the sterile ice slurry into a desired tissue region. The desired tissue region includes perivascular adipose tissue.

In some aspects, the present disclosure provides an injection system configured to access perivascular adipose tissue. The injection system includes a sterile ice slurry including water and ice particles. The sterile ice slurry is at a predetermined temperature. The injection system further includes an injection device configured to inject the sterile ice slurry into or around perivascular adipose tissue. The ice particles in the sterile ice slurry define a largest cross-sectional diameter of less than 2 millimeters to enable the sterile ice slurry to flow through the injection device.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIG. 12A is an ultrasound image of human skin prior to slurry injection. FIG. 12B is an ultrasound image of human skin after slurry injection.

DEFINITIONS

Figure 1:
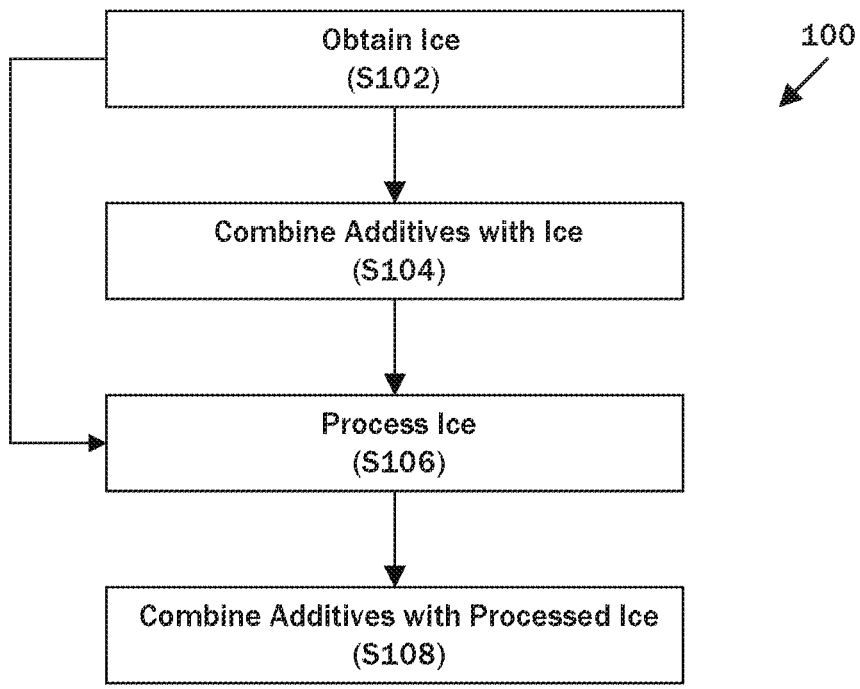
FIG. 1 depicts a method of preparing a slurry according to an embodiment of the invention.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

As used herein, the term "slurry" refers to a plurality of ice particles in an aqueous solution.

DETAILED DESCRIPTION OF THE INVENTION

Various aspects of the invention involve introducing a composition including a cold slurry (e.g., ice slurry) into tissue, e.g., directly into the tissue rather than through a natural conduit of the body such as arteries, veins, or gut. When a volume of ice slurry is directly introduced into a volume of soft tissue, there is rapid heat exchange between the tissue and the slurry. When rapidly and locally injected, a pool of slurry is produced that contacts a target volume of local tissue. By contrast, if a slurry is infused more slowly and with larger volume, the slurry penetrates and flows through spaces in the tissue, producing widespread channels filled with slurry in a process similar to the administration of tumescent anesthesia. Infusion enables sustained flow of slurry through tissue, especially tissue nearby the site of introduction. This tissue can be profoundly cooled to the temperature of the slurry itself by the continuous or prolonged flow of slurry.

In general, there are two periods of heat exchange upon injection of slurry directly into tissue: a rapid equilibration between slurry and local tissue, followed by slower warming to body temperature. During the rapid equilibration, the slurry is warmed and the local tissue is cooled, until an equilibrium temperature is reached that is between the initial temperatures of the slurry and the tissue. During this rapid tissue cooling by heat exchange, three events occur: (1) heat stored by the heat capacity of the slurry and the tissue is exchanged; (2) heat released by the crystallization of tissue lipids is exchanged; and (3) heat absorbed by melting of slurry ice is exchanged. Some or all of the ice in the slurry melts, and some or all of the lipids in the tissue are crystallized, according to the parameters of the tissue and the slurry.

After the rapid heat exchange with the slurry, there is gradual warming by heat exchange with the body. Gradual warming occurs by a combination of heat diffusion from surrounding warm tissue and by convective heating from blood flow. Blood flow can be reduced in the local tissue by pressure or by drugs as discussed in greater detail herein. The desired level of pain relief may depend on temperature, rate of cooling, duration of cooling and the number of cooling cycles.

Injectable Slurries

Embodiments of the invention provide injectable slurries that can be used for selective or non-selective cryotherapy and/or cryolysis. Without being bound by theory, it is believed that such slurries can target and disrupt desired tissue through the extraction of heat from adjacent tissue during melting of the ice component of the slurry.

In addition, the osmolality or osmolarity of the slurry can be adjusted to synergistically induce selective damage through hypertonic or hypotonic injury. For example, the slurries can be isotonic slurries having an osmolarity of about 308 mOsm/L, hypotonic slurries having an osmolarity less than about 308 mOsm/L, or hypertonic slurries having an osmolarity greater than about 308 mOsm/L.

As discussed herein, varying amounts of additives such as freezing point depressants can be added to the slurries. For example, the additives can constitute less than about 20% w/w of the slurry, between about 20% and about 40% w/w of the slurry, and the like.

In one embodiment, the injectable slurry includes a plurality of sterile ice particles and one or more freezing point depressants. The freezing point depressants can also alter the viscosity of the slurry, prevent agglomeration of the ice particles, increase thermal conductivity of fluid phase, and otherwise improve the performance of the slurry.

The degree of freezing point depression can be calculated either using the idealized formula:

$$\Delta T_F = K_F b i$$

wherein $\Delta T_F$ is the freezing point depression (as defined by $T_{F(pure\ solvent)} - T_{F(solution)}$), $K_F$ is the cryoscopic constant, b is molality, and i is the van't Hoff factor representing the number of ion particles per individual molecule of solute (e.g., 2 for NaCl, 3 for $BaCl_2$) or in the formulas proposed in X. Ge & X. Wang, "Estimation of Freezing Point Depression, Boiling Point Elevation and Vaporization enthalpies of electrolyte solutions," 48 *Ind. Eng. Chem. Res.* 2229 35 (2009) and X. Ge & X. Wang, "Calculations of Freezing Point Depression, Boiling Point Elevation, Vapor Pressure and Enthalpies of Vaporization of Electrolyte Solutions by a Modified Three-Characteristic Parameter Correlation Model," 38 *J. Sol. Chem.* 1097-1117 (2009).

In order to ensure that the slurry can be injected into a subject through a needle, a cannula, or a catheter, the size of the ice particles can be controlled. Without being bound by theory, it is believed that a slurry will be injectable if all or most (e.g., greater than about 50% by quantity, greater than about 75% by quantity, greater than about 80% by quantity, greater than about 90% by quantity, greater than about 95% by quantity, greater than about 99% by quantity, and the like) of the ice particles have a largest cross-sectional dimension (i.e., the largest distance between any two points on the surface of the ice particle) no greater than half of the internal diameter of the vessels (e.g., needles, cannulae, catheters, tubing, and the like) to be used. For example, if the slurry is to be injected using a catheter having a 3 mm internal diameter, the ice particles will preferably have a largest cross-sectional dimension less than or equal to about 1.5 mm. In some embodiments, the ice particles have a mean largest cross-sectional dimension of 1 mm or less.

As discussed in greater detail herein, this controlled size can be achieved by controlled generation or processing of the ice particles and/or by filtering, screening, or sorting of the ice particles. Controlled storage, transport, and/or handling of the ice particles and/or slurries can also promote predictable, flowable slurries by preventing thawing and refreezing of the ice particles, which may change the size of the ice particles and/or produce sharp and/or jagged surfaces.

Without being bound by theory, exemplary suitable ice particle sizes for various internal catheter diameters and internal needle diameters are provided in Table 1 and Table 2, respectively, below.

TABLE 1

Recommended Largest Ice Particle Cross-Sections by Catheter Size

| Catheter Internal Diameter | Recommended Largest Cross-Section of Ice Particles |
| --- | --- |
| 4 mm | 2 mm |
| 3 mm | 1.5 mm |
| 2 mm | 1 mm |

TABLE 2

Recommended Largest Ice Particle Cross-Sections by Needle Size

| Needle Gauge | Nominal Internal Diameter | Recommended Largest Cross-Section of Ice Particles |
| --- | --- | --- |
| 7 | 3.81 mm | 1.905 mm |
| 8 | 3.429 mm | 1.7145 mm |
| 9 | 2.997 mm | 1.4985 mm |
| 10 | 2.692 mm | 1.346 mm |
| 11 | 2.388 mm | 1.194 mm |
| 12 | 2.159 mm | 1.0795 mm |
| 13 | 1.803 mm | 0.9015 mm |
| 14 | 1.6 mm | 0.8 mm |
| 15 | 1.372 mm | 0.686 mm |
| 16 | 1.194 mm | 0.597 mm |
| 17 | 1.067 mm | 0.5335 mm |
| 18 | 0.838 mm | 0.419 mm |
| 19 | 0.686 mm | 0.343 mm |
| 20 | 0.603 mm | 0.3015 mm |
| 21 | 0.514 mm | 0.257 mm |
| 22 | 0.413 mm | 0.2065 mm |
| 22s | 0.152 mm | 0.076 mm |
| 23 | 0.337 mm | 0.1685 mm |
| 24 | 0.311 mm | 0.1555 mm |
| 25 | 0.26 mm | 0.13 mm |
| 26 | 0.26 mm | 0.13 mm |
| 26s | 0.127 mm | 0.0635 mm |

TABLE 2-continued

Recommended Largest Ice Particle Cross-Sections by Needle Size

| Needle Gauge | Nominal Internal Diameter | Recommended Largest Cross-Section of Ice Particles |
| --- | --- | --- |
| 27 | 0.21 mm | 0.105 mm |
| 28 | 0.184 mm | 0.092 mm |
| 29 | 0.184 mm | 0.092 mm |
| 30 | 0.159 mm | 0.0795 mm |
| 31 | 0.133 mm | 0.0665 mm |
| 32 | 0.108 mm | 0.054 mm |
| 33 | 0.108 mm | 0.054 mm |
| 34 | 0.0826 mm | 0.0413 mm |

One or more freezing point depressants can be added to form sub-0° C. slurries that remain injectable. Freezing point depressants can also reduce the temperature of the slurries to temperatures below 0° C. Suitable freezing point depressants include biocompatible compounds such salts (e.g., sodium chloride), ions, Lactated Ringer's solution, sugars (e.g., glucose, sorbitol, mannitol, hetastarch, sucrose, or a combination thereof), biocompatible surfactants such as glycerol (also known as glycerin or glycerine), other polyols, other sugar alcohols, and/or urea, and the like. In particular, some biocompatible surfactants such as glycerol are believed to cause ice particles to shrink and become rounder and also serves as a cryo-protectant for non-lipid-rich cells. Other exemplary biocompatible surfactants include sorbitan esters of fatty acids, polysorbates, polyoxyethylene sorbitan monooleate (also known as polysorbate 80 and available under the TWEEN® 80 trademark from Croda Americas LLC of New Castle, Del.), sorbitan monooleate polyoxyethylene sorbitan monolaurate (also known as polysorbate 80 and available under the TWEEN® 80 trademark from Croda Americas LLC of New Castle, Del.), polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate), sorbitan ester, poloxamater, lecithin, polyoxyethylene-polyoxypropylene copolymers (available under the PLURONICS® trademark from BASF Corporation of Mount Olive, N.J.), sorbitan trioleate (available under the SPAN® 85 trademark from Sigma-Aldrich of St. Louis, Mo.) and the like.

Surfactants can also act as a solvent, detergent, wetting agent, emulsifier, foaming agent, and/or dispersant. Surfactants can be anionic, cationic, amphoteric, or nonionic. Biocompatible surfactants can be included in injectable ice slurries.

Injectable slurries can be configured to have a desired temperature and to extract a desired amount of heat per unit of volume or mass of slurry. Specifically, the solute (i.e., freezing point depressant) concentration dictates the temperature of the slurry and the ice content of the slurry determines the amount of heat extracted by the slurry.

For selectively-destructive slurries that target the relative vulnerability of lipid-rich cells, the slurry is preferably isotonic relative to the subject's cells, e.g., having an osmolarity of about 308 mOsm/L. For example, slurries including normal saline and 20% glycerol were able to target lipid rich cells while avoiding acute unselective necrosis. Broadly destructive slurries can achieve colder temperatures and greater destructive power by increasing the solute concentration (e.g., to 20% w/v saline) to form a hypertonic solution (i.e., a solution having an osmolarity greater than about 308 mOsm/L) that will also disrupt cells through osmotic pressure. As the ice melts, the solute concentration will decrease.

The injectable slurries can contain varying proportions of ice. For example, the slurries can contain between about 0.1% and about 75% ice by weight, between about 0.1% and 1% ice by weight, between about 1% and 10% ice by weight, between about 10% and about 20% ice by weight, between about 20% and about 30% ice by weight, between about 30% and about 40% ice by weight, between about 40% and about 50% ice by weight, between about 50% and about 60% ice by weight, between about 60% and about 70% ice by weight, and greater than about 50% ice by weight. (The proportions of ice by volume are slightly higher due to the densities of solid and liquid water.)

In some embodiments, the injectable slurry further comprises a therapeutic compound (which can be included in calculating the solute concentration above). The therapeutic compound can be a liquid, a gas, or a solid.

In one embodiment, the therapeutic compound is an anesthetic and/or an analgesic, for example, a water-soluble anesthetic (e.g., prilocaine), bupivacaine, prilocaine, tetracaine, procaine, mepivicaine, etidocaine, lidocaine, non-steroidal anti-inflammatory drugs (NSAIDs), steroids (e.g., methylprednisone), and the like. Inclusion of an anesthetic in the slurry can be particularly advantageous when the slurry is used to provide a nerve block because (i) the effect of the anesthetic will provide immediate confirmation that the slurry is being injected in the correct location and (ii) the anesthetic can provide pain relief until the cyroneurolysis nerve block is effective (potentially after 48 hours).

In one embodiment, the anesthetic is QX-314, N-ethyl bromide, a quaternary lidocaine derivative that is a permanently charged molecule capable of providing long term (over 24 hours) anesthesia. Unlike lidocaine, QX-314 can provide more selective blocking of nociceptors and with longer duration of action and less side effects. QX-314 is a charged molecule that needs to enter the cell and block the sodium channels intracellularly. The ability of QX-314 to block from the inside, but not the outside of neuronal membranes could be exploited to block only desired neurons. Combining QX-314 with the cold slurry injections described herein can selectively target cold sensing nociceptive sensory neurons to provide selective and long lasting anesthesia.

In another embodiment, the therapeutic compound is a vasoconstrictor such as epinephrine, norepinephrine, other selective or nonselective adrenergic agonists, or a corticosteroid. Vasoconstrictors can advantageously prolong the cooling effect of the slurry by reducing warming from blood flow. (Pressure or suction can also be used to reduce blood flow and/or isolate the target tissue as discussed in U.S. Pat. Nos. 7,367,341 and 8,840,608.)

In still another embodiment, the injectable slurry can include one or more lipolytic agents to enhance the reduction of lipid-rich cells. Exemplary lipolytic agents include biocompatible surfactants, bile salts and their derivatives (e.g., deoxycholic acid), phosphatidylcholine (lecithin), catecholamines, B-agonists (e.g., isoproterenol), alpha 2-agonists (e.g., yohimbine), phosphodiesterase inhibitors (e.g., aminophylline, theophylline), corticosteroids, caffeine, hyalorunidase, collagenase, alpha-tocopherol, ethanol, benzyl alcohol, carnitine, catechin, cysteine, gallic acid, laminarin, rutin, myrecetin, alpha MSH, melilotus, resveratrol, genistein, and the like. Such agents can disrupt adipose tissue morphology when injected at room temperature and be particularly useful in augmenting disruption of adipose tissue morphology when included in slurries prepared for cryolipolysis and/or cryoneurolysis. Table 3 provides a list of exemplary lipolytic agents, cell targets, and hypothesized mechanisms of action.

TABLE 3

Exemplary Lipolytic (Lipid-Rich-Cell-Targeting) Agents

| Compound Category | Cell Target | Cell Lysis? | Hypothesized Mechanism of Action |
|---|---|---|---|
| Bile salts and their derivatives (e.g., deoxycholic acid) | Adipocyte | Yes | Solubilize/break down adipocyte cell membrane through detergent effect |
| Phosphatidylcholine (lecithin) | Adipocyte | No | Buffers ablative effects of detergents (e.g., deoxycholate, cholates, and the like) |
| Catecholamines, B-agonists (e.g., isoproterenol) | Adipocyte | No | Increased lipolysis; stimulation of B-adrenoreceptor increases cAMP |
| Alpha 2-agonists (e.g., yohimbine) | Adipocyte | No | Increased lipolysis |
| Phosphodiesterase inhibitors (e.g., aminophylline, theophylline) | Adipocyte | No | Increased lipolysis; phosphodiesterase inhibition increases cAMP |
| Corticosteroids | Adipocyte | No | Block downregulation of B-adrenoreceptors |
| Forskolin (plant derivative: *Coleus forskohlii*) | Adipocyte | No | Increased lipolysis; activates adenylate cyclase independent of adrenoreceptor resulting in increased cAMP |
| Caffeine | Adipocyte | No | Increased lipolysis; multiple mechanisms (Phosphodiesterase inhibition, increased catecholamine release, adenosine antagonist) |
| Collagenase | Fibrous septae | N/A | Dissolves fibrous septae |

In some embodiments, the injectable slurry further includes microbubbles or nanobubbles to aid in imaging (particularly by ultrasound) and verification of the injection site. Suitable microbubbles and nanobubbles and methods for making the same are described in U.S. Pat. Nos. 7,897,141 and 8,715,622 and U.S. Patent Application Publication No. 2008/0247957, 2008/0279783, and 2009/0028797.

In some embodiments, specifically non-selective injectable slurries, the slurry can further include a toxin or sclerosing agents such as ethanol, detergents, and the like.

Slurries can contain other emulsifiers and excipients included in other parenteral solutions such as those described in Sougata Pramanick et al., "Excipient Selection In Parenteral Formulation Development," 45(3) *Pharma Times* 65-77 (2013). Exemplary excipients are listed in Table 4 below. The substances described herein can be administered in a variety of doses that can produce varying effects. For example, low doses of a particular substance can act as an inert excipient, but exert a therapeutic effect at a higher concentration.

TABLE 4

Exemplary Excipients

| Category | Examples |
|---|---|
| Bulking Agents | Sucrose, lactose, trehalose, mannitol, sorbitol, glucose, raffinose, glycine, histidine, PVP (K40) |
| Buffering Agents | Sodium citrate, sodium phosphate, sodium hydroxide, tris base-65, tris acetate, tris HCl- 65 |
| Tonicity Modifiers | Dextrose |
| Collapse Temperature Modifiers | Dextran, ficoll, gelatin, hydroxyethyl starch |
| Antimicrobial Preservatives | Benzalkonium chloride, benzethonium chloride, benzyl alcohol, chlorobutanol, m-cresol, myristyl gamma-picolinium chloride, paraben methyl, paraben propyl, phenol, 2-penoxyethanol, phenyl mercuric nitrate, thimerosal |
| Chelating Agents | Calcium disodium EDTA (ethylenediaminetetra acetic acid), disodium EDTA, calcium versetamide Na, calteridol, DTPA |
| Antioxidant and Reducing Agents | Acetone sodium bisulfate, argon, ascorbyl palmitate, ascorbate (sodium/acid), bisulfite sodium, butylated hydroxyl anisole, butylated hydroxyl toluene (BHT), cystein/cysteinate HCl, dithionite sodium, gentistic acid, gentistic acid ethanolamine, glutamate monosodium, glutathione, formaldehyde sulfoxylate sodium, metabisulfite potassium, metabisulfite sodium, methionine, monothioglycerol (thioglycerol), nitrogen, propyl gallate, sulfite sodium, tocopherol alpha, alpha tocopherol hydrogen succinate, thioglycolate sodium, thiourea, anhydrous stannous chloride |
| Solvents and Co-Solvents | Benzyl benzoate, oils, castor oil, cottonseed oil, N,N dimethylacetamide, ethanol, dehydrated ethanol, glycerin/glycerol, N-methyl-2-pyrrolidone, peanut oil, PEG, PEG 300, PEG 400, PEG 600, PEG 3350, PEG 4000, poppyseed oil, propylene glycol, safflower oil, sesame oil, soybean oil, vegetable oil, oleic acid, polyoxyethylene castor, sodium acetate-anhydrous, sodium carbonate- anhydrous, triethanolamine, deoxycholate |

TABLE 4-continued

Exemplary Excipients

| Category | Examples |
|---|---|
| Buffers and pH-Adjusting Agents | Acetate, ammonium sulfate, ammonium hydroxide, arginine, aspartic acid, benze sulfonic acid, benzoate sodium/acid, bicarbonate-sodium, boric acid/sodium, carbonate/sodium, carbon dioxide, citrate, diethanolamine, glucono delta lactone, glycine/glycine HCl, histidine/histidine HCl, hydrochloric acid, hydrobromic acid, lysine (L), maleic acid, meglumine, methanesulfonic acid, monoethanolamine, phosphate (acid, monobasic potassium, dibasic potassium, monobasic sodium, dibasic sodium and tribasic sodium), sodium hydroxide, succinate sodium/disodium, sulfuric acid, tartarate sodium/acid, tromethamine (Tris) |
| Stabilizer | Aminoethyl sulfonic acid, asepsis sodium bicarbonate, L-cysteine, dietholamine, diethylenetriaminepentacetic acid, ferric chloride, albumin, hydrolyzed gelatin, insitol, D,L-methionine |
| Surfactant | Polyoxyethylene sorbitan monooleate (TWEEN ® 80), Sorbitan monooleate, polyoxyethylene sorbitan monolaurate (TWEEN ® 20), lecithin, polyoxyethylene-polyoxypropylene copolymers (PLURONICS ®), polyoxyethylene monolaurate, phosphatidylcholines, glyceryl fatty acid esters, urea |
| Complexing/ Dispersing Agents | Cyclodextrins (e.g., hydroxypropyl-B-cyclodextrin, sulfobutylether-B-cyclodextrin) |
| Viscosity Building Agents | Sodium carboxymethyl cellulose, acacia, gelatin, methyl cellulose, polyvinyl pyrrolidone |

Exemplary properties of various additives are summarized in Table 5 below.

TABLE 5

Properties of Exemplary Additives

| Agent | Lipolytic | Miscible | Osmo/Cryo Protectant | Surfactant/ Solvent | Cell Permeable |
|---|---|---|---|---|---|
| Glycerol | | X | X | X | X |
| Urea | | X | | X | X |
| Ethylene Glycol | | X | X | X | X |
| PEG | | X | | X | |
| TRITON ™ X-100 Detergent | | X | | X | |
| Propylene Glycol | | X | | X | |
| Ethanol | | X | | X | |
| Polyvinyl Alcohol | | X | X | X | |
| Adonitol | | X | X | | |
| Erythritol | | X | X | | |
| Dextran (Glucan) | | X | X | | |
| Dextrose 20% in Water (D20W) (Free Water Solution) | | X | X | | X |
| Mannitol (Sugar Alcohols) | | | X | | |
| Sucrose (Sugar) | | | X | X | X |
| Hetastarch (Colloid) | | | X | X | |
| Epinephrine (Vasoconstrictor) | X | | X | | |
| PLURONIC ® (Poloxamers) | | | X | | X |
| SPAN ® (Sorbitan Esters) | | | X | | X |
| TWEEN ® (Polysorbates) | | | X | | X |
| CREMOPHOR ® (Polyethoxylated Castor Oil) | | | X | | X |
| Caffeine | X | X | | | |
| Cholate | X | X | | X | X |
| Deoxycholate | X | X | | X | X |
| Lecithin | X | X | X | X | |
| Yohimbine | X | X | | | |
| Genistein | X (Pro-Apoptotic Agent) | X | | | |
| Resveratrol | X (Pro-Apoptotic Agent) | X | | | |
| Amino/ Theophylline | X | X | | | |
| Amino Acid (e.g.; Betaine) | | X | X | | |
| Polyvinyl Pyridine (PVP) | | X | X | | |
| Emulsions of Natural Oils | | | | X | |
| Intralipid | | X | | | |
| Electrolytes (Crystalloids) | | X | | | |
| Calcitrol (Potential Cryosensitizer) | | | | | |

As used herein, "intralipid" refers to an emulsion of lipids typically used for intravenous nutrition, e.g., an emulsion of 20% intravenous fat emulsion, 20% soybean oil, 1.2% egg yolk phospholipids (lecithin), 2.25% glycerin, water, and sodium hydroxide to adjust pH. A variety of other intralipid formulations are used in medicine.

Other additives include sugars, monosaccharides, disaccharides, oligosaccharides, polysaccharides, carbohydrates, lipids, anti-metabolites, oils, natural oils (e.g., canola, coconut, corn, cottonseed, flaxseed, olive, palm, peanut, safflower, soybean, and/or sunflower oil), peritoneal dialysis solution, ions (e.g., calcium, potassium, hydrogen, chloride, magnesium, sodium, lactate, phosphate, zinc, sulfur, nitrate, ammonium, carbonate, hydroxide, iron, barium, and the like), and the like.

Foams and Foamy Slurries

Figure 26A:
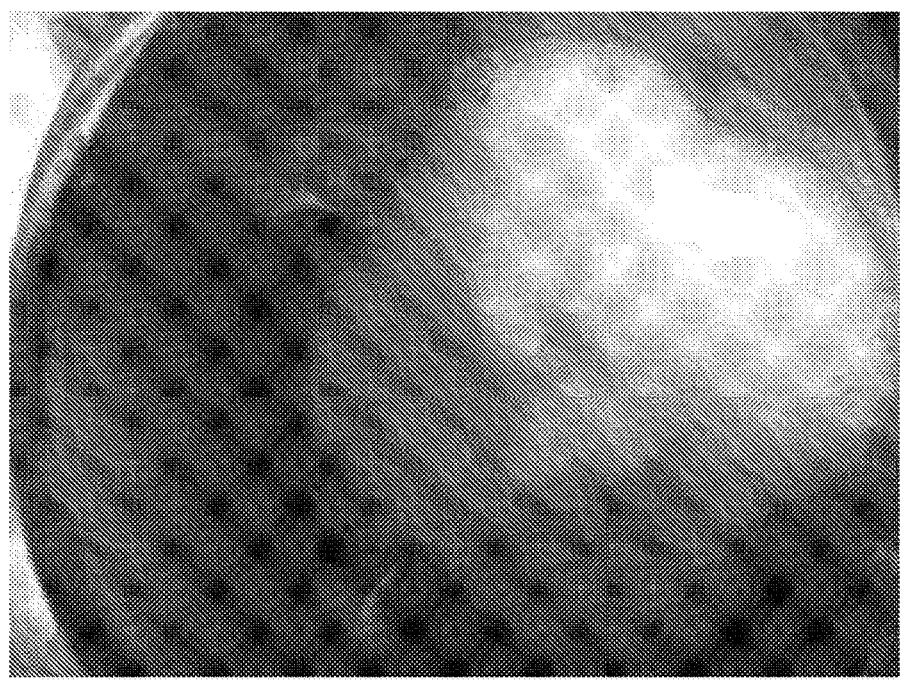
FIGS. 26A and 26B depict a foamy slurry.
Figure 26B:
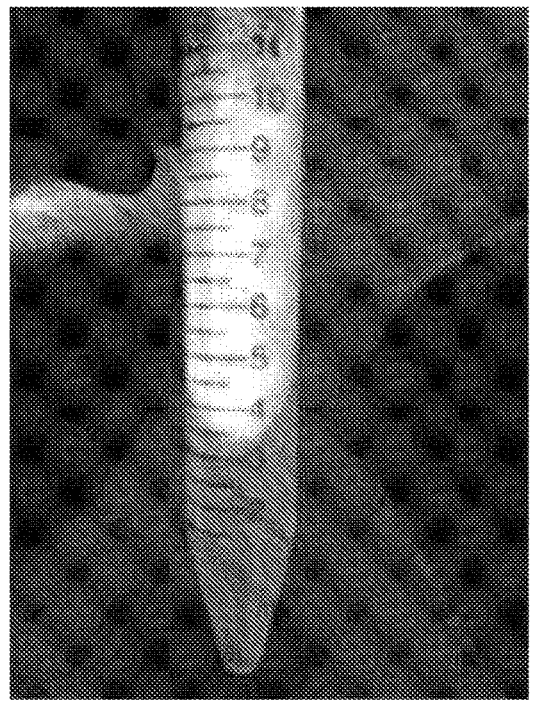

Referring now to FIGS. 26A and 26B, slurry with 5% TWEEN® 20 (polysorbate 20) in lactated Ringer's solution plus 5% dextrose initially had a regular slurry consistency, but became very foamy when reblended. Without being bound by theory, it is believed that foamy slurries can be formed with other detergents.

Figure 27:
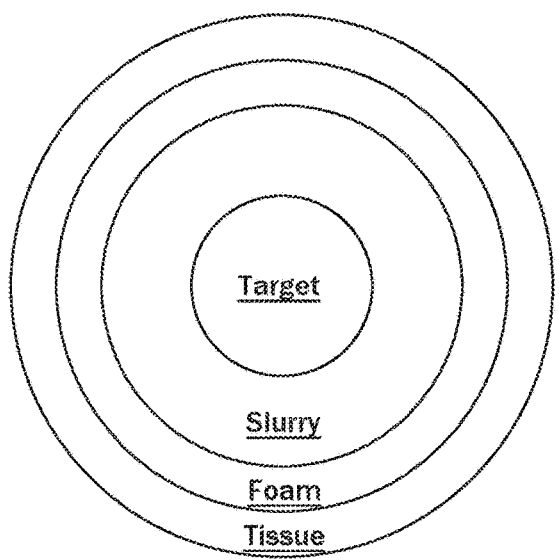
FIG. 27 depicts the use of a foamy slurry as an insulator for further slurry injection(s).

Foamy slurries or other biocompatible foams can be utilized as insulators to further protect adjacent tissue from cold-induced damage. For example, a foamy slurry or other biocompatible foam can first be injected adjacent to a cooling target (e.g., a nerve). A slurry having a higher cooling power can then be injected adjacent to the target and within the foamy slurry or biocompatible foam as depicted in FIG. 27. The foamy slurry or biocompatible foam will act as an insulator, in part due to the entrained air, thereby protecting adjacent tissue from cold-induced damage and shielding the second slurry from warming by adjacent tissue.

Methods of Preparing Slurries

Slurries can be prepared using a variety of methods.

In one embodiment, a slurry is prepared using a commercially-available ice slurry generator such as those available under the MODUPAK™ DEEPCHILL™ trademark from Sunwell Technologies Inc. of Woodbridge, Ontario. Commercially-available slurry generators include scraped surface generators that wipe away (e.g., with blades, augers, brushes) small ice crystals from a chilled surface and mix with water, direct contact generators in which an immiscible primary refrigerant evaporates to supersaturate the water and form small smooth crystals, and super cooling generators in which water is supercooled and released through a nozzle into a storage tank.

FIG. 1 depicts one exemplary method 100 of preparing a slurry.

In step S102, ice is obtained. The ice is preferably sterile ice and can either consist purely or essentially of water or can be a frozen mixture of water and one or more additives as discussed herein.

In step S104, one or more additives are optionally combined with the ice prior to processing. The one or more additives are preferably at or near the desired slurry temperature in order to prevent melting and refreezing of the ice particles.

Figure 18:
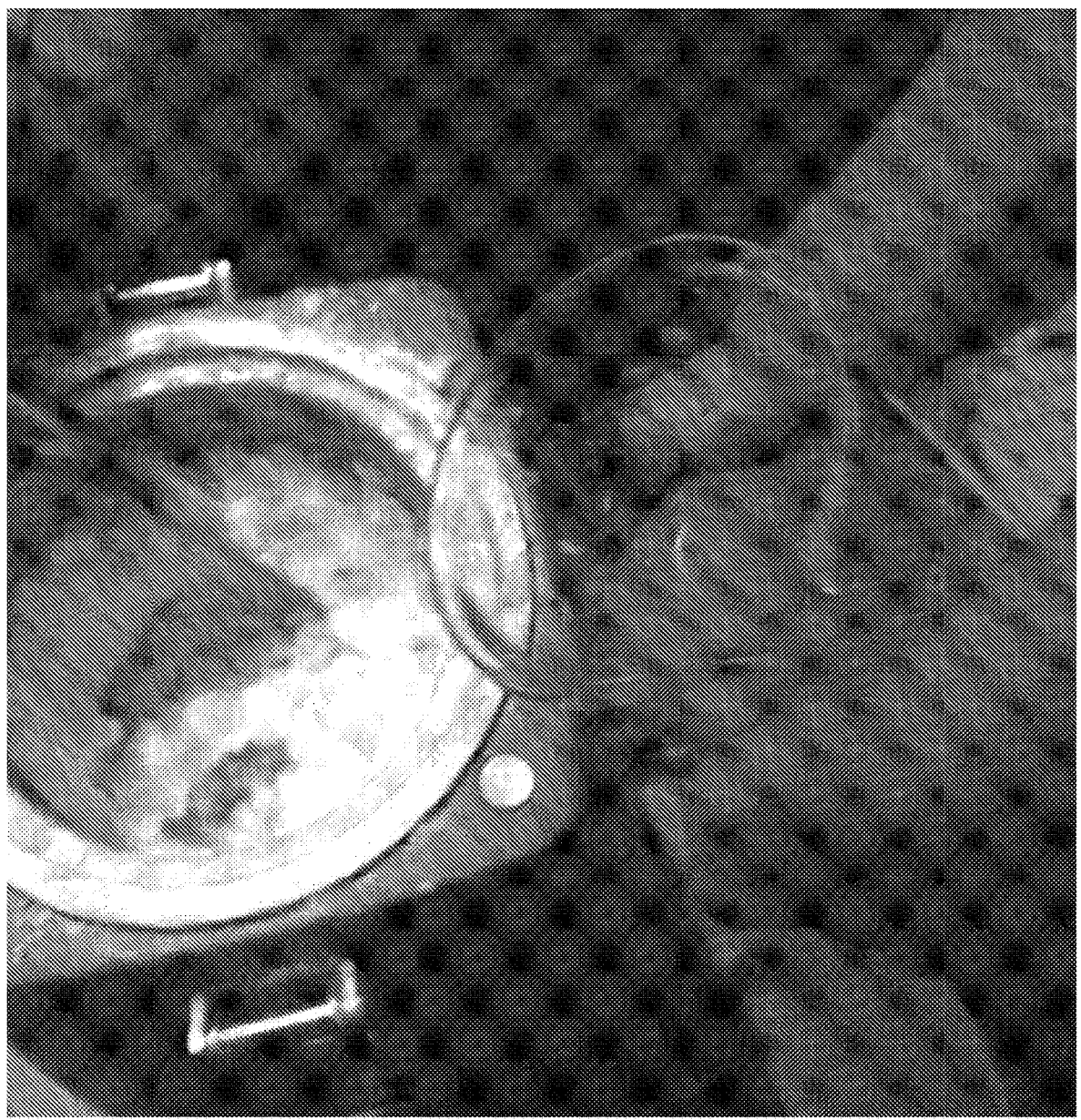
FIG. 18 depicts the creation of a slurry using a benchtop analytical mill according to an embodiment of the invention.

In step S106, the ice is processed into smaller pieces. A variety of techniques and devices can be utilized to reduce the ice size including a blade grinder (e.g., a blender, a food processor, and the like) that have rotating blades, an ice crusher, an ice shaver, a mill, or other suitable device. Suitable blade grinders are available under the WARING® trademark from Conair Corporation of Stamford, Conn. Suitable ice crushers and ice shavers are available under the CLAWSON™ trademark from the Clawson Machine Division of Technology General Corp. of Franklin, N.J. and under the SEMCO™ trademark from Semco Inc. of Pharr, Tex. Suitable mills include the benchtop analytical mill available from Cole-Parmer of Vernon Hills, Ill. and depicted in FIG. 18 and can be utilized to mill either ice or dry ice. In still another embodiment, ice particles can be formed by grinding/milling ice between surfaces (e.g., discs or screens) rotating in opposite directions. In yet another embodiment, shock waves, vibration (e.g., ultrasonic vibration), and/or thermal shock (e.g., from lasers or steam jets) can be used to fracture the ice. In still other embodiments, the ice (and any additives) can be placed in a bag and struck repeatedly with a mallet or other implement.

In step S108, one or more additives (e.g., glycerol) are added to crushed ice (and any previously added additives).

In one example of this method, ice can be scraped at −80° C. into a biocompatible liquid cooled to 1° C. above the biocompatible liquid's freezing point. A surfactant cooled to 20° C. is then added and the resulting slurry is stirred vigorously.

Figure 2:
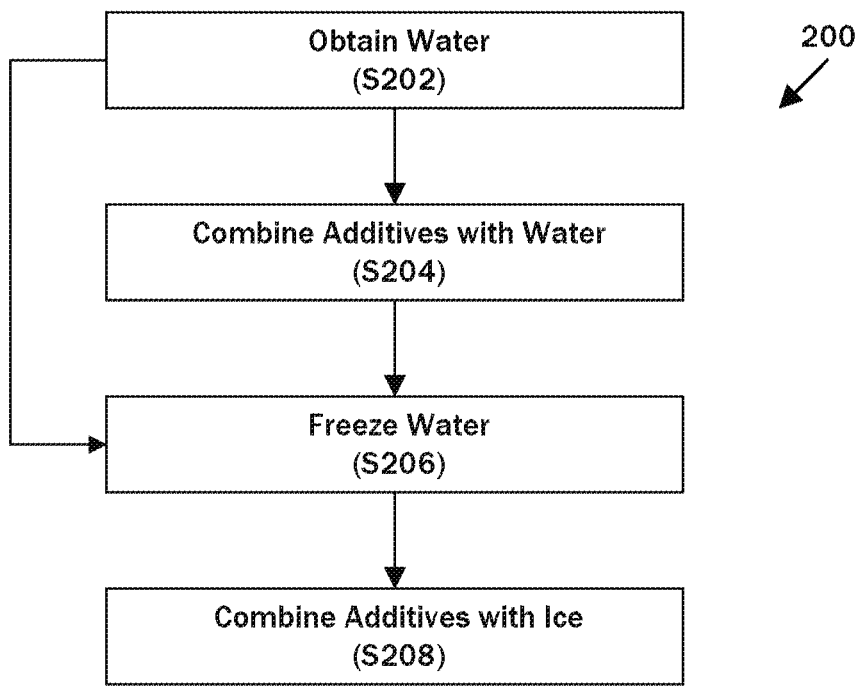
FIG. 2 depicts a method of preparing a slurry according to an embodiment of the invention.

FIG. 2 depicts another exemplary method 200 of preparing a slurry.

In step S202, sterile water is obtained. Sterile water is available from a variety of sources including Hospira, Inc. of Lake Forest, Ill.

In step S204, one or more additives are optionally combined with the sterile water prior to processing.

In step S206, the water (and any additives) are frozen. A variety of techniques and devices can be utilized to freeze the water.

Figure 3:
FIG. 3 depicts an experimental prototype for generating slurries according to an embodiment of the invention.

One example is an ice cream maker that utilizes a moving element (either a paddle or a rotating vessel) to generate small ice crystals. An experimental prototype using a household ice cream maker is depicted in FIG. 3.

Figure 4:
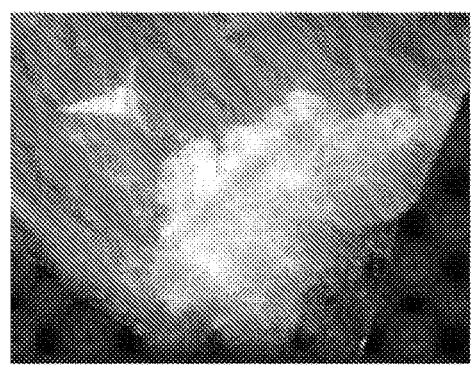
FIG. 4 depicts an example of ice produced by introducing droplets generated by an ultrasonic humidifier into a dry ice environment according to an embodiment of the invention.

In another embodiment, small droplets of water (and optionally additives) are formed and then frozen. Suitable devices for forming small droplets of water include atomizers, injectors, ejectors, aspirators, Venturi pumps, nebulizers, humidifiers, ultrasonic humidifiers, and the like. The generated water droplets can be introduced into a cold environment that can be achieved, for example, using dry ice. An example of ice produced by introducing droplets generated by an ultrasonic humidifier into a dry ice environment is depicted in FIG. 4.

Figure 5:
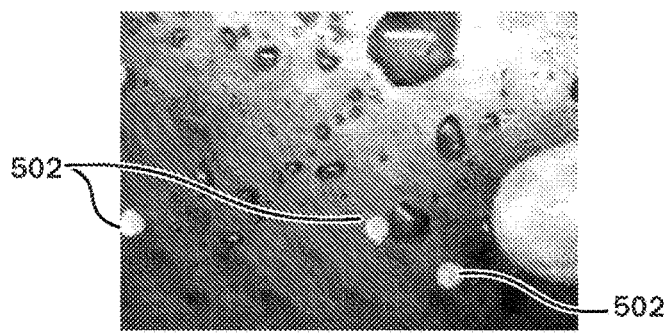
FIG. 5 depicts ice balls harvested using liquid nitrogen according to an embodiment of the invention.

In still another embodiment, small droplets of water (and optionally additives) are dropped into liquid nitrogen then harvested. Ice balls 502 harvested using this technique are depicted in FIG. 5. This process can be automated through the use of a microdropper such as those available from microdrop Technologies GmbH of Norderstedt, Germany.

In still another embodiment, the slurry components can be provided pre-mixed liquid in a bag (e.g., an intravenous fluid bag and like) and then frozen within the bag under continuous or intermittent agitation, e.g., by shock waves, vibration (e.g., ultrasonic vibration), thermal shock (e.g., from lasers, steam jets), and the like to produce a slurry within the bag that can then be injected. This approach advantageously provides a "closed" system for creation of slurries to promote sterility.

Figure 31:
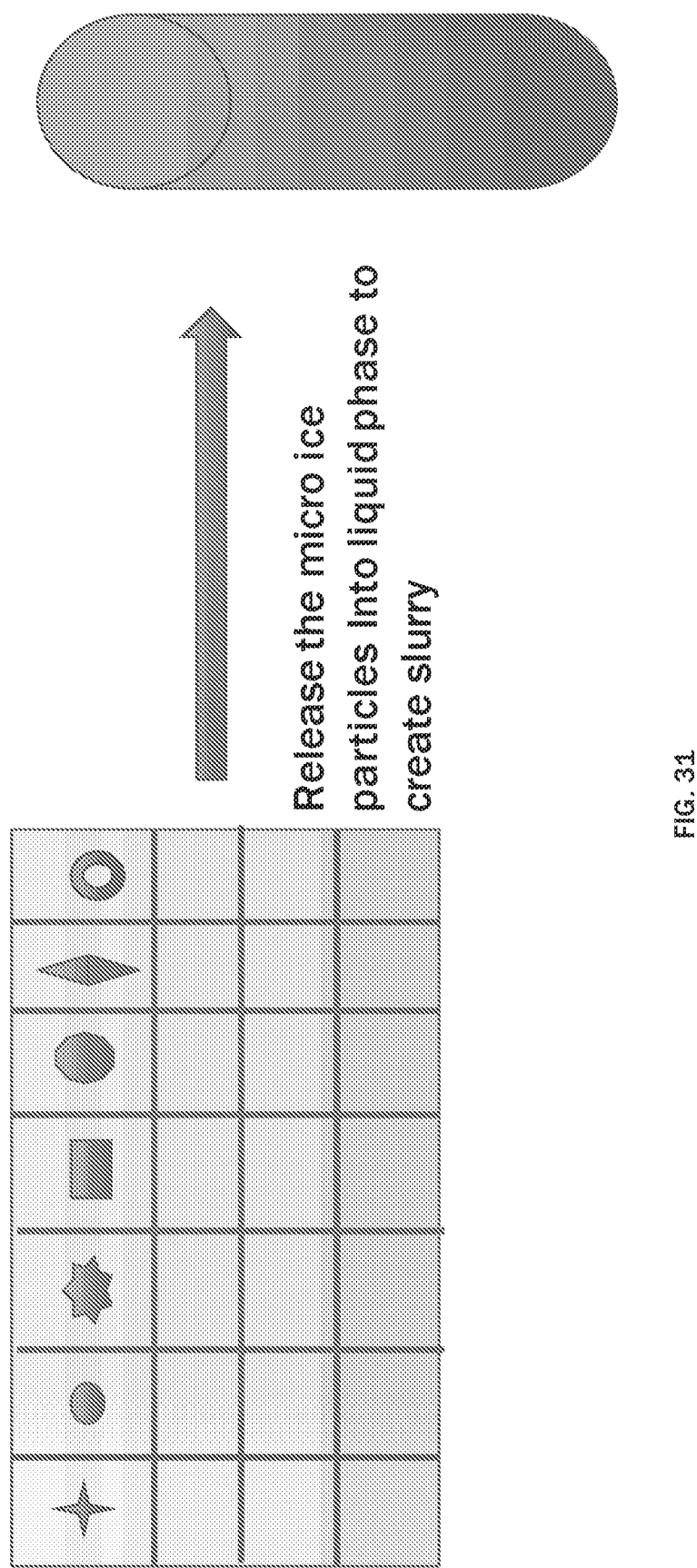
FIG. 31 depicts a tray for molding micro ice particles and a micro ice particle that can be formed from such a tray according to an embodiment of the invention.

In still another embodiment, a plurality of ice particles can be formed in a sub-millimeter (e.g., having a largest cross-sectional dimension of about 0.1 mm or less) or micro-scale casting mold as depicted in FIG. 31. The casting mold can be fabricated through molding, negative molding, 3D printing, additive manufacturing, machining, and the like to define receptacles of a variety of shapes and can be fabricated from a variety of materials such as polymers, plastics, elastomers, silicone, silicon, metals, and the like. The tray can be provided pre-loaded with ice particles or can be loaded with water and frozen in a lab. The tray can flex to release the ice particles into a liquid component to form a slurry.

The casting can be performed by rapid cooling of the casting mold while in contact with liquid water or flowing of liquid water over or through the cold casting material, during which ice forms within casts. Ice particles can be removed from the casts by deformation of the casting material using mechanical strain, stress waves, or shock waves. Ice particles can be removed from the casts by partial melting from an external or internal energy source. Ice particles can be removed or aided to be removed from the casts by centripetal force, e.g., by centrifugation. For example, the casting mold can be rapidly rotated while cooled and periodically supplied with water in order to create small ice particles near the mold surface that are thrown off by centripetal force into a cold environment for collection.

Slurry Storage and Further Processing

Both the slurries described herein and precursor ice particles can be stable for years if held at stable humidity and temperature below the freezing point of the solution or the ice particles. In order to guard against growth or agglomeration of ice crystals, it is preferable to store the slurry at a stable temperature below the temperature for intended use and allow for partial melting of the slurry to reach the desired injection temperature prior to use. Partial melting can be achieved by warming of the slurry (e.g., by exposure of a vessel containing the slurry to ambient conditions or by actively applying an energy source) or introducing additional solute (e.g., glycerin).

Various techniques can be employed to prevent or minimize sublimation of either precursor ice particles or slurries during storage, transport, and/or handling. For example, ice particles can be coated with a surfactant that acts as a barrier to sublimation and reduces friction between ice particles. Additionally or alternatively, the ice particles and/or slurries can be stored under elevated pressure (e.g., above water's triple point).

Either method described above can be performed by a single actor at a single location at a single time or can be performed by one or more actors at one or more locations at one or more times. For example, small stable ice particles can be packaged and shipped using standard cold shipping methods and stored in a standard freezer (e.g., at −20° C.). The ice particles can be combined with one or more additional additives in the clinic shortly or immediately prior to injection. As discussed herein in greater detail, the additives can, for example, be biocompatible solutions, contain a biocompatible surfactant such as glycerol, and be precooled (e.g., to a temperature approximating the desired temperature of the slurry at the time of injection).

The additives can be added through a variety of methods. In one embodiment, the ice particles are stored in a container such as a plastic bag such as those commonly used to store intravenous (IV) fluid and the additive is injected, pumped, or allowed to flow by gravity into the ice particles. In other embodiments, the additive is poured over the ice particles. In still another embodiment, the additive is provided in frangible or burst pouch within the same container as the ice particles. This frangible or burst pouch can be squeezed to rupture the pouch and combine the additive and the ice particles at the desired time.

Once the ice particles and the additives are mixed de novo at the point of care or pre-mixed slurries are removed from a freezer, the temperature is preferably monitored to either maintain or achieve a desired temperature. For example, the slurry may need to rise to a desired temperature, but it may be preferred that the slurry does not rise significantly beyond a desired temperature. Various thermometers, thermocouples, and other temperature measuring devices can be used to measure the temperature of the slurry. These measurements can be internal or external to the container holding the slurry. In one embodiment, a liquid crystal thermometer is applied to the outside of the container (e.g., an IV bag) holding the slurry. Suitable liquid crystal thermometers capable of measuring temperatures between −30° C. to 0° C. are available under Part No. 427-1 from Telatemp Corporation of Anaheim, Calif. In another embodiment, an additive in either the slurry or the container holding the slurry can change color to indicate an appropriate and/or inappropriate temperature. Similarly, a temperature monitor can be used to indicate inappropriate storage or transport conditions for the slurry.

Slurry Delivery

The injectable slurry can be introduced using various parenteral delivery systems and techniques including gravity flow, injection through a syringe, a cannula, a catheter, tubing, and/or a pump, and the like. A control device can control the flow rate, volume, and or pressure of the injected slurry in order to extract a desired amount of heat from tissue adjacent to the injection site.

Optionally, an imaging technique such as ultrasound, magnetic resonance, x-ray, and the like can be utilized to verify the proper positioning of the injection device and/or the slurry. In particular, ice is a very strong reflector of ultrasound, while lipid rich cells are poor reflectors of ultrasound. Ultrasound imaging is a convenient "bedside" imaging modality with sufficient contrast and depth of imaging to guide and/or monitor administration of the slurry.

Therapeutic Applications of Injectable Slurries

The injectable slurries described herein can be utilized to target all tissue types including, but not limited to, connective, epithelial, neural, joint, cardiac, adipose, hepatic, renal, vascular, cutaneous, and muscle tissues. The injectable slurry advantageously can focus a cooling effect direct at the site of the targeted tissue without the challenges of diffusion of heat or perfusion tissue.

Figure 6:
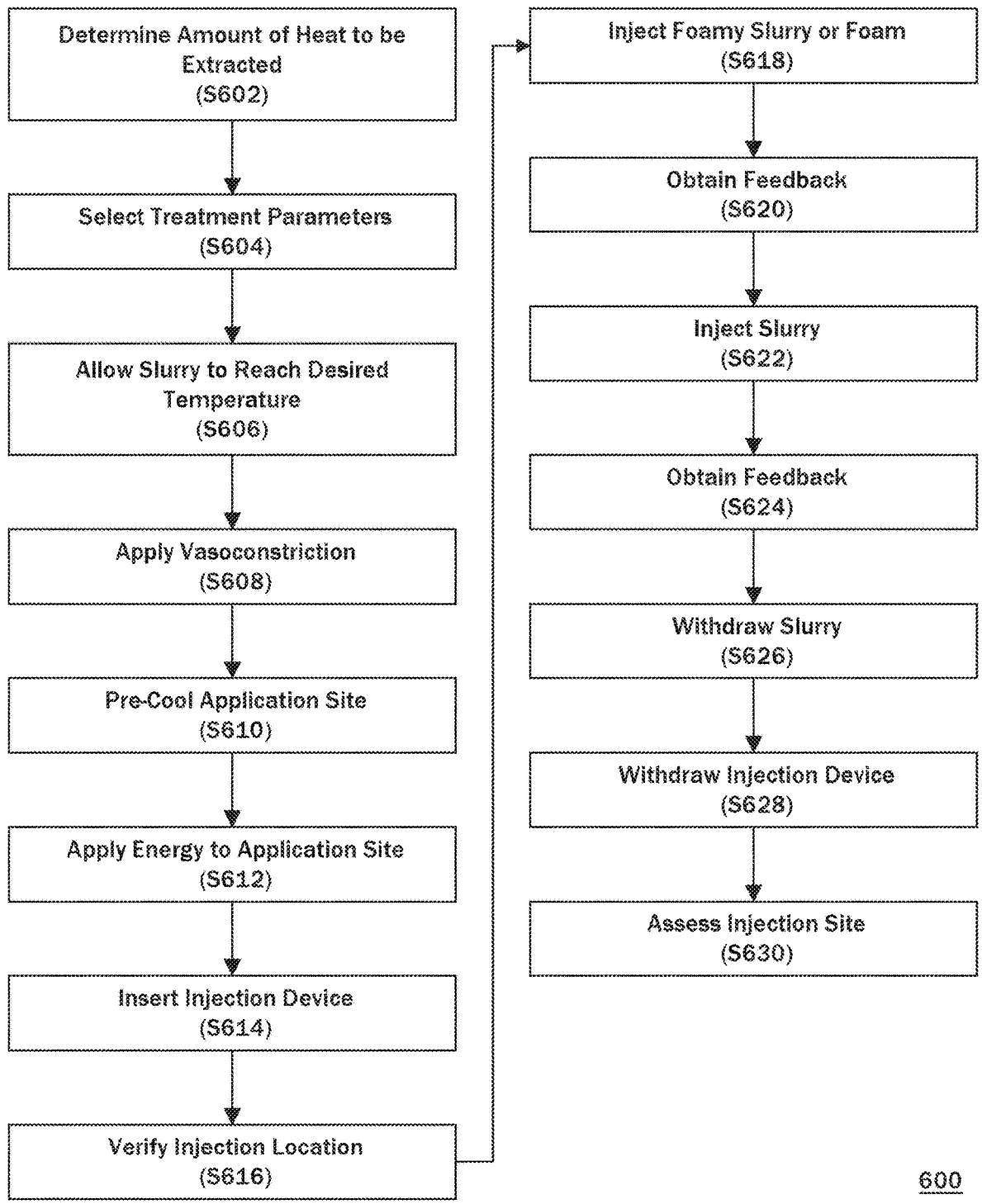
FIG. 6 depicts a general method of treatment using injectable slurries according to an embodiment of the invention.

Referring now to FIG. 6, a general method of treatment 600 using injectable slurries is provided. Although depicted in a linear manner, step(s) can be omitted, repeated, or executed in various orders.

In step S602, the amount of heat to be extracted is determined. The amount of heat to be extracted can be routine and predictable, particularly for treatment of small structures such as nerves and can be specified apriori, e.g., as part of approval of a medical device or procedure, as part of the instruction manual for a medical device, and/or as a preset control parameter in a medical device. In other embodiments, the amount of heat to be extracted can depend on the amount of tissue to be treated, the location of the treatment site, and other attributes of the subject.

In step S604, the treatment parameters are selected. Treatment parameters can include the composition of the slurry (e.g., the ice content and additive content) and the temperature, which together (particularly the ice content) determine the cooling power of the slurry. (The additive content largely influences the temperature of the slurry.) Exemplary ice content and additive content is discussed herein. Exemplary temperatures of the slurry include about +10° C., about +9° C., about +8° C., about +7° C., about +6° C., about +5° C., about +4° C., about +3° C., about +2° C., about +1° C., about 0° C., about −1° C., about 2° C., about −3° C., about −4° C., about 5° C., about −6° C., about 7° C., about 8° C., about 9° C., about 10° C., about 11° C., about 12° C., about 13° C., about 14° C., about 15° C., between about 15° C. and about 25° C., between about 25° C. and about 50° C., between about 50° C. and about 75° C., and the like.

Without being bound by theory, Applicant notes that heat of fusion for lipids is about half of the heat of fusion for water and believes that about 2 units of fat volume can be treated with about 1 unit of slurry volume. It may be desirable to be conservative in the amount of slurry injected, particularly when the treatment site is proximate to nerves, blood vessels, organs, and the like.

In step S606, the slurry is optionally allowed to reach the desired temperature. This can be achieved by allowing the slurry to sit at room temperature or in a controlled temperature environment until its temperature rises to the desired temperature. The slurry can be optionally be stirred or agitated to promote an even temperature distribution. The slurry can optionally be placed in an insulated container to preserve the slurry at the desired temperature. Likewise, the catheters, needles, and/or tubing used to deliver the slurry to the subject can optionally be insulated (e.g., with dead-air space or rubbers such as neoprene) to minimize temperature rise.

In step S608, vasoconstriction is optionally applied, e.g., through physical means such as suction or pressure or chemical means such as epinephrine injections.

In step S610, the application site is optionally pre-cooled to minimize melting of the slurry upon injection. In one embodiment, one or more thermoelectric (Peltier) cooling devices can be used to pre-cool tissue to a desired temperature prior to injection of a slurry. Suitable thermoelectric coolers are available from TE Technology, Inc. of Traverse City, Mich. and Quanta Aesthetic Lasers USA of Englewood, Colo.

In step S612, one or more cryoprotectant approaches can optionally be employed.

For example, energy can be applied to tissue adjacent to the target tissue in order to protect the adjacent tissue from undesired cooling and/or enable more aggressive cooling of the target tissue. Energy can be applied simultaneous with the slurry, in an oscillating manner, in response to feedback, and the like. Suitable energy sources include radiofrequency (RF) energy generating units that can be adapted, configured, and/or programmed to generate monopolar, bipolar, capacitively-coupled, and/or conductively-coupled RF energy. The RF energy can have a frequency between about 0.3 MHz and about 100 MHz. Other suitable energy sources include coherent light sources, incoherent light sources, heated fluid sources, resistive (Ohmic) heaters, microwave generators (e.g., producing frequencies between about 915 MHz and about 2.45 GHz), and ultrasound generators (e.g., producing frequencies between about 300 KHZ and about 3 GHz).

In another example, one or more cryoprotectants (e.g., glycerol, propylene glycol, and the like) can be applied to protect non-lipid-rich tissue from cold-induced injury. The cryoprotectant can be applied topically to the epidermis and/or can be injected into a desired region.

In step S614, an injection device is inserted into the subject. As discussed herein, suitable injection devices include hypodermic needles, cannulas, catheters, and the like. The location and depth of insertion can vary to reflect the target region. For example, the injection device can be inserted to an appropriate depth for parenteral, subcutaneous, intramuscular, or interstitial injections.

In step S616, the location of the injection can be verified, e.g., through ultrasonic or x-ray imaging. Alternatively, the slurry can be administered through a "blind" injection.

In step S618, a foamy slurry or biocompatible foam is optionally injected as described herein to insulate a later injected slurry.

In step S620, feedback about the injection is obtained. Feedback can include additional imaging of the slurry, resistance to further injection, input from the patient (particularly when the slurry contains an anesthetic), information about the treatment site (e.g., using the feedback devices described in U.S. Pat. Nos. 7,367,341 and 8,840,608) and the like. For example, ice particles in the slurry are radiopaque and can be readily visualized using ultrasound.

In step S622, the slurry is injected. Applicant has found that hand pressure typical of that provided to a syringe is sufficient for injection, but higher mechanical pressure can be used as well. The slurry can be injected in discrete, pre-determined volumes or can be injected until a medical professional determines that the injection should cease, e.g., due to increased pressure or resistance to further injection or having injected a desired volume of slurry.

In step S624, feedback about the injection is obtained.

Figure 30C:
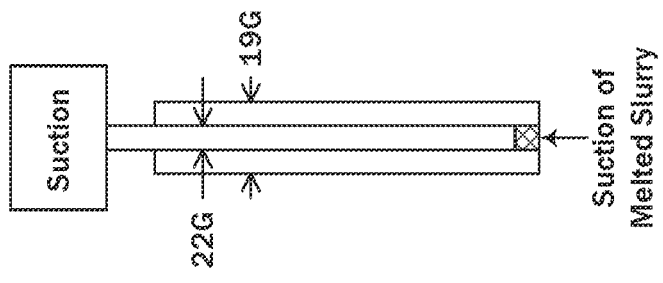
FIGS. 30A, 30B, and 30C depict various structures for removal of melted slurry from an injection site according to an embodiment of the invention.
Figure 30B:
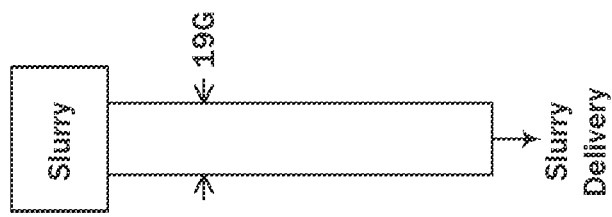
Figure 30A:
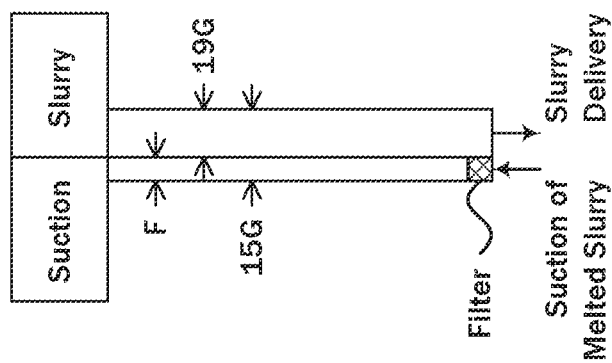

In step S626, the slurry is optionally withdrawn, for example using the methods and devices described in U.S. Patent Application Publication No. 2013/0190744. In many cases, particularly subdermal injections, the slurry will be left in the body to melt and be absorbed. In some embodiments, the suction can be applied concurrently, intermittently, and/or alternatingly to injection of a slurry. For example, a filtered or smaller gauge cannula can be inserted adjacent to or coaxial with an injection device as depicted in FIGS. 30A-30C to remove melted fluid during a procedure while leaving most or all of the ice particles in the injection site. Such an embodiment can be particularly useful for anatomically constrained targets such as nerves in which injecting large volumes of slurry poses challenges.

In step S628, the injection device is removed from the injection site.

In step S630, the injection site is assessed. Assessment can be performed during or after the procedure to assess the effect of the injected slurry. Assessment can be performed by a medical professional and/or by the subject and can include self-reporting, photography, calipers, MRI, as well as the imaging devices described in U.S. Pat. Nos. 7,367,341 and 8,840,608.

All or portions of this method can, but need not, be repeated one or more times for the same injection site and/or target tissue. Multiple injections can be performed in a serial, overlapping, or parallel manner.

In one embodiment, the cryoslurry is injected at a sufficient volume to cause tumescent swelling of the injection site. In another embodiment, a plurality of injection sites each receive an effective amount of slurry for treating a small region of tissue. For example, injections of substantially uniform volumes of slurry can be made in a grid or other pattern.

In some embodiments, serial injections are made within a single treatment session. For example, a first injection can be made to pre-cool the area before a second injection is made to achieve the desired clinical or cosmetic cooling effect. The formulation of these serial injections can vary. For example, the second injection can have a higher or lower cooling power than the first injection.

Cryoneurolysis

A major limitation of medical nerve blocks is their limited duration, which last for hours but not even one day. When somewhat longer relief of pain is needed, constant or repeated infusions of anesthetics are sometimes performed through a needle or through an indwelling catheter, but typically chronic pain is the setting for use of potent analgesics such as opiates, with associated high risk of side effects including addiction.

As discussed in U.S. Provisional Patent Application Ser. No. 62/042,979, filed Aug. 28, 2014, cold and particularly slurries can be used to provide long-term, but reversible inhibition of nerve function. The slurries described herein can provide unprecedented long-lasting reduction or full relief of pain, regardless of its cause.

Methods of the invention can also be used to reduce or eliminate symptoms associated with pain disorders caused by surgery, such as any surgery that makes an incision through the skin and induces pain. This includes thoracic surgery pain (e.g., treatment of incisional surgical pain) caused by thoracic surgery. The slurry can be injected prior, during or after incision.

Methods of the invention can also reduce or eliminate symptoms associated with motor disorders including, but not limited to, hemifacial spasm, laryngospasm and gustatory hyperhidrosis. Methods of the invention can also be used to reduce muscle spasms caused by aberrant nerve firing such as bladder or facial spasms. Methods of the invention can also be used to target motor nerves if prolonged paralysis of a motor nerve is desired.

The solution comprising the slurry can be administered to the peripheral nerves of the subject by injection, infusion or tumescent pumping of the slurry into a nerve or nerves such as peripheral, subcutaneous or autonomic nerves of the subject by injection into a nerve or nerves selected from the group consisting of the cutaneous nerve, trigeminal nerve, ilioinguinal nerve, intercostal nerve, interscalene nerve, supraclavicular nerve, infraclavicular nerve, axillary nerve, pudendal nerve, paravertebral nerve, transverse abdominis nerve, lumbar plexus nerve, femoral nerve, and sciatic nerve.

Methods of the invention can also reduce or eliminate pain associated with a nerve plexus (i.e., a group of intersecting nerves) including but not limited to the cervical plexus that serves the head, neck and shoulders, the brachial plexus that serves the chest, shoulders, arms and hands, the lumbar plexus that serves the back, abdomen, groin, thighs, knees, and calves, the sacral plexus that serves the pelvis, buttocks, genitals, thighs, calves, and feet, the celiac plexus (solar plexus) that serves internal organs, the coccygeal plexus that serves a small region over the coccyx, the Auerbach's plexus that serves the gastrointestinal tract and Meissner's plexus (submucosal plexus) that serves the gastrointestinal tract.

Methods of the invention can also be used for renal sympathetic denervation, which is an emerging therapy for the treatment of severe and/or resistant hypertension.

Injecting a physiological slurry around a particular sensory nerve specifically blocks conduction of that nerve, leading to sensory losses in the entire distribution of the target nerve. Thus, slurry injection can relieve pain and/or itch over a very large region of skin, muscle, joints, and the like that are "served" by a particular target nerve. In previous animal studies, it has been shown that cooling can also block motor nerves. Many nerves in the human body have mixed sensory and motor function. For a mixed nerve, it is often desirable to block sensation but not motor function. (Temporary motor loss may be less of a concern if the subject has already lost motor function, e.g., through amputation.) The anatomy of the peripheral nervous system is such that the motor and sensory nerve fibers become fully separated near the spine. A prolonged and specific block of sensory functions associated with spinal nerve level(s), can be obtained by prolonged block of the sensory nerve root using slurry injection. Slurry injection, with or without ultrasound guidance, to the sensory portion of the peripheral nerve can provide prolonged, specific relief of pain. The step of injection for slurry is similar to injection of medical anesthetic nerve blocks.

It is further noted that the slurries described herein can be utilized to provide long-term, but reversible inhibition of the autonomic sympathetic nerves adjacent to the renal artery to treat hypertension. Other exemplary nerve targets include the sympathetic and parasympathetic nerves.

Cryolipolysis

The slurries described herein can be utilized to provide selective reduction of lipid-rich cells.

Slurry injection provides several improvements over cryolipolysis using external cooling device for subcutaneous fat reduction, due, in part, to the high cooling power of injectable slurries. First, local slurry injection requires only a few minutes of active time to achieve the desired temperatures. Second, slurry injection appears induce the loss of a greater thickness of subcutaneous fat more rapidly (e.g., within 3 weeks to 5 weeks). The greater efficacy probably arises because, unlike surface cooling, slurry extracts heat directly from the target tissue layer, and provides a much faster cooling rate in the target tissue. Third, slurry injections can avoid the epidermis and dermis and approaches that are commercially utilized to detect epidermal temperatures and protect against damage to non-lipid-rich cells. For example and without being bound by theory, it is believed that the dermis and/or epidermis will remain within 15° C. of normal physiological temperature during most subcutaneous slurry injections into adipose tissue. Before, during, and/or after slurry injection into subcutaneous tissue, warming of the skin can be performed, e.g., by application of a warm object or by radiant heating. Fourth, slurry injection is not limited for depth or location of treatment. Slurry can be injected superficially, deeply, or throughout the subcutaneous fat layer and is not limited by the geometries of the subject's skin and the topical applicator. Fifth, slurry injection can be done with greater anatomic accuracy. Physicians are generally very skilled at performing injections, even without ultrasound guidance. With ultrasound guidance, in which the needle cannula or catheter used for injection can be directly seen, slurry can be placed with high accuracy. As noted above, the slurry itself can be visualized by ultrasound, such that the treated tissue is well-defined and known during treatment. Finally, slurries can be administered without the use of large thermoelectric devices used in commercial cryolipolysis systems.

Slurry injections can also quickly numb the nerves adjacent to the treatment site(s), potentially eliminating or reducing the use of anesthesia used in commercial cryolipolysis procedures.

Without being bound by theory, it is believed that cryolipolysis can be achieved through injections of slurries at temperatures of about +5° C. and lower. Without being bound by theory, it is believed that higher ice content slurries will be most effective in extracting sufficient heat to achieve cryolipolysis in clinically and/or cosmetically significant numbers of adipose cells. For example, slurries having at least about 50% (±30%) ice by weight may be preferred. In order to improve the injectability of slurry and the ability of slurry to infiltrate subcutaneous adipose tissue, chemical (e.g., freezing point depressants) and thermal (e.g., warmer coolant) techniques can be used to make any dendritic shaped ice particles more globular. Prior to injection of slurry, addition of a biocompatible exothermic solute may be added to further decrease the temperature of slurry. In some embodiments, the slurry includes an effective amount of a lipolytic agent such as those described herein.

The amount of slurry and/or the slurry ice content to be injected can be calculated and calibrated to produce a desired amount of cryolipolysis. Without being bound by theory, it is believed that cooling effects of slurries can be tightly controlled such that two slurries having the same composition and physical characteristics will produce substantially the same amount of cryolipolysis if injected into the same location under the same physiological conditions.

Without being bound by theory, it is believed that the slurries described herein can be utilized to achieve cooling rates above about 2° C. per minute. For example, the cooling rate can be greater than about 10° C. per minute, greater than about 20° C. per minute, greater than about 30° C. per minute, greater than about 40° C. per minute, greater than about 50° C. per minute, greater than about 60° C. per minute, greater than about 70° C. per minute, greater than about 80° C. per minute, greater than about 90° C. per minute, greater than about 100° C. per minute, greater than about 110° C. per minute, greater than about 120° C. per minute, and the like. For example, Applicant has achieved cooling rates of about −117° C. per minute in tissue in contact with slurry and about and −26° C. per minute in adjacent adipose tissue. Cryolipolysis via slurry injection can be applied to variety of regions in which fat reduction is desired for medical and/or cosmetic reasons. Exemplary regions include the abdomen, flanks (also known as "love handles"), buttocks, thighs, arms, neck, chin (e.g., treatment of submental fullness also known as a "double chin"), and the like.

Treatment of Obstructive Sleep Apnea

Sleep apnea is due to upper airway obstruction during sleep. Sleep apnea causes poor quality sleep, wakening, organ damage from hypoxia (including myocardial infarctions, stroke, and cumulative brain injury), and is a frequent cause of death in obese individuals. The prevalence of sleep apnea has been steadily increasing in the US due to obesity. Present treatments are generally aimed at reducing the degree of obesity (through diet, exercise, medications, and/or surgery) and at keeping the airway open during sleep. Continuous positive airway pressure (CPAP) helps to keep the airway patent, but requires wearing a close-fitting mask and pressure apparatus all night. These often fall off during sleep, leak, or are uncomfortable enough that sleep can be disrupted simply by wearing them. Occlusion of the airway is strongly related to the amount of fat located in deep fat pads located at the base of the tongue and along the soft palate and lateral pharynx. Surgical procedures have been developed, for example, to suspend the palate or debride pharyngeal fat, but these ultimately also cause scarring, often fail to open the airway sufficiently, are painful and cause local edema during healing that can precipitate worse sleep apnea, airway obstruction, respiratory distress and death.

Injection of physiological ice slurry into the subglottal, palatal and/or pharyngeal fat is a novel treatment for sleep apnea. Guidance by ultrasound for accurate placement and injection of slurry within the target tissue is also a novel method. These fat compartments are distinct from subcutaneous fat. They can be visualized by ultrasound, as regions of echolucency (low signal) compared with surrounding muscle, fascia and other structures. Slurry with a high ice content is particularly desirable to minimize the volume of injected slurry needed for effective reduction of the target fat. During about 6 weeks after treatment, injection of slurry into the fat will induce gradual reduction in the amount of fat, resulting in improvement or cure of the patient's sleep apnea. The intrinsic selectivity of this treatment for fat is such that adjacent muscle, fascia, salivary gland and other tissues are spared from injury, while reliable reduction of the target fat can be achieved. Unlike surgery, this would be an office procedure performed with little or no anesthesia. Unlike surgery, there would be no scarring because the treatment is intrinsically selective for the lipid-rich adipose tissue causing sleep apnea. The post-treatment pain, inflammation and risk of airway compromise will be less than surgical procedures, because adjacent tissues are not affected. Unlike CPAP, injection of physiological ice slurry provides a permanent improvement and does not interfere with sleep.

Exemplary regions that can be targeted include the anterolateral upper airway, pharyngeal fat pads (for example, fatty deposits in the laryngopharynx, nasopharynx, oropharynx, and palatopharynx), parapharyngeal fat pads (for example, fatty deposits in the retropalatal and retroglossal regions), fat located within the tongue (e.g., within the posterior tongue), and soft palate. Without being bound by theory, it is also believed that treatment with the slurries described herein will thicken septa and tighten skin, which can also reduce the tendency of the airway to collapse.

Injections can be made through the mouth or through the neck in order to best target a particular region of fat while avoiding adjacent nerves, blood vessels, and other structures. The amount of fat removed per treatment can be adjusted by adjusting the volume and/or ice content of the injected slurry, and precise location of the fat removed can be adjusted by location of the injection(s). Multiple courses of treatment that each remove a small volume of fat from fat located in the tongue, neck, palate, pharynx and/or tonsil may be preferred in order to minimize temporary airway constriction due to the added slurry volume.

This novel method for treatment of sleep apnea can have a major impact on health care, including reducing the morbidity, heart attacks, stroke and death associated with obesity.

Treatment of Spinal Cord Lipomas and Lipomyelomeningocele

Spinal cord lipomas and lipomyelomeningocele are both associated with abnormal fat accumulation in and around the spinal cord. A spinal cord lipoma is fat within the normally positioned spinal cord without any skin or bony abnormalities. These lesions are most commonly located within the thoracic spinal cord. Although rare, these lesions can cause severe morbidity. They may be symptomatic and appear most often in adults. Patients can present with spinal cord compression that can cause numbness and tingling, weakness, difficulty with urinating or bowel movements, incontinence, and stiffness of the extremities.

The current treatment for symptomatic lipomas around the spinal cord the treatment of choice is a laminectomy to gain access to the spinal cord. The goal of surgery is to reduce the size of the lipoma, not total removal of the fat. No other treatment method is recommended.

Embodiments of the invention utilize injection of cold slurry to specifically target the spinal lipomas without the need to do laminectomy as cold slurry could be directly injected into the lipoma through a needle. With the use of ultrasound guidance, the lipoma can be located and specifically destroyed via a cold slurry injection. This novel method of treating lipomas will reduce the morbidity associated with surgical procedures The slurry injection method of treatment can be used for any lipomas around the nerves including peripheral nerves. Lipomas may also grow near or surrounding important peripheral nerves. Therefore, their removal can cause nerve injury and possible paralysis. Common locations include the neck, buttock, and forearm. Again, injection of the slurry into the lipomas to selectively target them will reduce the need for surgery.

Lipomyelomeningocele (LMM) is a common and severe closed neural tube defect in children. Lipomyelomeningocele lies within the spectrum of closed neural tube defects. It represents a complex disorder that may present with neurological deficits secondary to the inherent tethered cord. This is a lesion present at birth that is commonly associated with spina bifida (congenital failure of the spinal bones to close). The condition is associated with abnormal fat accumulation that starts below the skin and extends through the bony opening to the spinal cord. These lesions become evident within the first few months to years of life and affect females more than males in a 1.5 to 1 ratio. More than 90 percent of patients will have an obvious soft tissue swelling over the spine in the lower back. These lesions are covered by skin and are not painful. Patients may lose neurological function within the first few weeks after birth, but more typically, function deteriorates over a period of months to years. Neurological symptoms usually include weakness and bladder and bowel incontinence. The weakness can be symmetrical or asymmetrical and can result in atrophy of the lower extremities. In older adolescents and adults, pain may be the driving force to bring the patient to a doctor. The pain may radiate and be difficult to describe. Back mobility may be limited. Surgery is the treatment of choice whenever possible, but most cases are inoperable. The goals of surgery are to release the attachment of the fat (tethering) to the spinal cord and reduce the bulk of the fatty tumor. With surgery, 19 percent of patients will improve, 75 percent will be unchanged, and 6 percent will worsen. A fat-selective, minimally invasive treatment is likely to produce safety and efficacy that are superior to surgery, and would make it possible to treat inoperable cases.

Injection of cold slurry can specifically target the lipoma and decrease its size, thus preventing neurological damage associated with their growth. The injection needle can be guided by ultrasound or MRI (magnetic resonance imaging) for accurate placement and injection of slurry within the target tissue. MRI can provide an accurate pre-treatment "map" of the local anatomy including bones, spinal cord and the target lipomeningiocele. The use of slurry to treat LMM will offer a novel, less morbid and lifesaving treatment for these pediatric patients.

Breast Reduction

Pseudogynecomastia or lipomastia in males is due to the presence of fat deposits in the breast. This condition is more prevalent in men with aging, overweight, certain drugs, or exposure to estrogens including dietary sources. Currently, surgical removal is the preferred treatment. Applicant believes that injection of embodiments of the slurries described herein into the excess fat around the breast tissue will be less invasive technique with less morbidity.

Additionally, slurry injections can be used for female breast reduction procedures, particularly, as a substitute to liposuction-only techniques indicated for minor-to-moderate volume reduction. The increase in connective tissue discussed in greater detail herein also can provide a firming and lifting effect to either the breast or pectoral region.

Treatment of Epicardial and Pericardial Fat

The slurries described herein can be utilized to treat epicardial and/or pericardial fat. Such treatments can be used for the prevention of coronary artery disease and coronary atherosclerosis, prevention and treatment of atrial fibrillation and atrial tachyarrhythmias, and prevention and treatment of ventricular tachyarrhythmia.

Thoracic fat includes extra-pericardial (outside the visceral pericardium) and intra-pericardial (inside the visceral pericardium) adipose tissue. It is called ectopic adipose tissue although it is a normal anatomical structure. Intra-pericardial adipose tissue, which is predominantly composed of epicardial and pericoronary adipose tissue, has a significant role in cardiovascular system function. The epicardial fat is located between the myocardium and visceral pericardium and the pericardial fat, is located outside the visceral pericardium and on the external surface of the parietal pericardium. Epicardial and pericardial fat are embryologically different.

Recent studies have suggested that increased epicardial fat could be an important risk factor for cardiac disease. It secretes pro-inflammatory cytokines that can lead to development of coronary artery disease (CAD). In humans, there is a positive association between epicardial adipose tissue (EAT) volume and coronary atherosclerosis burden. Prospective case-cohort and case-control studies have shown that EAT volume predicted future CAD events and myocardial ischemia. These finding suggest that EAT might contribute locally to coronary atherogenesis. In swine models, it has been shown that selective surgical excision of adipose tissue in direct contiguity with one of the epicardial coronary arteries attenuated the progression of atherosclerosis, thus suggesting that removal of epicardial fat can serve as a preventive measure for CAD.

Pericardial fat may represent an important risk factor for cardiovascular disease because of its unique properties and its proximity to cardiac structures. Pericardial fat has been associated with an adverse cardiovascular risk profile, coronary artery calcium, and prevalent cardiovascular disease in several studies. Pericardial fat volume (PFV) has recently been reported to be strongly associated with CAD severity and presence. Pericardial fat has also been associated with common arrhythmias, such as atrial fibrillation (AF). AF is the most common cardiac arrhythmia in clinical practice and is associated with major morbidity and mortality. AF prevalence has been projected to increase in the coming decades and is expected to affect over 7.5 million Americans by the year 2050. Pericardial fat has also been associated with ventricular tachyarrhythmia and mortality from systolic heart failure.

The slurries described herein can be utilized to treat epicardial and/or pericardial fat by injection of slurry into and/or around pericardial and/or epicardial fat during cardiac surgery. Additionally or alternatively, computed tomography (CT) or ultrasound (US) imaging can be utilized to guide a needle into the pericardial and/or epicardial fat for slurry injections. Injections can also be performed under direct vision of video-assisted thoracoscopic surgery.

In still another embodiment, slurry can be injected into the pericardium with or without the use of ultrasound guidance. The main approaches to accessing the pericardium are subcostal, parasternal and apical. In one example, pericardiocentesis can be performed using a long, thin needle or catheter (e.g., 7-9 cm, 18 G). At normal physiologic conditions, there is less than 50 ml of fluid in the pericardial space. In acute conditions, this space can hold a volume of up to 200 ml without hemodynamic compromise and can hold more than 500 ml if fluid accumulates chronically. Hence, one could postulate that there is a safe therapeutic window in which volumes of slurry could be injected and either removed from the pericardium or left in the pericardium.

Treatment of Visceral Fat

The slurries described herein can be utilized to provide selective reduction of lipid rich cells such as visceral fat in accordance with the methods described in U.S. Patent Application Publication No. 2013/0190744. For example, the slurries described herein can be introduced into the abdominal and/or peritoneal cavity. Such injections can reduce lipid-rich cells in structures such as the omentum and the perinephrium and regions such the perigonadal, retroperitoneal, and mesenteric regions of the body.

Non-Selective Cryoablation

In addition to selectively targeting lipid-rich cells in the methods discussed above, embodiments of the slurries described herein can be utilized in traditional cryoablation techniques including prostate cryoablation, renal cryoablation, cardiac cryoablation, fibroadenoma cryoablation, and the like. Traditional cryoablation is performed with various invasive probe devices at very low temperatures, typically about −30° C. to − C. Tissue destruction is not selective for lipid-rich cells at these temperatures. An injected slurry with high osmolality and high ice content can achieve temperatures below −20° C., and could be used for these non-selective procedures, with some advantages over existing cryogen probe devices.

Connective Tissue Enhancement

Selective loss of fat produces an increase in the relative amount of connective tissue at and/or near the site of slurry injection. By affecting primarily the adipocytes and removing fat, the connective tissue septae that supported the fat remain and become thicker. This is clearly seen in both histology and gross tissue images from the swine experiments. Fat is generally mobile and weakly supportive. The relative increase in connective tissue after treatment provides better support for the overlying skin. After cryolipolysis treatments, Applicant observed clinically that laxity (sagging) improves dramatically.

In other words, adipose tissue is a connective tissue, but it tends to become lax. Slurry injection removes the adipocytes, but preserves and stimulates the septae, resulting in less laxity and greater mechanical support. Histology and also gross images such as FIGS. 16A and 16B clearly show that slurry injection into adipose tissue causes this change.

This effect provides an added benefit to procedures such as cryolipolysis, breast reduction, and treatment of obstructive sleep apnea, pseudogynecomastia, and lipomastia, but can be used for the sole purpose of skin tightening.

Pelvic Floor Strengthening and/or Tightening

The pelvic floor is the supportive apparatus that holds the pelvic organs in place. Pelvic floor dysfunction (e.g., due to pelvic floor laxity) can cause abnormal defecation, urinary dysfunction, prolapse, pain, and sexual dysfunction.

The slurries and methods described herein can be applied to strengthen and/or tighten the pelvic floor. For example, slurries can be injected (e.g., through transurethral, transvaginally, or transperitoneal injections) adjacent to the pelvic floor to induce tightening and/or thickening of the pelvic floor in order to better support one or more pelvic organs.

Treatment of Urinary Incontinence

In a recent survey among women aged 25-84 in the United States, an estimated 15% report experiencing stress incontinence and 13% report experiencing urge incontinence/ "overactive bladder." These two etiologies of incontinence are due to separate mechanisms, though both mechanisms may be experienced by a single patient.

Stress incontinence is the most common type of incontinence in younger women, often from urethral hypermobility, which is due to insufficient support from the pelvic floor. This lack of support is due to a loss of connective tissue. This loss of support is also associated with other conditions such as pelvic organ prolapse and problems with defecation (both constipation and incontinence). Administration of the slurries described herein in the pelvic area can thicken the connective tissue and thereby increase the support of the pelvic floor. Thus, in one embodiment, the invention provides a method for treating stress urinary incontinence in a subject in need thereof. The method comprises administering to the connective tissue of the pelvic floor of the subject a therapeutically effective amount of a slurry described herein.

In contrast, urgency incontinence is due to overactivity of the detrusor muscle. The slurries described herein can be used as an injectable therapy to inhibit neural input to the bladder.

Strengthening of Abdominal Wall

Abdominal laxity can lead to hernias or cosmetically bothersome abdominal protrusions.

The slurries described herein can be used to cause skin tightening and/or tightening of the fascia supporting the abdominal wall to prevent and/or remedy hernias or abdominal protrusions.

Perivascular and Periadventitial Adipose Tissue

As described herein, the slurries described herein can be utilized to treat cardiovascular diseases associated with epicardial and/or pericardial fat. In some applications, the slurries described herein may be used to target perivascular or periadventitial adipose tissue within the human body for the purpose of modulation of adipose and immune function, as well as, targeted removal to provide treatment of various diseases or clinical states.

Almost all blood vessels are surrounded or embedded in perivascular adipose tissue (PVAT), which represents about 3% of the total body adipose tissue mass. PVAT was initially considered to play primarily mechanistic support for the vasculature but in recent years it has become clear that PVAT plays a critical role for the regulation of vascular/endothelial function in both physiology and pathology. In fact, most arteries prone to the atherosclerosis are all surrounded with PVAT. Anatomically, PVAT is contiguous with adventitial layer of the blood vessel wall, and adipocytes migrating from the PVAT have been detected within the adventitia. PVAT is also called periadventitial adipose tissue, and is shown to also play critical role in vascular remodeling and vascular disease. It is now believed that the crosstalk between PVAT, the adventitia, the endothelial and smooth muscle layers of blood vessels are essential in normal vascular function and are perturbed in diseases such as arterial atherosclerosis, hypertension, arterial aneurysm formation such as aortic aneurysm, arrhythmia, arterial spasm, arterial ulcers. Circumstantial evidence also links PVAT to the pathogenesis of non-atherosclerotic vascular diseases including neoinumal formation, aneurysms, arterial stiffness and vascultis/vasculitic syndromes, such as Takayasu's arteritis, where infiltration and migration of inflamnmatory cells from PVAT into the vascular wall may play a contributory role.

PVAT plays a critical role in the pathogenesis of cardiovascular and other vascular pathologies, in which it has been shown to become dysfunctional with altered cellular composition and molecular characteristics. PVAT dysfunction is characterized by its inflammatory character, oxidative stress, increased production of pro-inflammatory paracrine factors such as resistin, leptin, IL-6, TNF-alpha, MCP-1, RANTES, and decreased production of vasoprotective factors such as adiponectin. The pro-inflammatory factors produced by dysfunctional PVAT initiate and promote inflammatory cell infiltration including macrophages, lymphocytes, dendritic cells, NK cells which propagate the vascular pathology. Local expansion of PVAT has been associated with atherosclerotic plaque formation, vascular calcification, hypertension and aortic abdominal aneurysm.

PVAT inflammation in vascular disease are important in the context of number of cardiovascular disorders including atherosclerosis, hypertension, vascular aneurysms, diabetes and obesity. Inflammatory changes in PVAT's molecular and cellular responses are uniquely different from visceral, subcutaneous and adventitial adipose tissue, highlighting the uniqueness of this adipose tissue compartment. The differences between white, brown and perivascular adipose tissue are highlighted in the publication by Nosalski R, Guzik T J. Perivascular adipose tissue inflammation in vascular disease. *Br J Pharmacol.* October 2017; 174(20):3496-3513.

Cardiovascular disease (CVD) is the leading cause of death worldwide, and atherosclerosis is the pathology that causes most of the cardiovascular events. Morphological, structural and functional alterations of PVAT have been associated with CVD risk factors including atherosclerosis, hypertension, arterial aneurysm and diabetic vasculopathies. Obesity is a major risk factor for CVD. Like other adipose tissue, PVAT increases in size and expands in obesity and becomes dysfunctional, which is characterized by hypoxia, infiltration of immune cells (monocytes, macrophages, lymphocytes and granulocytes), increased production of pro-inflammatory adipokines, cytokines and chemokines. Interestingly, high-fat diet and hypercholesterolemia even without obesity has been shown to increase inflammation in PVAT. This inflammation and dysfunction, propagates to the underlying vessel wall, causing vascular endothelial and smooth muscle cell dysfunction, ultimately contributing to atherosclerosis or vascular disease formation.

Thus, selective targeting of the perivascular and periadventitial adipose tissue with the slurries described herein may serve as a therapy for all the vascular diseases and conditions mentioned herein, including but not limited to all peripheral vascular diseases, coronary artery disease, hypertension, aneurysms, diabetic vasculopathies, arrhythmia, arterial spasm, arterial ulcers, neointimal formation, arterial stiffness, arterial atherosclerosis, arterial aneurysm formation such as aortic aneurysm, arrhythmia, and vasculitis. In addition, there is evidence to link PVAT to the pathogenesis of non-atherosclerotic vascular diseases including neointimal formation, aneurysms, arterial stiffness and vasculitis/vasculitic syndromes.

In general, the slurries described herein may be used to selectively target any vessel in the body that plays a role in vascular disease. For example, PVAT adjacent to one or more of the coronary arteries, femoral arteries, carotid arteries, ascending aorta artery, abdominal aorta, thoracic aorta, and iliac arteries may be targeted with a slurry injection to treat vascular disease. Below selective non-limiting examples are described to provide further motivation for the use of slurries in the treatment of vascular diseases. The non-limiting examples are by no means a limiting list of the applications for which slurry may be used as a treatment for vascular disease.

Atherosclerosis and Peripheral Vascular Disease

The essential role that PVAT plays in inducing inflammation and atherosclerosis was experimentally tested by transplanting pro-inflammatory adipose tissue to the mid-perivascular area of common carotid arteries, which do not normally develop atherosclerosis and showing that it results in atherosclerotic lesions in mouse models. Ohman M K, Luo W, Wang H, et al. Perivascular visceral adipose tissue induces atherosclerosis in apolipoprotein E deficient mice. *Atherosclerosis.* November 2011; 219(1):33-39. A postpartum study of atherosclerotic patients found that PVAT mass was positively correlated with atherosclerotic plaque size. Verhagen S N, Vink A, van der Graaf Y, Visseren F L. Coronary perivascular adipose tissue characteristics are related to atherosclerotic plaque size and composition. A post-mortem study. *Atherosclerosis.* November 2012; 225 (1):99-104.

Adipose tissue is an active endocrine and paracrine organ, which communicates with the arterial vessel wall and can influence the development of atherosclerosis and vascular disease. In the setting of obesity, adipose tissue produces a variety of inflammatory cytokines (or adipokines) that play an essential role in modulating and propagating atherogenesis. In particular, adipose tissue located on the surface of the heart surrounding large coronary arteries (i.e. epicardial perivascular adipose tissue) has been implicated in the pathogenesis of coronary artery disease. Atherosclerotic plaques have been shown to occur predominantly in areas of the coronary arteries that are encased in PVAT, and the severity of these lesions are directly correlated to the volume of epicardial PVAT. Payne G A, Borbouse L, Kumar S, et al. Epicardial perivascular adipose-derived leptin exacerbates coronary endothelial dysfunction in metabolic syndrome via a protein kinase C-beta pathway. *Arterioscler Thromb Vasc Biol.* September 2010; 30(9):1711-1717. In addition, the Framingham Heart Study and Multi-Ethnic Study of Atherosclerosis identified epicardial and pericardial adipose volume as independent risk marker for cardiovascular and coronary heath disease, and the epicaridal PVAT volume was the strongest predictor of coronary artherosclerosis. Greif M, Becker A, von Ziegler F, et al. Pericardial adipose tissue determined by dual source CT is a risk factor for coronary atherosclerosis. *Arterioscler Thromb Vasc Biol.* May 2009; 29(5):781-786.

Epicardial adipose tissue (EAT) around coronary arteries may induce vasocrine or paracrine effects on the adjacent arterial wall to influence atherosclerotic plaque composition, resulting in the development of high-risk plaque. Nerlekar N, Brown A J, Muthalaly R G, et al. Association of Epicardial Adipose Tissue and High-Risk Plaque Characteristics: A Systematic Review and Meta-Analysis. *J Am Heart Assoc.* Aug. 23 2017; 6(8). Recently in a swine model, surgical removal of 1.5 $cm^2$ of EAT around the coronary artery was shown to arrested coronary atherogenesis. McKenney-Drake M L, Rodenbeck S D, Bruning R S, et al. Epicardial Adipose Tissue Removal Potentiates Outward Remodeling and Arrests Coronary Atherogenesis. *Ann Thorac Surg.* May 2017; 103(5):1622-1630. However, surgical removal of epicardial adipose tissue is an invasive procedure with various potential surgery related complications. The slurries described herein may be used to target and remove epicardial adipose around the coronary arteries using a safe and simple slurry injection. For example, the slurries described herein may be used to target epicardial adipose tissue directly surrounding coronary vessels that have atherosclerotic plaques.

Aneurysms

The most widely studied aneurysms are the abdominal aortic aneurysms (AAA), in which inflammation and cellular composition of arterial wall, perivascular and adventitial fat tissue have been shown to play a major role. Inflammatory cell such as macrophages, neutrophils, monocytes, lymphocytes, and inflammatory cytokines such as MCP-1, TNF-alpha, IL-6 have all been shown to be increased in the aortic wall of AAA. Abdul-Hussien H, Hanemaaijer R, Kleemann R, Verhaaren B F, van Bockel J H, Lindeman J H. The pathophysiology of abdominal aortic aneurysm growth: corresponding and discordant inflammatory and proteolytic processes in abdominal aortic and popliteal artery aneurysms. *J Vasc Surg.* June 2010; 51(6):1479-1487. These inflammatory cells have also been observed in PVAT and have clearly been shown to increase susceptibility to AAA formation. Police S B, Thatcher S E, Charnigo R, Daugherty A, Cassis L A. Obesity promotes inflammation in periaortic adipose tissue and angiotensin II-induced abdominal aortic aneurysm formation. *Arterioscler Thromb Vasc Biol*. October 2009; 29(10):1458-1464. More recently it was shown that the abnormal appearance of adipocytes in the vascular wall of aortic aneurysm was strongly associated with AAA rupture, in a rat abdominal aortic aneurysm model. Kugo H, Zaima N, Tanaka H, et al. Pathological Analysis of the Ruptured Vascular Wall of Hypoperfusion-induced Abdominal Aortic Aneurysm Animal Model. *J Oleo Sci*. May 1 2017; 66(5):499-506. The abnormal appearance of adipocytes was also shown in human AAA tissue. Tanaka H, Zaima N, Sasaki T, et al. Imaging Mass Spectrometry Reveals a Unique Distribution of Triglycerides in the Abdominal Aortic Aneurysmal Wall. *J Vasc Res*. 2015; 52(2):127-135. Furthermore, aortic aneurysm (AA) is a disease that involves progressive dilation of the aorta due to weakening of the artery vascular wall due degradation of extracellular matrix collagen and elastin fibers which play an important role in maintaining the integrity and elasticity of the vascular wall. In the study by Kugo, H. et al, it was shown that in the areas of AAA where abnormal appearance of adipocytes was seen in the vessel wall, there was increased MCP-1 protein level, and macrophage infiltration around the adipocytes. Kugo H, Zaima N, Tanaka H, et al. Pathological Analysis of the Ruptured Vascular Wall of Hypoperfusion-induced Abdominal Aortic Aneurysm Animal Model. *J Oleo Sci*. May 1 2017; 66(5):499-506. Electron microscopy showed that the presence of these adipocytes caused decreased collagen in the vascular wall, thus leading to the conclusion that in the vascular wall integrity is decreased in areas around adipocytes compares to that in areas without adipocytes. Id.

In conventional medicine, there is no effective medicine available for inhibiting aneurysm growth or preventing aneurysm rupture. Generally, perivascular and adventitial adipocytes are implicated in many of the common vascular arterial diseases, which lead to aneurysm formation. Thus, treating those areas with slurry injection will not only lead to selective targeting and reduction of abnormal adipocytes but also lead to increase collagen formation, which we have shown to happen in subcutaneous adipose tissue.

Hypertension

Hypertension is associated with activation of renin-angiotensin system (RAS) and increased vascular oxidative stress, which has been shown to start from inflammation within the PVAT, and PVAT/adventitial border. Nosalski R, Guzik T J. Perivascular adipose tissue inflammation in vascular disease. *Br J Pharmacol*. October 2017; 174(20): 3496-3513. During the progression of hypertension, immune cells mainly infiltrate the perivascular fat tissue surrounding large and resistance vessels such as aorta and mesenteric arteries. PVAT has direct influence on the vasoactive and vasodilatory abilities of the artery. Furthermore the non-cholinergic and non-adrenergic neural network also is present within this adipose layer such that both have an influence on vasomotor tone as well. Under normal physiology there is a strict orderly equilibrium of this periarterial neuro-paracrine system, however in obesity, these putative vasodilators release and effect are blunted. The end result of such would be an increase vasomotor tone with tendency to developing clinical hypertension. Thus, targeted removal of perivascular fat with slurry injection may be a treatment for hypertension.

Injection Systems for Using Slurry to Treat Vascular Disease

Figure 7:
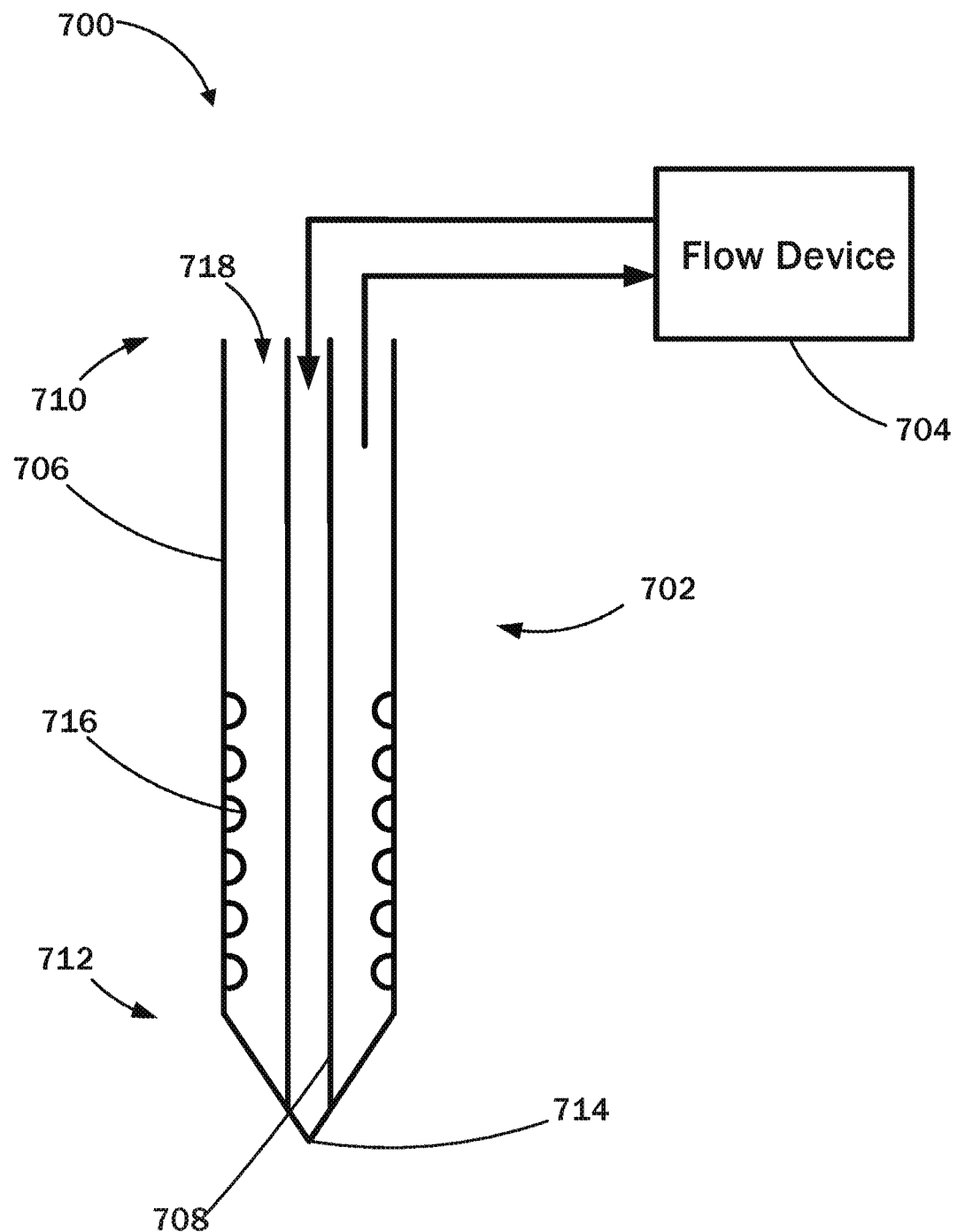
FIG. 7 illustrates an injection system configured to inject slurry into or around a desired tissue region.

In general, an injection system configured to deliver one or more of the slurries described herein into or around PVAT or periadventitial adipose tissue may include an injection device (e.g., a needle, a catheter, a pump, etc.). FIG. 7 illustrates one non-limiting example of an injection system 700 that may be utilized to inject the slurries described herein into or around a desired tissue region (e.g., PVAT or periadventitial adipose tissue). In the illustrated non-limiting example, the injection system 700 includes a catheter 702 and a flow device 704. In some non-limiting examples, the flow device 704 may be in the form of a pump.

The catheter 702 may include an outer surface 706 and a central lumen 708. The outer surface 706 and the central lumen 708 extend along the catheter 702 from a proximal end 710 to a distal end 712. A tip 714 may be arranged at the distal end 712 of the catheter.

In the illustrated non-limiting example, the outer surface 706 of the catheter may be fenestrated along a predefined axial length thereof. The fenestrated length of the outer surface 706 may be arranged adjacent to the distal end 712 of the catheter 702. The fenestrated length of the outer surface 706 may include one or more suction apertures 716 that extend radially through the outer surface 706. The one or more suction apertures 716 may provide fluid communication between the desired tissue region and an outer passageway 718 defined along the interior of the catheter 702. The outer passageway 718 may be arranged radially between the outer surface 706 and the central lumen 708.

Figure 8:
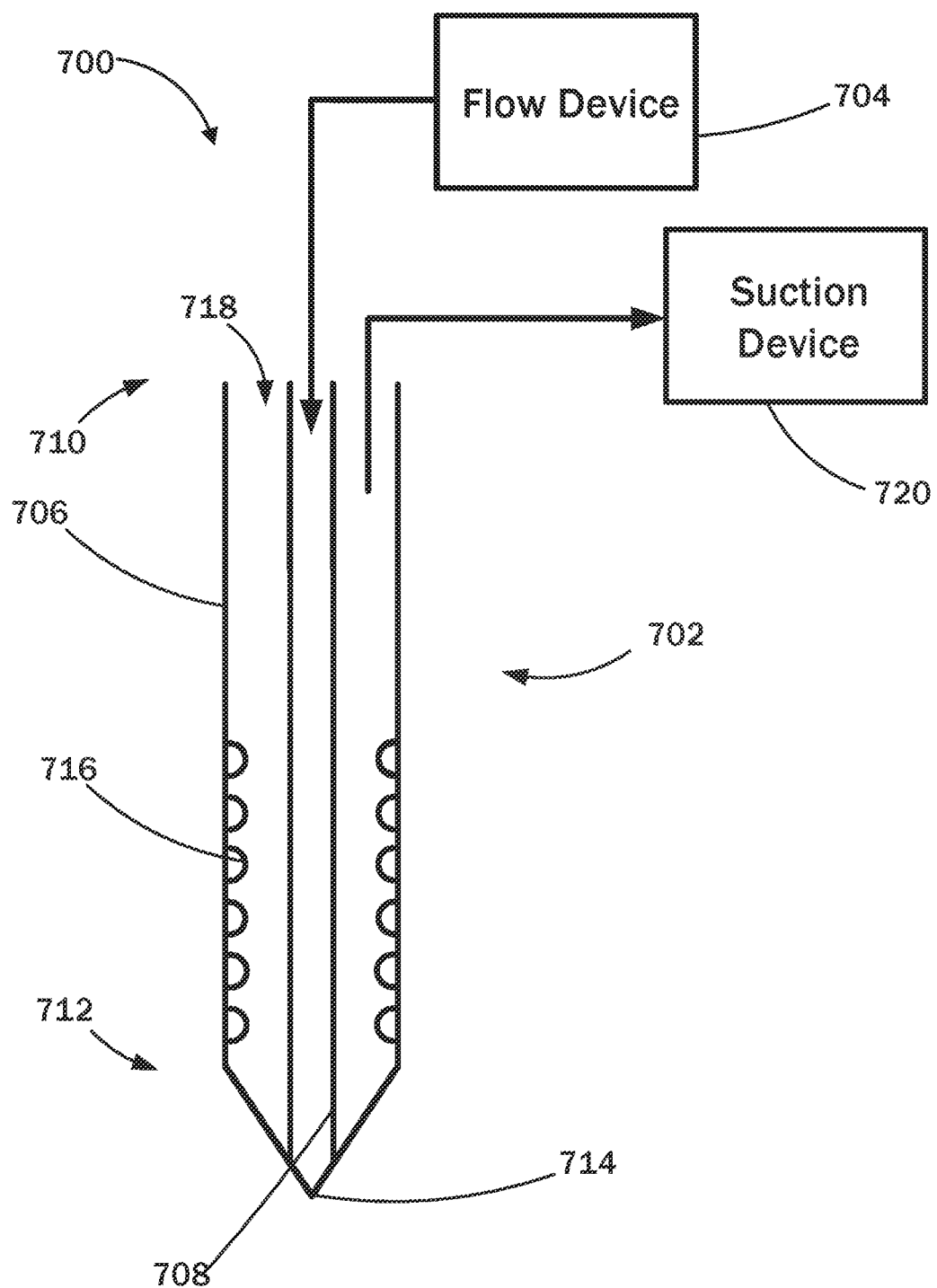
FIG. 8 illustrates the injection system of FIG. 7 including a suction device.

In operation, the flow device 704 may provide a desired volume or flow rate of one of the slurries described herein to the central lumen 708. The slurry may be at a predetermined temperature. The slurry may flow along the central lumen 708, through the tip 714 and into or around the desired tissue region, for example, to treat a vascular disease. In some applications, the delivered slurry may melt, for example, within minutes, and the melted slurry may be suctioned from the desired tissue region through the one or more suction apertures 716 and along the outer passageway 718. In some non-limiting examples, the flow device 704 may be configured to both provide the slurry to the central lumen 708 and suction the melted slurry through the outer passageway 718. In some non-limiting examples, as illustrated in FIG. 8, the flow device 704 may provide the slurry to the central lumen 708, and a suction device 720 may suction the melted slurry through the one or more suction apertures 716 and along the outer passageway 718.

Figure 9:
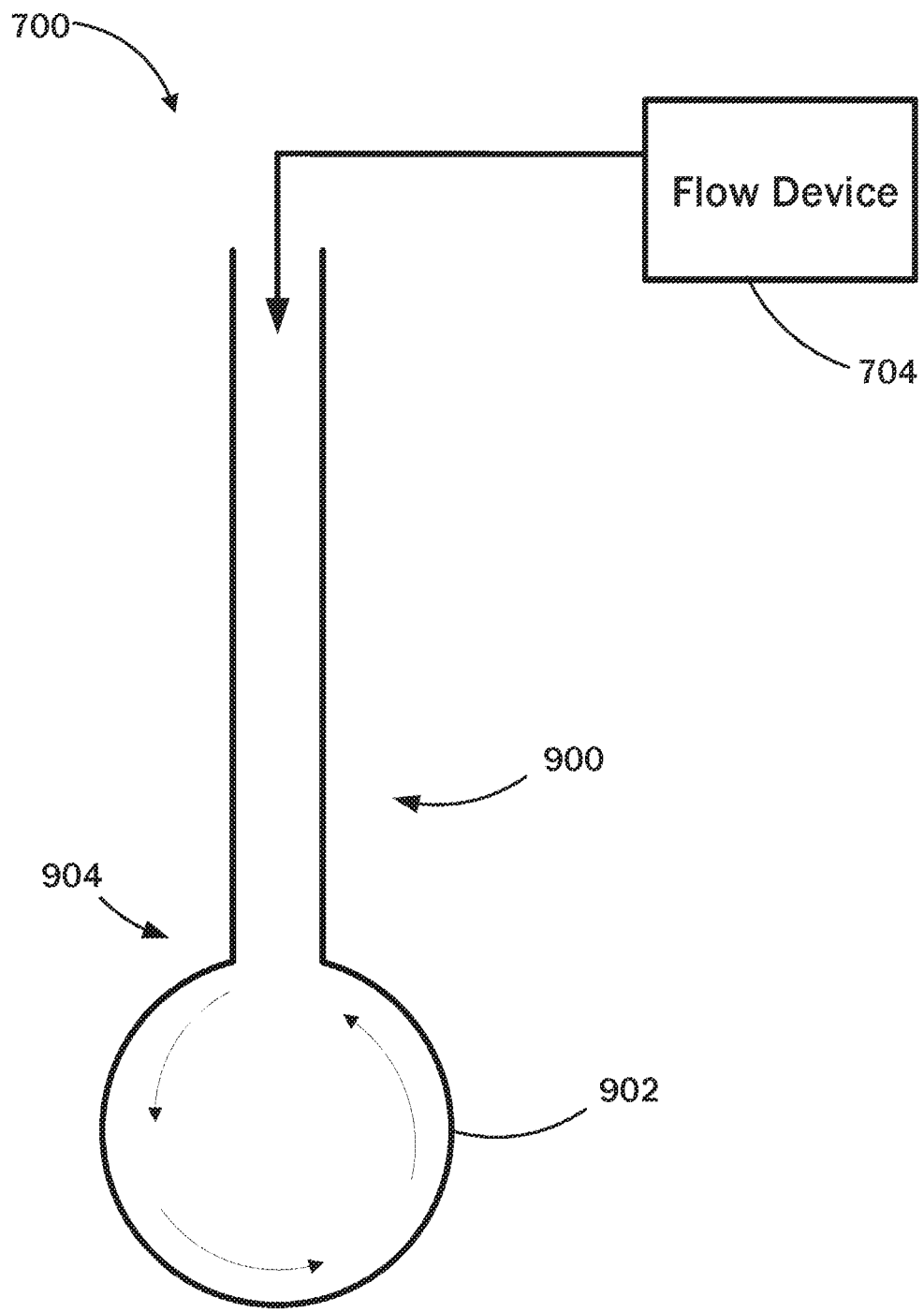
FIG. 9 illustrates an injection system configured to inject slurry into or around a desired tissue region that includes a balloon-based catheter.

In some non-limiting examples, as illustrated in FIG. 9, the injection system 700 may include a balloon-based catheter 900. The balloon-based catheter 900 may include an inflatable balloon 902 arranged at a distal end 904 thereof. The flow device 704 may be configured to provide slurry through the balloon-based catheter 900, which inflates the balloon 902 and recirculates slurry around the balloon 902. Upon inflation of the balloon 902, the balloon 902 may come into contact with a desired tissue region (e.g., PVAT or periadventitial adipose tissue).

In some applications, the use of the balloon-based catheter 900 may allow precooling or augmented cooling. In some applications, the balloon-based catheter 900 may allow colder and non-physiologic slurries to be used, because the slurry will not come into direct contact with tissue. For example, the slurries may be manufactured with a higher glycerol content (e.g., 40-50%) so the slurries are capable of being made colder (e.g., close to −20° C. or colder).

In some non-limiting examples, the use of video assisted thoracoscopy surgery may be leveraged to deliver the slurry to PVAT or periadventitial adipose tissue. In some non-limiting examples, thoracoscopic surgery with long access needles can be used to deliver slurry to the epicardial adipose tissue around coronary arteries.

Working Examples

Quantitative Model to Illustrate the Behavior of Injected Slurries

Figure 36A:
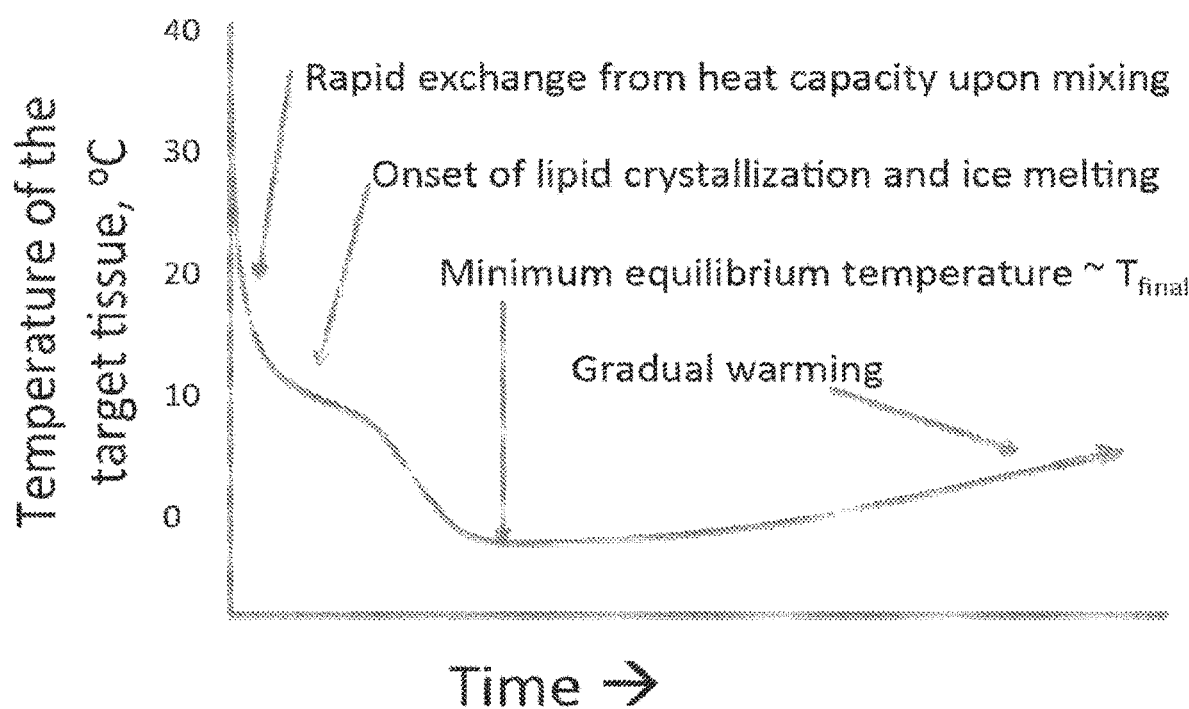
FIG. 36A depicts a quantitative model to illustrate the behavior of injected slurries according to an embodiment of the invention.
Figure 36B:
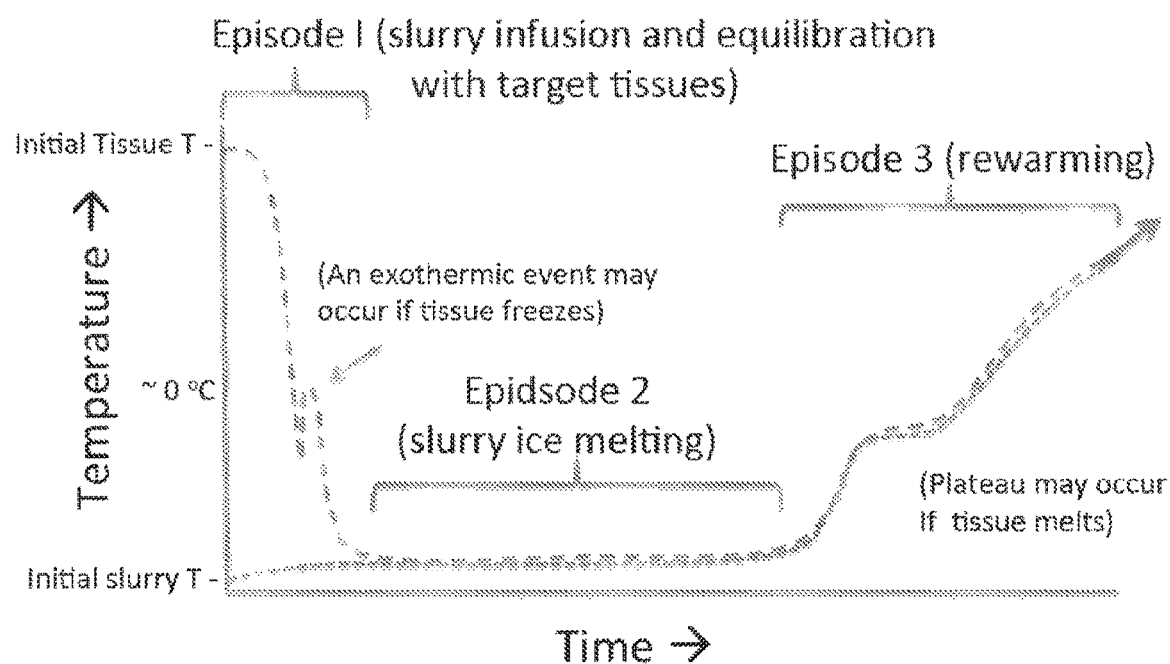
FIG. 36B depicts three stages of heat exchange following infusion of a slurry into a tissue.

Simplifying and reasonable assumptions are made in a quantitative model to illustrate the behavior of injected slurries, as depicted in FIG. 36A.

Heat capacity is an important component of the heat exchange between a slurry and a tissue. The first heat exchange to consider is that of the energy stored by the heat capacity of slurry and tissue. The energy per unit volume in a medium stored by heat capacity is given by H=TρC, where H is energy density (cal/cm$^3$), T is temperature (° C.), ρ is density (gm/cm$^3$), and C is specific heat capacity (cal/° C. gm). Assume that ρC is the same for slurry and tissue and water, i.e. ρC=1 cal/gm-° C. This assumption is approximately true for all soft tissues except fat, for which ρC is lower by about a factor of 2.

Consider a local volume of tissue into which slurry has been introduced. When slurry is introduced with a volume fraction of $f_s$ into local tissue, the local tissue occupies a volume fraction of (1-$f_s$). The stored heat per unit volume of the resulting slurry-tissue mix due to heat capacity of the slurry is $H_s = f_s T_s \rho C$, and the stored heat per unit volume due to heat capacity of the tissue is $H_t = (1-f_s)T_t\rho C$. After rapid exchange of the thermal energy due to heat capacity, a new temperature $T_m$ is achieved. Thermal energy due to heat capacity of the mix is given by $H_m = T_m \rho C$. Conservation of energy in the local heat exchange requires that $H_s + H_t = H_m$. Combining the equations:

$$f_s T_s \rho C + (1 - f_s)T_t \rho C = T_m \rho C$$

Solving for $T_m$, the slurry-tissue mix temperature after this initial part of heat exchange:

$$T_m = f_s T_s + (1 - f_s)T_t$$

Because the temperature of physiological ice slurries is generally close to 0, this simplifies to:

$$T_m = (1 - f_s)T_t$$

The rapid heat exchange upon mixing due to heat capacity alone is the volume-weighted average of the two starting temperatures. For example, if $f_s$=0, no slurry is added, and $T_m = T_t$, the starting tissue temperature. If $f_s$=1, the mix is all slurry, and $T_m$=0. If $f_s$=0.5, there is a 50%-50% mix of slurry and tissue, and the resultant temperature after mixing is the average of the slurry and the tissue starting temperatures. Typical values offs for interstitial injection of a slurry range from about 0.2 to about 0.8, i.e., the mixed slurry-tissue volume may have about 20% to 80% slurry content. Also consider the situation of $f_s$=0.5. If the starting tissue temperature $T_t$ is 37° C., then Tm=18.5° C. after exchange of heat from heat capacity.

The volume fraction of ice in a physiological slurry in this model is defined as Is, being the volume of ice per unit volume of slurry. Immediately after injection into tissue, the initial volume fraction of ice in the local slurry-tissue mix, is therefore:

$$I_0 = f_s I_s$$

wherein $I_o$ is the total amount of ice available for melting, per unit volume of the slurry-tissue mix.

After the rapid heat exchange from heat capacity, ice in the slurry component of the slurry-tissue mix begins to melt, absorbing heat and cooling the slurry-tissue mix. Ice in the slurry-tissue mix melts until it is gone, or until an equilibrium temperature is reached, before the period of gradual warming by body heat exchange briefly discussed above. In pure water, ice and liquid water can co-exist at equilibrium temperatures between 0° C. and 4° C. In tissue, there are numerous solutes that cause freezing point depression, such that ice and water co-exist over a somewhat lower temperature range, e.g., about −8° C. to 0° C. in skin. Lipids in the tissue are in a liquid state at normal body temperature. As cooling of the slurry-tissue mix occurs due to ice melting, below a certain temperature lipids can crystallize. In essence, there is a heat exchange between the latent heat of fusion from melting ice, and the latent heat of fusion from lipid crystallization. These two processes proceed in opposite directions (e.g., the water melts, the lipids crystallize) because lipid crystallization occurs at temperatures considerably higher than the freezing point of water. Most animal fats crystallize at between 10° C. and 15° C., depending on the length and saturation of the lipid chains in triglyceride molecules. Wax esters and free fatty acids crystallize at similar temperatures. Polar lipids crystallize at lower temperatures, for example the phospholipids of cell membranes can remain somewhat fluid even well below 0° C.

Injected physiological slurries are effective to inhibit pain or itch by affecting nerve myelin sheath lipids. Lipids of the sheath crystallize well above 0° C. Effective treatment depends on variables including the starting tissue temperature $T_t$, the ice content of slurry L, the amount and speed of slurry injected to achieve an adequate slurry fraction $f_s$ in the slurry-tissue mix, the target lipid content of the tissue $L_t$, its crystallization temperature $T_c$, and the time for which some ice remains in the slurry-tissue mix.

Enthalpy of fusion (also called heat of fusion) describes how much thermal energy is absorbed (endothermic) or released (exothermic) due to changing from solid to liquid state. The melting of ice is an endothermic transition requiring a large amount of thermal energy. For water, the heat of fusion is 80 cal/gm. The density of ice at 0° C. is 0.92, such that the volumetric heat of fusion, $H_{ice}$ (the heat energy needed to melt a volume of ice) is:

$$H_{ice} = 74 \text{ cal}/\text{cm}^3$$

The total heat per unit volume that can be absorbed by melting all of the ice in the slurry-tissue mix, $Q_{icetotal}$, is simply its total ice content multiplied by $H_{ice}$:

$$Q_{icetotal} = f_s I_s H_{ice}$$

Typical values as mentioned above for $f_s$ range from about 0.2 to 0.8, and the ice content of physiological slurry can be up to about 50% ($I_s \sim 0.5$). For the approximate maximum of $I_s=0.5$, the range (without limitation) for $Q_{icetotal}$ in the slurry-tissue mix is therefore about 7 to 30 cal/cm$^3$.

The heat of fusion for animal fat lipids ranges from about 30-50 cal/gm. The density of lipids range from about 0.8-0.9 gm/cm$^3$ (e.g., palmitic triglyceride in solid phase is 0.85 gm/cm$^3$). Taking the mean value of 40 cal/gm as the heat of fusion, the latent heat per unit volume for crystallization of lipids is about:

$$H_{lipid} = 34 \text{ cal/cm}^3.$$

Thus, the latent heat for crystallization of lipids is less than half of that for melting of ice. Cooling of the slurry-tissue mix proceeds by some ice melting, until the temperature reaches about 10° C., the temperature necessary for lipid crystallization to begin. The thermal energy from consumed by dropping the temperature of the slurry-tissue mix to about 10° C. is given by:

$$Q_{to10°C} = (T_m - 10)\rho C.$$

At about that temperature, whatever ice remains from the slurry will melt, absorbing the energy necessary to crystallize about twice its own volume of lipid. If all of the tissue lipid is crystallized, more ice will melt and the temperature will drop below about 10° C., potentially into the approximately −8° C. to 0° C. range at which ice and liquid water can coexist in tissue. The lipid content of the slurry-tissue mix is therefore another important factor. Defining the lipid content of the tissue as $f_{tlip}$, the lipid content of the slurry-tissue mix is:

$$f_{mlip} = (1 - f_s)f_{tlip}.$$

The value of $f_{tlip}$ depends on tissue type. The lipid content of most soft tissues ranges from about 5% (most connective tissues) to about 80% (fat), i.e., $f_{tlip}=0.05$ to 0.8. The energy per unit volume of the slurry-tissue mix that is produced by crystallizating all of the lipid present, is:

$$Q_{liptotal} = f_{mlip} H_{lipid}$$

During the period of latent heat exchange between ice melting and lipid crystallization in the slurry-tissue mix, ice in the slurry melts until all of the lipid is crystallized, or until the ice is gone.

The fraction of the lipid in the slurry-tissue mix that crystallizes is simply given by the energy balance:

$$f_{lipxtal} = \frac{Q_{icetotal} - Q_{to10°C}}{Q_{icetotal}}$$

If $(Q_{icetotal} - Q_{to\ 10°\ C.}) < Q_{liptotal}$, a fraction of the lipid will crystallize, given above by $f_{lipxtal}$. If $(Q_{icetotal} - Q_{to\ 10°\ C.}) = Q_{liptotal}$, all of the lipid will crystallize and all of the ice will melt; the temperature will remain near about 10° C., the phase transition temperature for most animal lipids. If $(Q_{icetotal} - Q_{to\ 10°\ C.}) > Q_{liptotal}$, all of the lipid will crystallize, and the temperature will thereafter decrease below about 10° C. until all of the ice is melted or until an equilibrium exists between ice and liquid water in the tissue, i.e., in the temperature range of about −8° C. to 0° C. The lowest temperature reached is determined by heat exchange between the residual ice melting, and the heat capacity of the slurry-tissue mix. The lowest temperature $T_{final}$ can therefore be estimated by equating the latent heat per unit volume absorbed by melting of the residual ice, with the heat associated with heat capacity of the temperature drop below about 10° C.

The latent heat associated with the residual ice melting after the lipid is crystallized is $Q_{iceresidual} = Q_{icetotal} - Q_{to\ 10°\ C.} - Q_{liptotal}$, and the amount of residual ice per unit volume is $$I_{residual} = \frac{Q_{iceresidual}}{H_{ice}}.$$

The temperature drop to $T_{final}$ due to residual ice melting can be estimated by: $Q_{iceresidual} \sim (10 - T_{final})\rho C$, which rearranges to $$T_{final} \sim 10 - \frac{Q_{iceresidual}}{\rho C}.$$

The local heat exchanges modeled above occur over a time scale of seconds because the slurry is intimately in contact with tissue, by mixing flowing and/or dissecting through the soft tissue during interstitial injection. After exchange of the latent heats from melting ice and crystallizing lipids, the temperature of the slurry-tissue mix settles at about $T_{final}$, then gradually warms due to conduction and convection. The rate of gradual warming depends therefore on the rates of conduction and convection. In the absence of blood flow (convection), warming by conduction involves a minimum characteristic time, proportional to the square of the diameter of the local slurry-tissue mix. Typically in soft tissues, the time in seconds for substantial warming of a region by conduction (to 1/e of a final equilibrium value) is approximately equal to the square of the diameter in millimeters. For example, a 10 mm diameter slurry-tissue mix would typically necessitate about 100 seconds for substantial warming, and a 30 mm diameter slurry-tissue mix would typically necessitate about 900 seconds (i.e., 15 minutes) for substantial warming by conduction. Depending on the ice content, some ice may remain even after this estimated period of substantial warming. The model presented here is illustrative, not exact. Direct measurement of slurry and tissue temperatures can be performed. As shown below, such measurements are generally consistent with this approximate model.

Ex Vivo Human Abdominoplasty Tissue Experiments

Using ex vivo pig tissue and human abdominoplasty tissue samples, Applicant tested the ability of a sterile, cold injectable slurry to reduce the temperature of adipose tissue.

Figure 10:
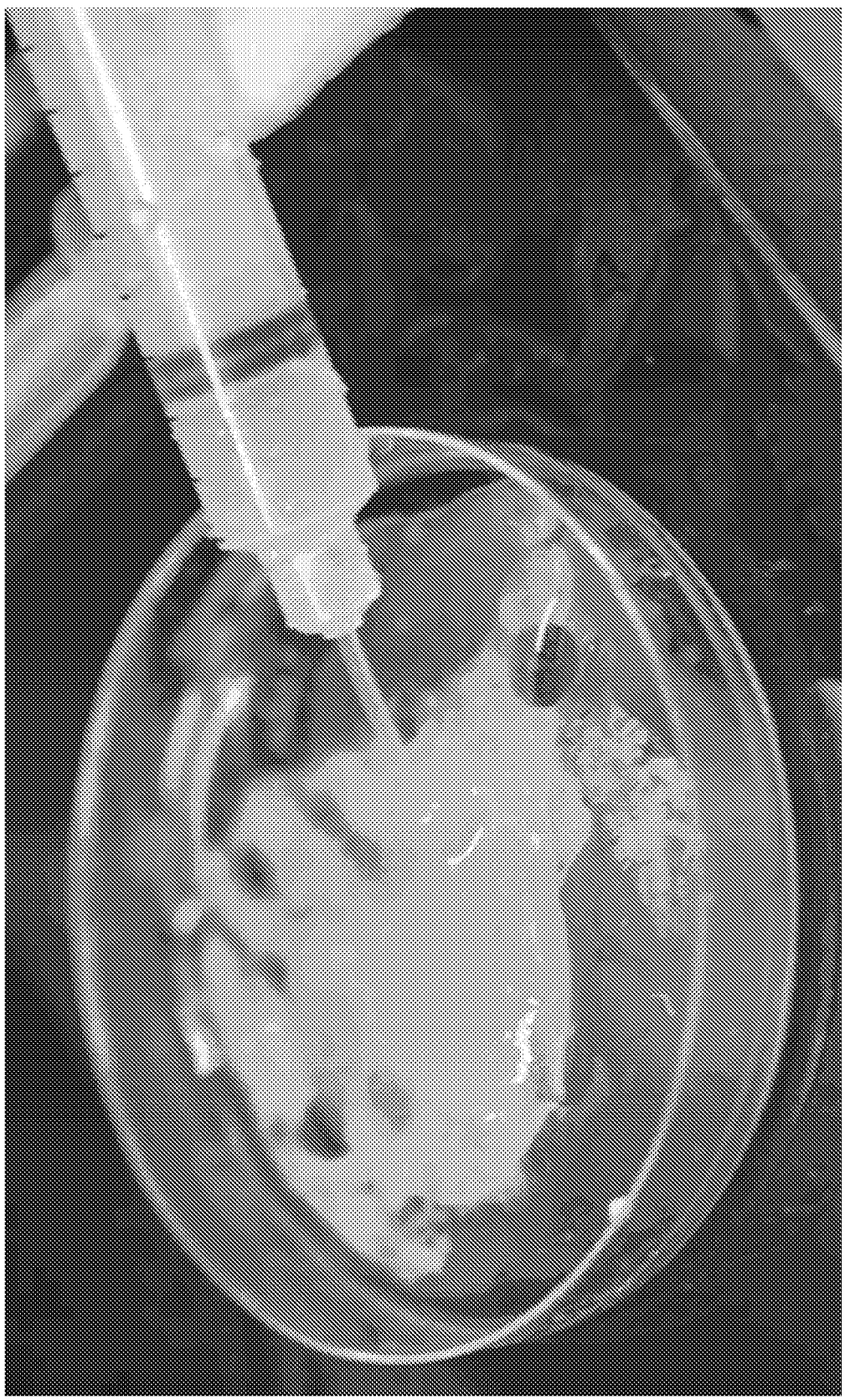
FIG. 10 depicts an ice slurry with a high concentration of small ice particles according to an embodiment of the invention.

FIG. 10 depicts an ice slurry with a high concentration of small ice particles that can be easily injected via a 15-19 gauge needle into the subcutaneous fat tissue.

Figure 11A:
FIGS. 11A, 11B and 11C depict the results of injection of an ice slurry into human abdominoplasty adipose tissue according to an embodiment of the invention.
Figure 11C:
Figure 11B:

FIGS. 11A-11C depict the results of injection of an ice slurry into human abdominoplasty adipose tissue. Ice crystals 802 are clearly visible in the adipose tissue.

Figure 12B:
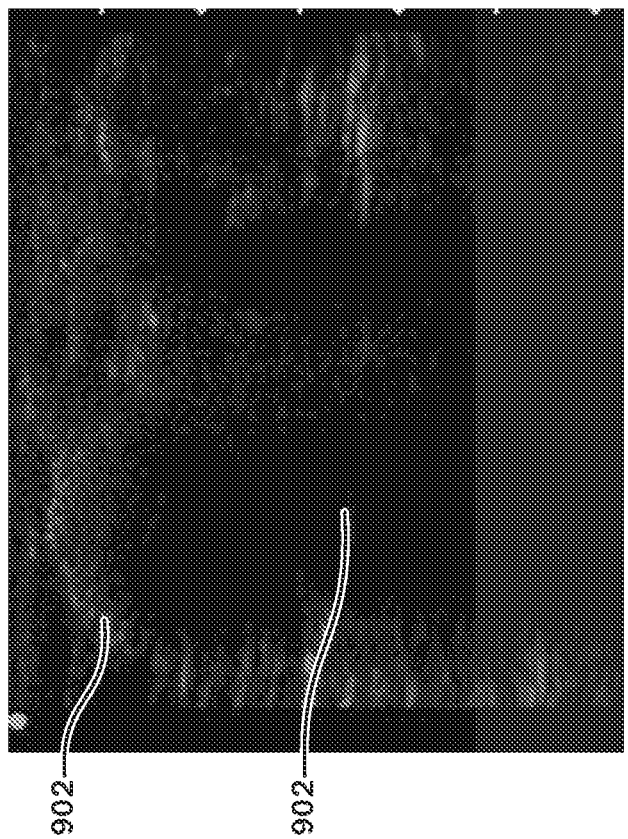
FIGS. 12A and 12B depict the detection of injected slurry with ultrasound in ex vivo human skin according to an embodiment of the invention.
Figure 12A:
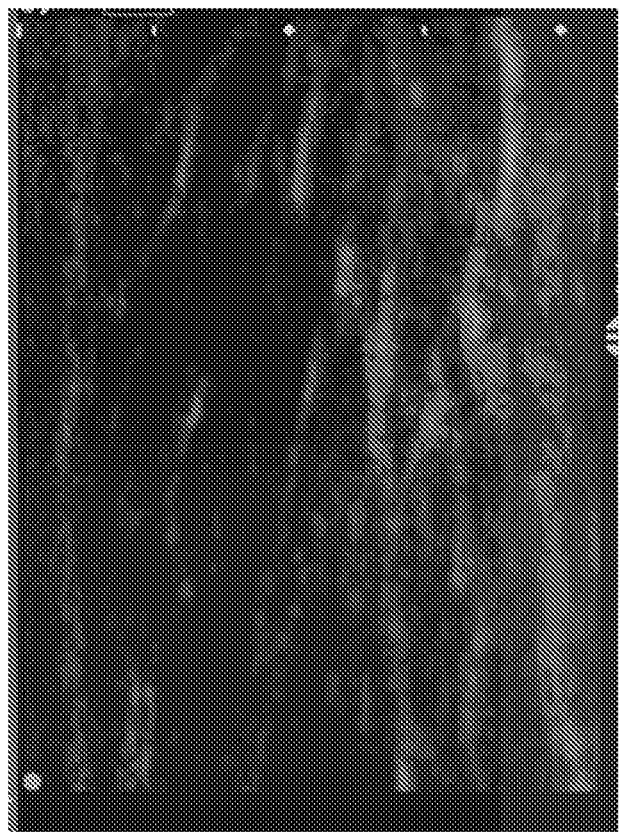

These injections of slurry into tissue create an area of localized ice collection in the subcutaneous fat, which can be detected by ultrasound as depicted in FIG. 12B in contrast to the ultrasound image of human skin prior to slurry injection in FIG. 12A. This injected ice was in direct contact with the adipose tissue. The injection of the slurry was able to reduce the temperature of the adipose tissue below 0° C., which is well below the crystallization temperature of fat. This experiment demonstrates that heat exchange between slurry and local fat tissue is capable of lowering the adipose tissue temperature down to a level sufficient to damage fat tissue and produce local fat loss.

Slurry has many times (typically 5-8 times, depending on the ice content) the cooling capacity of liquid coolants (such as cold saline) and is, therefore, able to extract much more thermal energy to selectively damage lipid rich tissue such as fat. For example, embodiments of the sterile and biocompatible slurries described herein generate a target tissue temperature of −3° C. to −2° C. Damage to the target lipid-rich tissue tends to be enhanced when the cooling rate is high at least in part because of limited time for various protective tissue responses. For example, when 20-25 cc of slurry was injected into subcutaneous fat, tissue temperatures in the −3° C. to −2° C. range were produced nearly instantaneously as depicted in FIG. 13.

Figure 13:
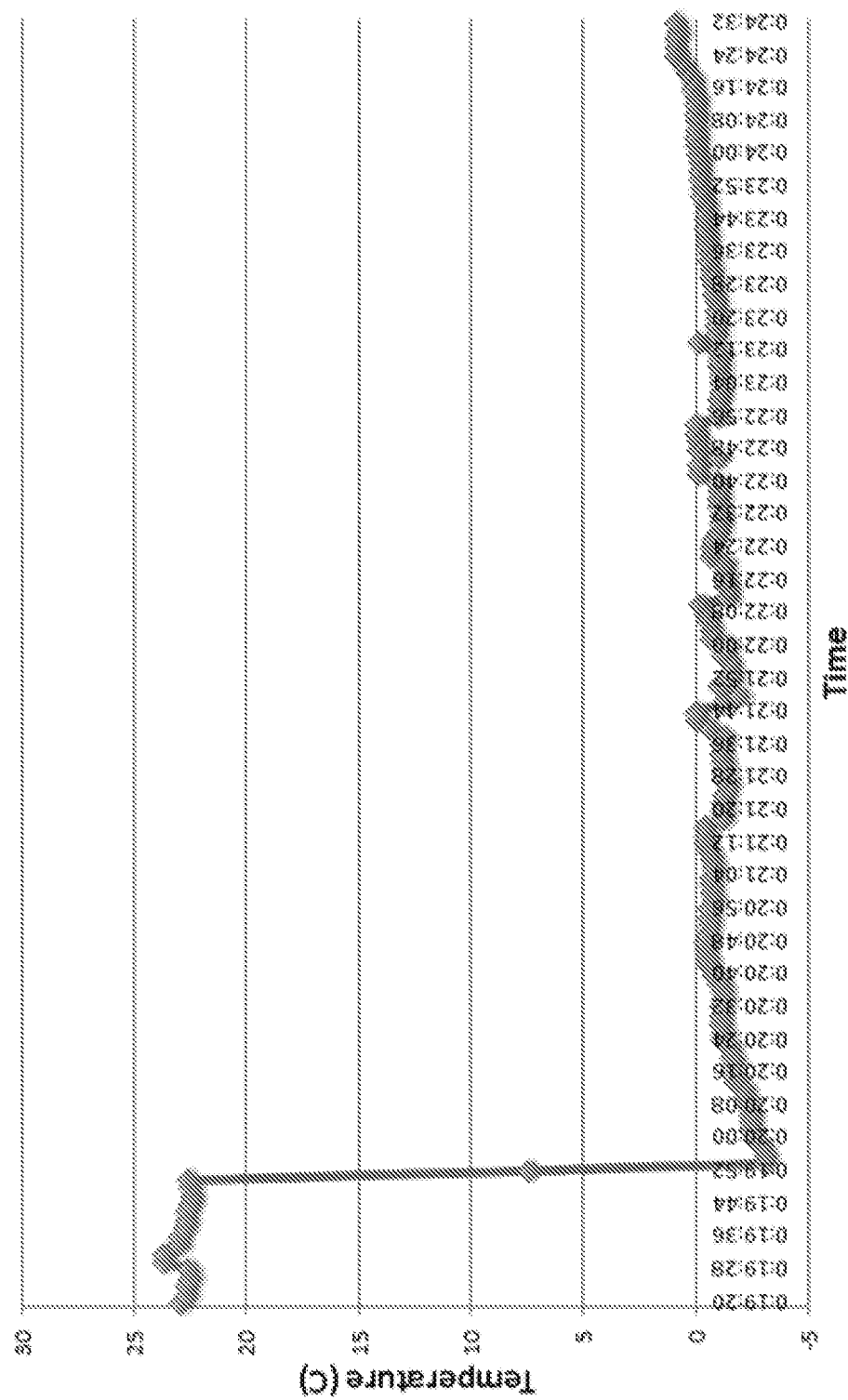
FIG. 13 depicts a chart of the temperature of an ex vivo human abdominoplasty specimen being heated from below after injection of a cold slurry according to an embodiment of the invention.

FIG. 13 depicts the results of injection of slurry into ex vivo human abdominoplasty specimen. Prior to injection, a 38° C. heating pad was placed underneath the specimen to provide constant heat mimicking human core temperature. The slurry was injected into human fat tissue using a 60 ml syringe and 15 gauge needle with the starting fat temperature of 23° C. as measured by a thermocouple embedded into the adipose tissue. After slurry injection, the temperature of the adipose tissue decreased immediately down to −3° C. As ice melts in the slurry, tissue temperature in the tissue immediately adjacent to the slurry is maintained at or below 0° C. until all of the ice has melted. A single slurry injection was able to maintain it below 0° C. for at least 10-15 minutes.

The low temperatures generated by injected slurry causes localized and selective damage to lipid-rich target tissue such as adipose tissue and myelinated nerves.

In Vivo Swine Experiments
Investigation of Cryolipolysis in Swine

Applicant conducted experiments injecting physiological sterile ice slurry into the subcutaneous fat of live swine. In this controlled study, the effects of slurry injections were compared with injection of melted slurry and of normal saline at other sites in the same animal. Injections were performed in accordance with an approved animal study under general anesthesia.

Applicant generated sterile biocompatible slurry with a temperature at injection ranging from +1° C. to −3° C. Prior to injection, ultrasound measurements and standardized photographs were obtained of the sites that were to be injected in swine. Sites were injected with cold slurry, room temperature melted-slurry (a solution without ice), water, or normal saline. Another control site was not injected and received brief skin cooling only. A 15 gauge needle was used, however, Applicant confirmed in other experiments that the same slurry composition is injectable through a 19 gauge needle.

Sites were injected through the skin only into an area of approximately 4 cm×4 cm. Approximately 20 cc of cold or room temperature slurry and saline control were successfully delivered to the subcutaneous fat of predestinated sites.

After the cold slurry was injected, the temperature inside the injection site was as cold as −2° C. The duration of cooling (defined as the period in which the temperature of the treatment site remains below +5° C.) ranged from approximately 5 to 19 minutes. After injection, the skin surface overlying all of the injection sites (experimental and control) becomes raised due to the volume added to fat under the skin. This reaction subsides rapidly as the slurry or liquids injected gradually diffuse into surrounding tissues.

Figure 14B:
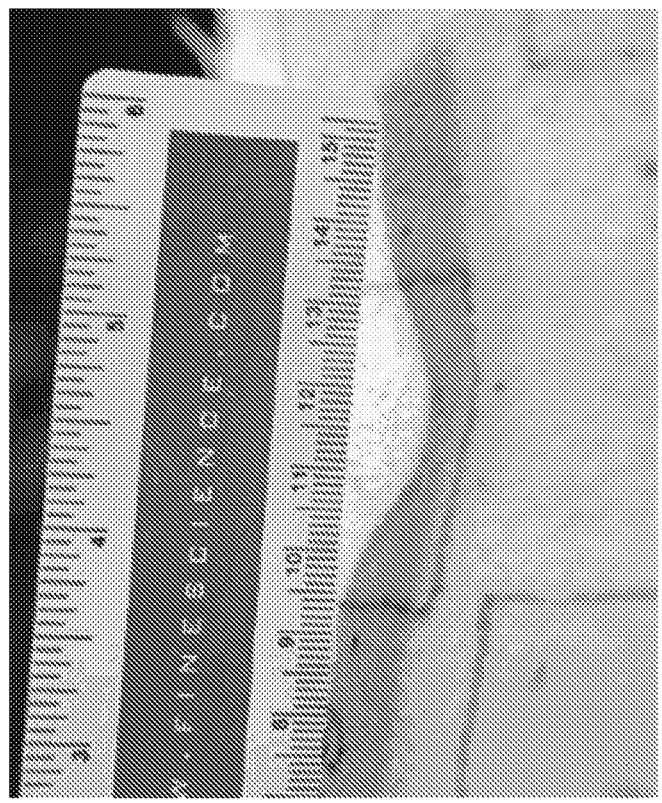
FIGS. 14A and 14B depict gross photographs of pig skin 4 weeks after injections of a melted, room temperature slurry (FIG. 14A) and cold slurry (FIG. 14B) according to embodiments of the invention.
Figure 14A:
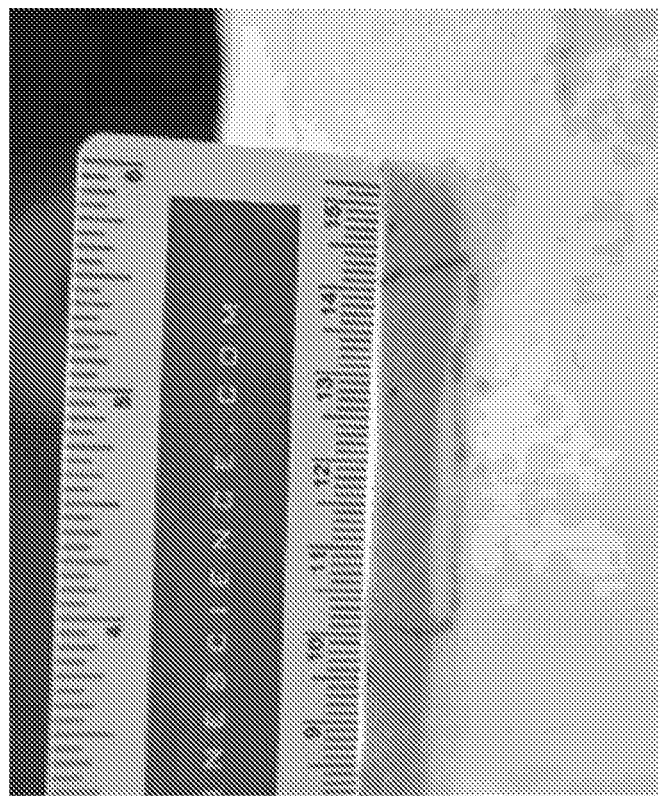
Figure 16B:
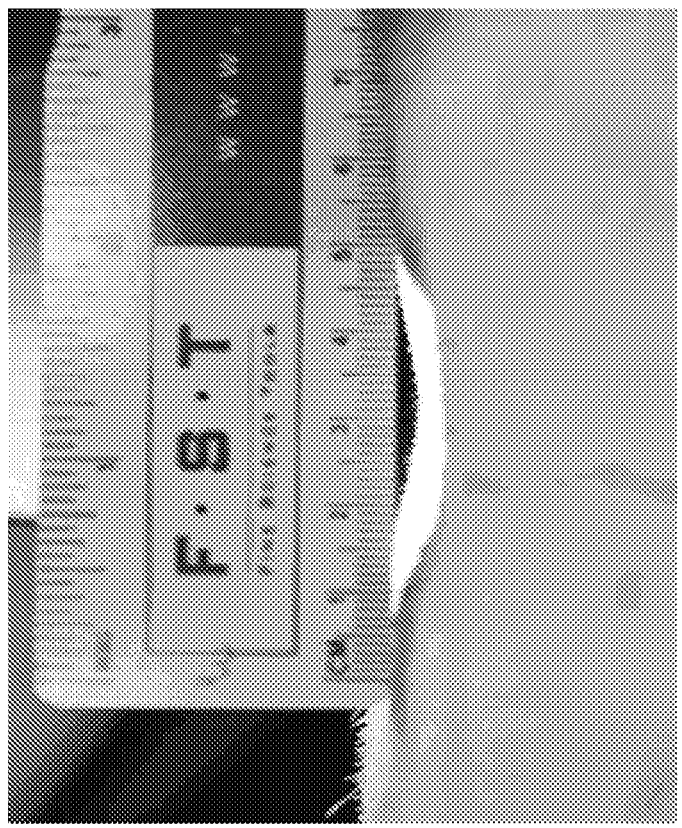
FIGS. 16A and 16B depict gross photographs of pig skin at another treatment site 4 weeks after injections of cold slurry according to an embodiment of the invention demonstrating a marked depression in skin caused by loss of subcutaneous fat at the site of the injection.
Figure 16A:
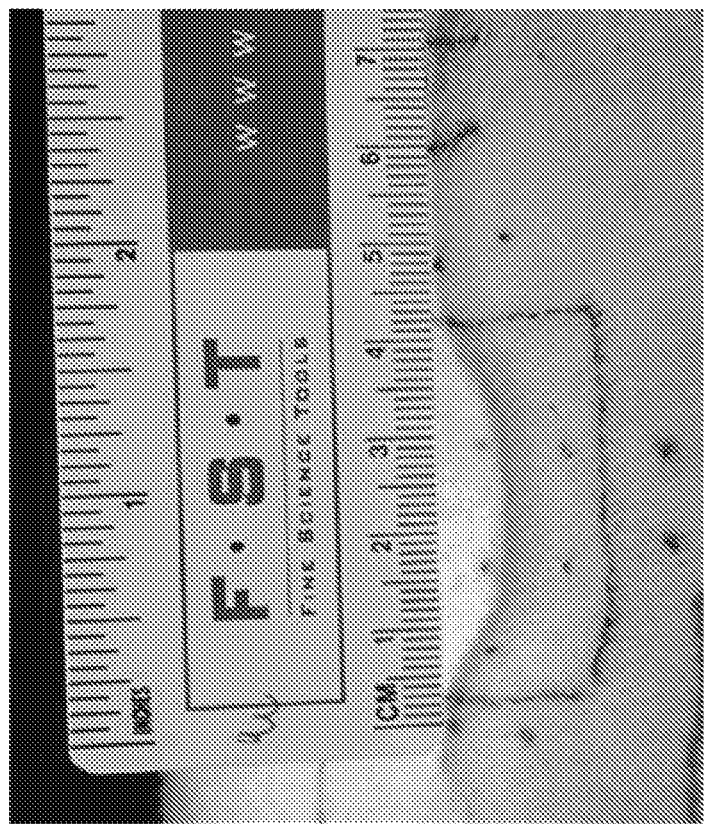

At approximately 3 to 4 weeks of follow-up, injection sites demonstrated obvious depression on gross inspection at the sites where cold slurry was injected as depicted in FIGS. 14B, 16A, and 16B corresponding to loss of subcutaneous fat. In contrast, there was no apparent depression at the sites where room temperature slurry, water, and saline were injected. It is important to note that on gross examination there was no sign of any damage to surrounding skin tissue. In addition, there was no sign of infection or nonspecific damage to the sites.

Figure 15B:
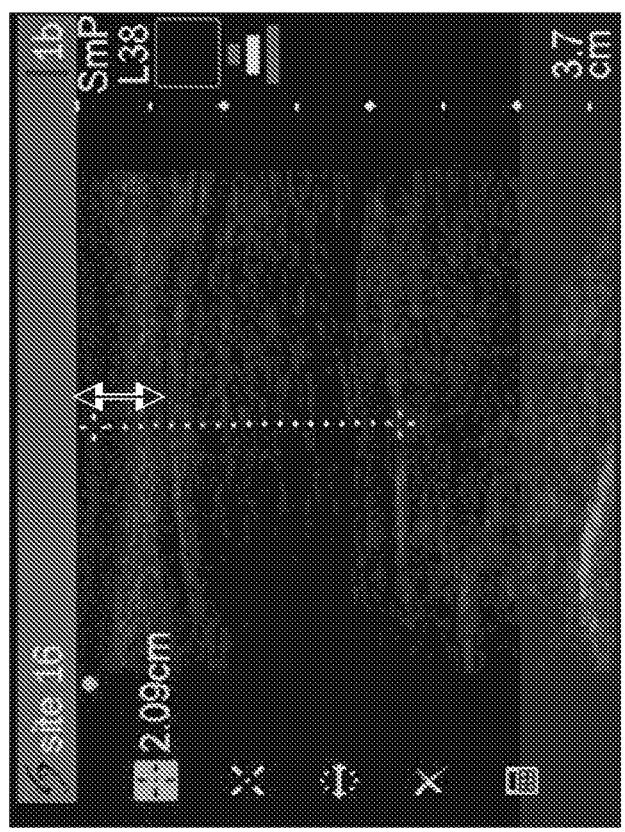
FIGS. 15A and 15B depict ultrasound images of pig skin at a treatment site prior to cold slurry injection (FIG. 15A) and 4 weeks after cold slurry injection (FIG. 15B) according to an embodiment of the invention.
Figure 15A:
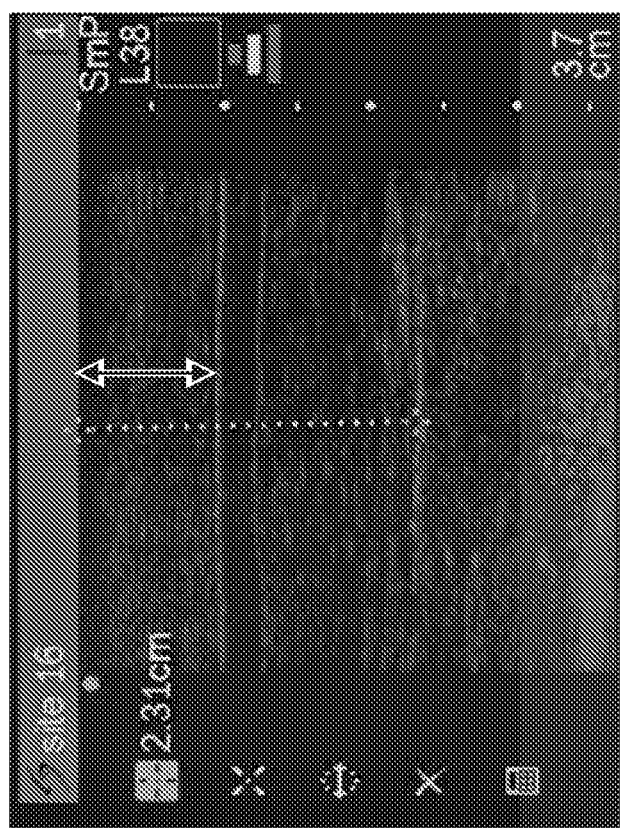
Figure 17B:
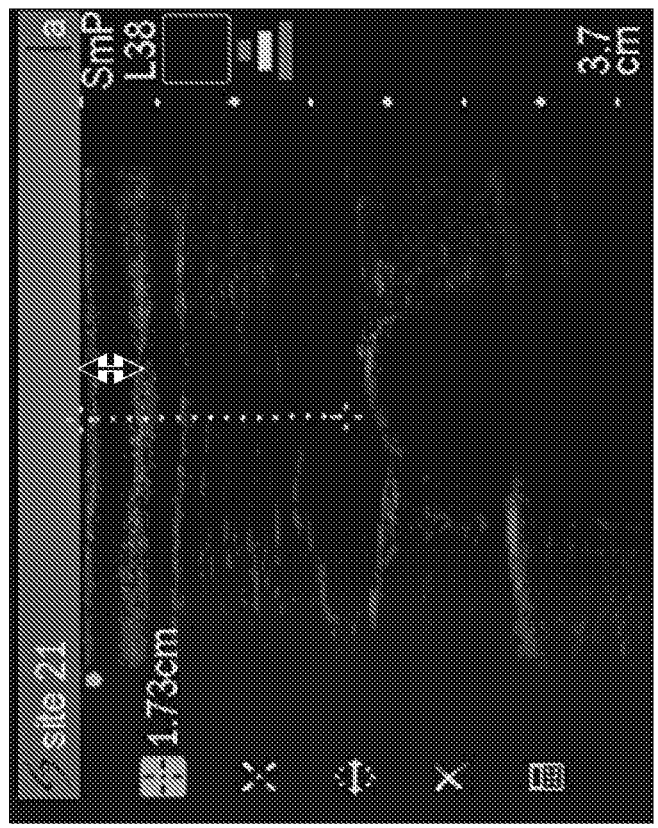
FIGS. 17A and 17B depict ultrasound images of pig skin at another treatment site prior to cold slurry injection (FIG. 17A) and 4 weeks after cold slurry injection (FIG. 17B) according to an embodiment of the invention.
Figure 17A:
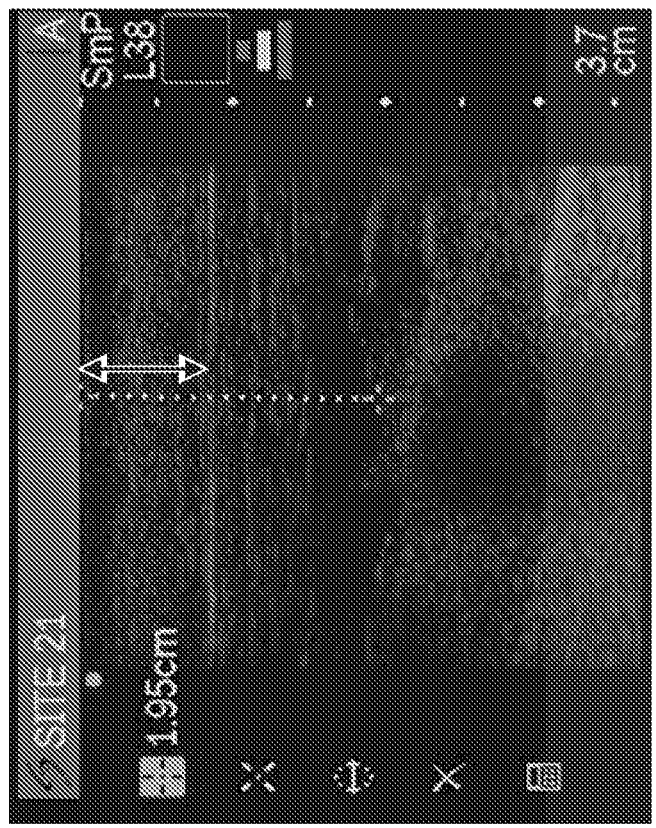

Ultrasound images of the sites at baseline (FIGS. 15A and 17A) and at 4 weeks after the injection (FIGS. 15B and 17B) clearly demonstrate approximately 40-50% loss of superficial subcutaneous fat tissue only in the sites injected with cold slurry.

Figure 23A:
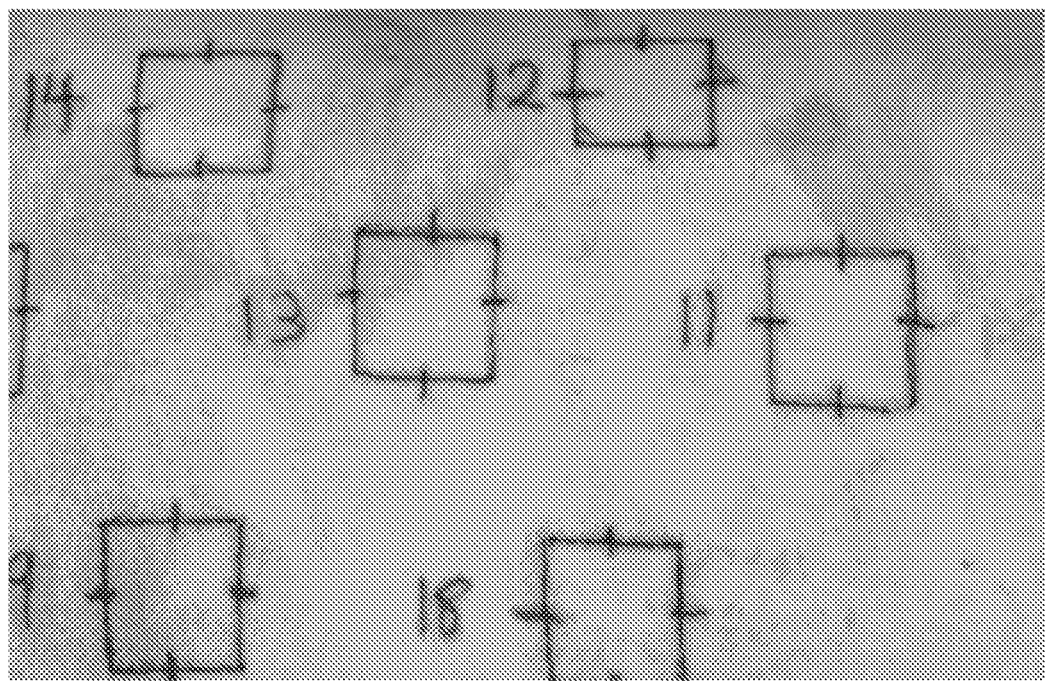
FIG. 23A depicts injection sites on a swine before injection.
Figure 23B:
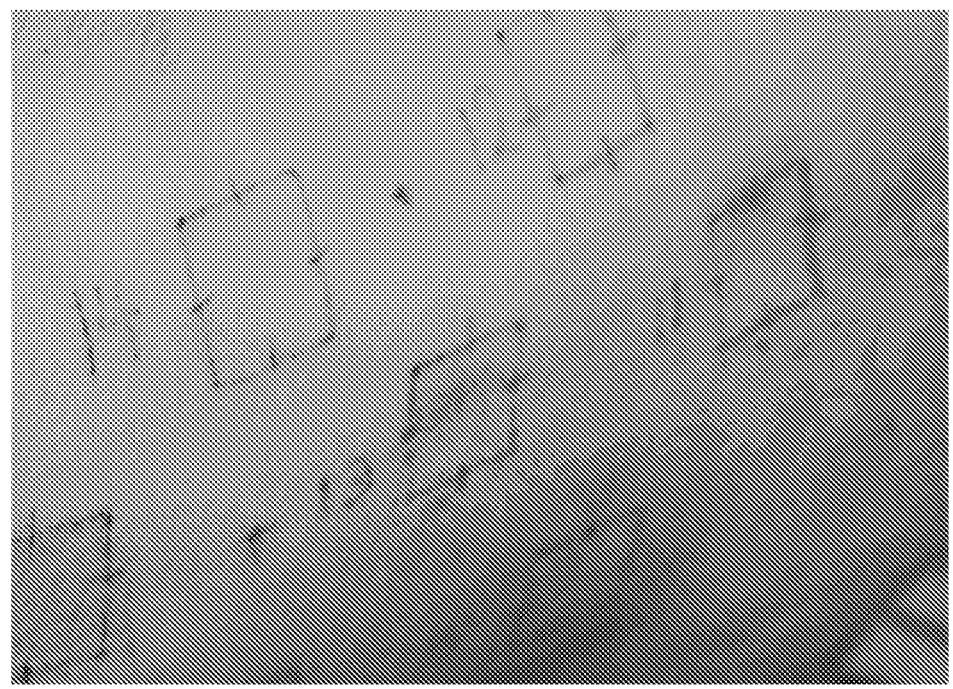
FIG. 23B depicts injection sites 14 days after injection.

Referring now to FIGS. 23A and 23B, further experiments were conducted on another pig using normal saline plus 10% glycerol slurry, room temperature (melted) slurry, both with and without precooling. FIG. 23A depicts injection sites before injection and FIG. 23B depicts injection sites 14 days after injection. On gross observation, there is no difference between the fat loss at pre-cooling plus slurry and slurry alone, indicating that a single injection of slurry deep in the subcutaneous fat layer, superficial to the muscular fascia is able to induce highly rapid, effective loss of subcutaneous fat even when the tissue is not pre-cooled.

In sites where the slurry was injected deep into the muscle, Applicant has not yet observed any muscular abnormalities, depressions or obvious effect of slurry on muscle tissue. Histologic analysis by Applicant has also shown that muscle tissue is not affected by slurry, thus supporting the hypothesis that only lipid rich tissue is targeted by cryoslurry.

Figure 24:
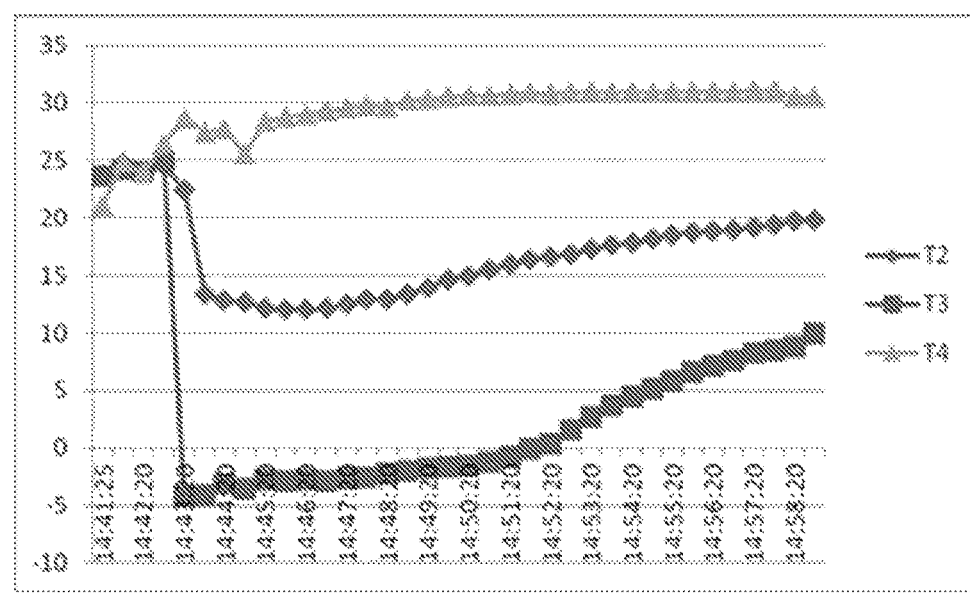
FIG. 24 depicts a graph of cooling at three locations during slurry injection into a swine.

FIG. 24 depicts a graph of cooling at three points. T3 represents the temperature of adipose tissue inside the pocket of slurry injection. T2 represents the temperature of adipose tissue adjacent to the pocket of slurry injection. T4 represents the temperature of skin adjacent to the pocket of slurry injection.

Figure 25A:
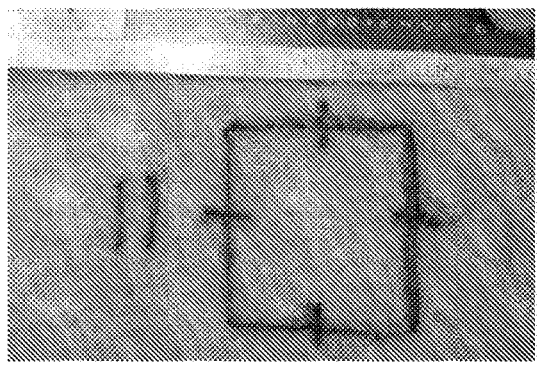
FIGS. 25A-25D are photographs of injection site 11, which received an injection of normal slurry with 10% glycerol at −4.1° C.
Figure 25B:
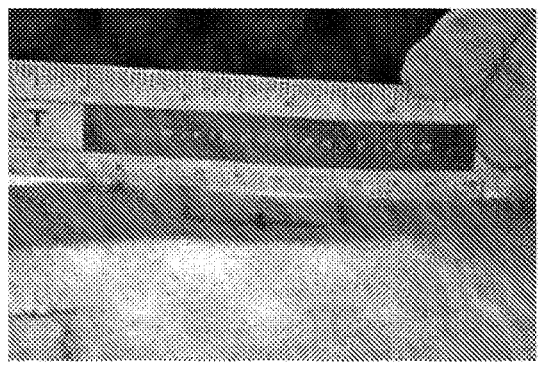
Figure 25C:
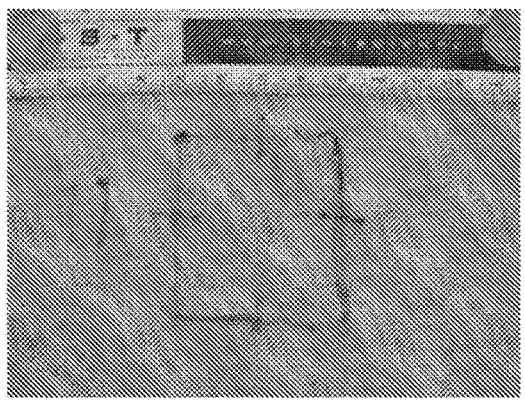
Figure 25D:
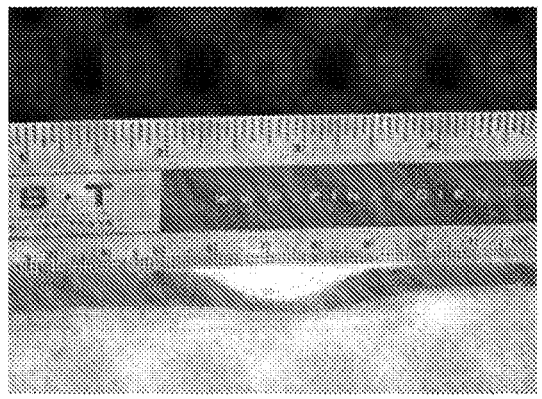

FIGS. 25A-25D are photographs of injection site 11, which received an injection of normal slurry with 10% glycerol at −4.1° C. FIGS. 25A and 25B depict the site pre-injection while FIGS. 25C and 25D depict the prominent depression 8 weeks post-injection.

The results of these experiments indicate that slurry injected into the subcutaneous fat leads to dramatic fat loss within 2-3 weeks after one injection based on ultrasound images and gross observation. Additionally, I (intramuscular) injection of slurry did not cause any gross tissue abnormalities. Cryoslurry is safe and effective in targeting lipid rich tissue such as subcutaneous fat even when adjacent to muscle or other non-lipid-rich tissue. No unwanted side effect such as skin necrosis, muscle necrosis, infection, damage to other cutaneous structures was observed after injection based on photographs and histology. Swine was able to tolerate close to 600 ml of slurry injections into subcutaneous fat without any sign of volume overload or systemic abnormalities. Moreover, the rate of cooling is very rapid and the rate and extent of cooling is related to proximity to injected slurry as depicted in FIG. 24.

Further injections were performed on another swine as summarized in Table 6 below. 1-2 cycles of 30 cc of slurry were injected into the subcutaneous fat. In order to demonstrate the presence or absence of indentation of the subcutaneous fat, a ruler was place horizontal to the skin and lit from the bottom. Light passing under (i.e., between the skin surface and straight edge) is indicative of indentation due to fat loss.

TABLE 6

Pig Experiments

| FIGS. | Site | Slurry Composition | Slurry Temperature |
|---|---|---|---|
| 29A & 29B | 23 | 6% Hetastarch + Lactated Ringer's Solution (+25 cc Room Temp Normal Saline for Thermal Smoothing) | −0.8° C. |
| 29C & 29D | 25 | 6% Hetastarch + Lactated Ringer's Solution (+25 cc Room Temp Normal Saline for Thermal Smoothing) | −0.2° C. (first injection) −0.4° C. (second injection) |
| 29E & 29F | 27 | Lactated Ringer's Solution + 10% Glycerol (5% in Slurry, 5% Pre-Injected) | −3.2° C. |
| 29G & 29H | 28 | 5% Glycerol + Lactated Ringer's Solution | +0.7° C. |
| 29I-29K | 29 | Normal Saline | −0.2° C. |

These experiments highlight the role of ions (e.g., potassium, chlorides, magnesium, calcium, and the like) in increasing the cooling power of slurries as well as the function of two-phase (i.e., ice and liquid) slurries on fat loss. Additionally, thermal smoothing as used at Sites 23 and 25 and chemical smoothing in Site 27 improved the flowability of slurry and reduction of fat. Thermal smoothing refers to allowing a slurry to partially melt prior to injection. Ice particles in a slurry freshly made by mechanically pulverizing ice, have various polygonal shapes, similar to the gravel produced when rock is pulverized. Such particles tend to interlock, limiting flowability. Partial melting produces more rounded ice particles, and a slurry with greater flowability for a given particle size and ice content. Other methods to improve flowability include using smaller ice particles, lower ice content, adding solute and/or surfactants prior to use of the slurry. Both isotonic and hypertonic solutions were shown to be capable of inducing fat loss. Additionally, slurries containing colloid solutions such as 6% hetastarch in Lactated Ringer's solution are capable of inducing fat loss as seen in Sites 23 and 25.

Treatment of Pharyngeal Fat with Ice Slurry

Figure 28A:
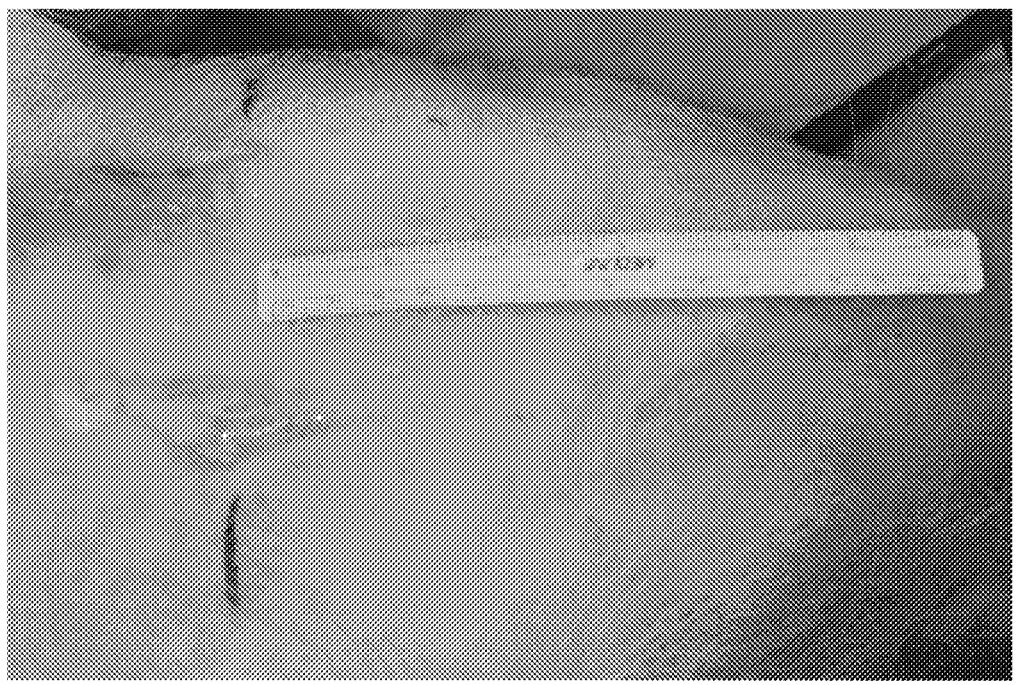
FIG. 28A depicts an injection site for porcine parapharyngeal and neck fat pads.
Figure 28B:
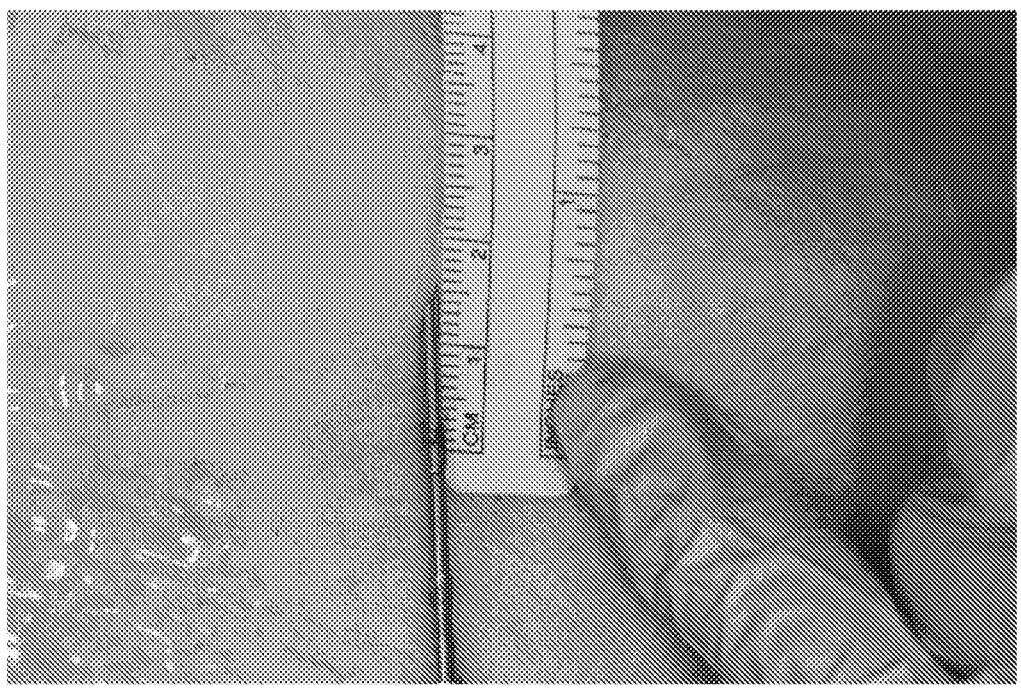
FIG. 28B depicts the injection depth.
Figure 28C:
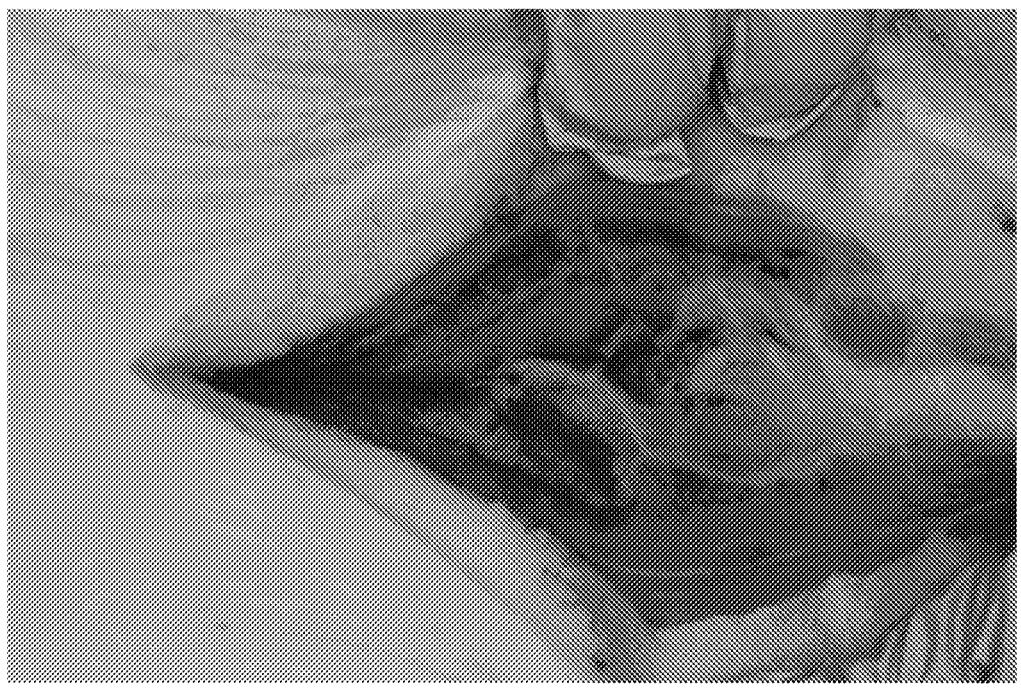
FIGS. 28C and 28D depict the localization of the slurry (containing ink) within the parapharyngeal and neck fat pads.
Figure 28D:
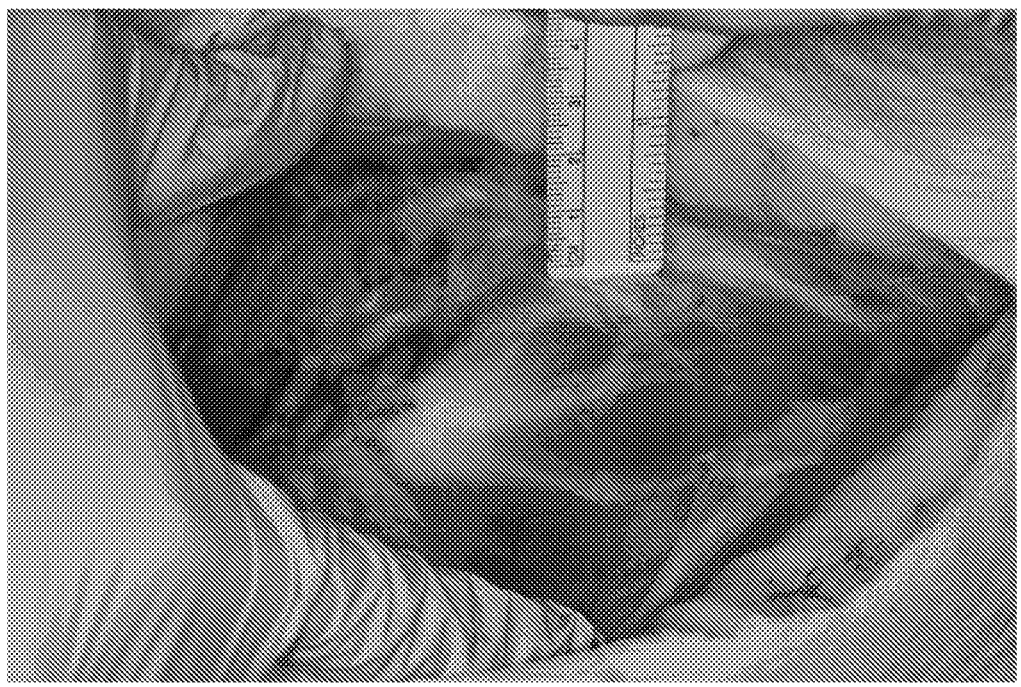
Figure 29A:
FIGS. 29A-29K are photographs depicting the result of various slurry compositions into swine.
Figure 29B:
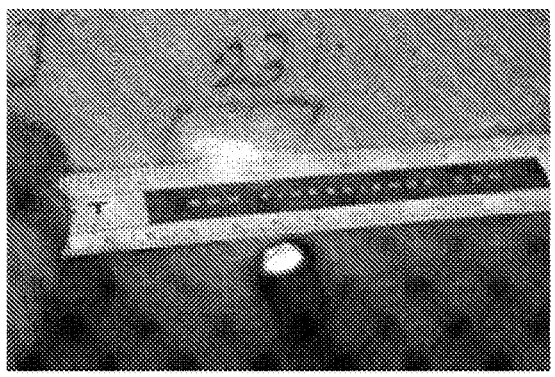
Figure 29C:
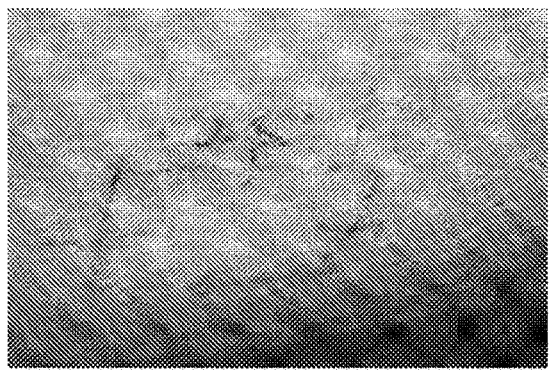
Figure 29D:
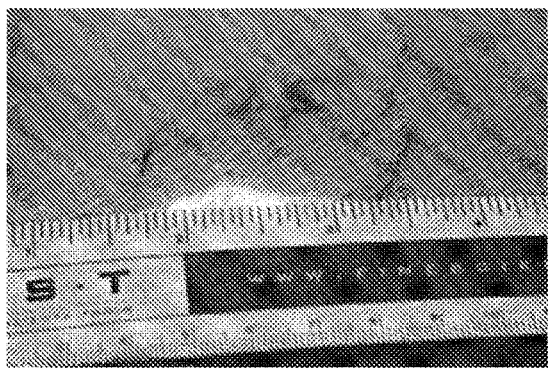
Figure 29E:
Figure 29F:
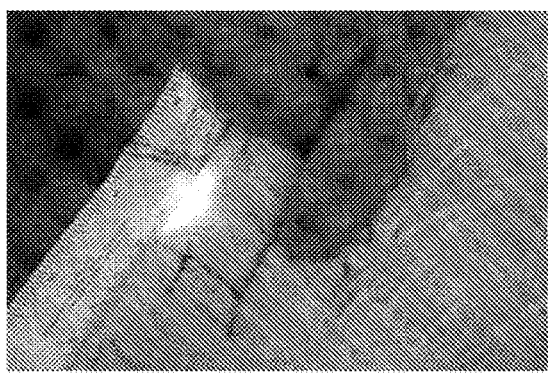
Figure 29G:
Figure 29H:
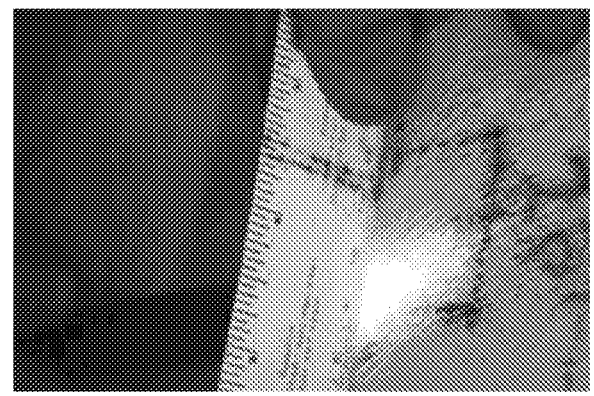
Figure 29I:
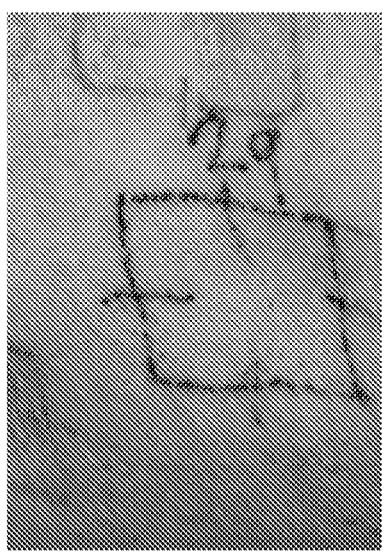
Figure 29J:
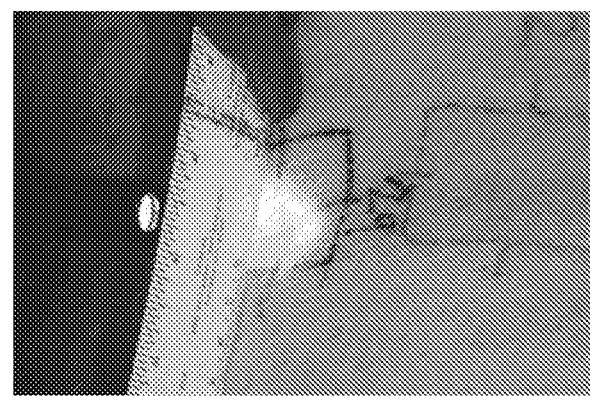
Figure 29K:
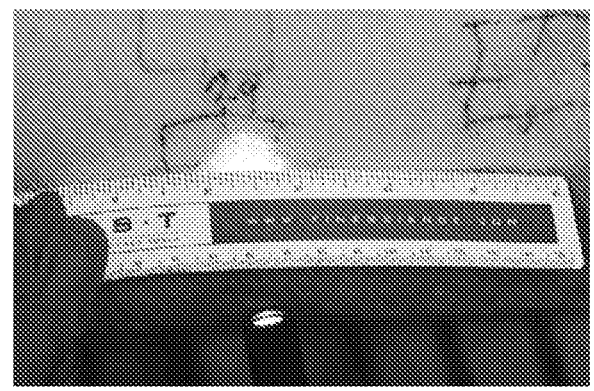

At time of necropsy in a swine, Applicant demonstrated that slurry can be delivered to the parapharyngeal fat pads using ultrasound guidance and non-invasive injection. Several drops of black india ink (tattoo ink) were added to a slurry composed of 10% glycerol (by weight) in normal saline. The addition of ink enables visualization of deposition of the slurry. Ultrasound imaging was used to visualize the area to be injected. FIG. 28A depicts the injection site. FIG. 28B depicts the injection depth. FIGS. 28C and 28D depict the localization of the slurry (containing ink) within the parapharyngeal fat pads.

Dermal Thickening

Figure 34A:
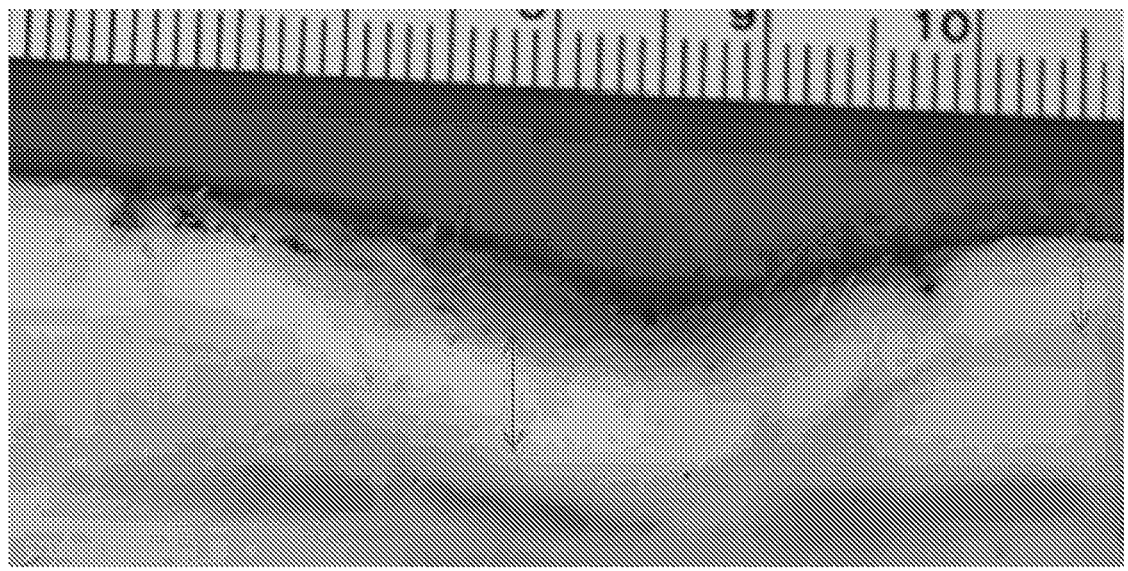
FIGS. 34A and 34B provides images of gross biopsies of swine taken at time of sacrifice three months post-procedure and showing a visible dermal thickening in the treated region.
Figure 34B:
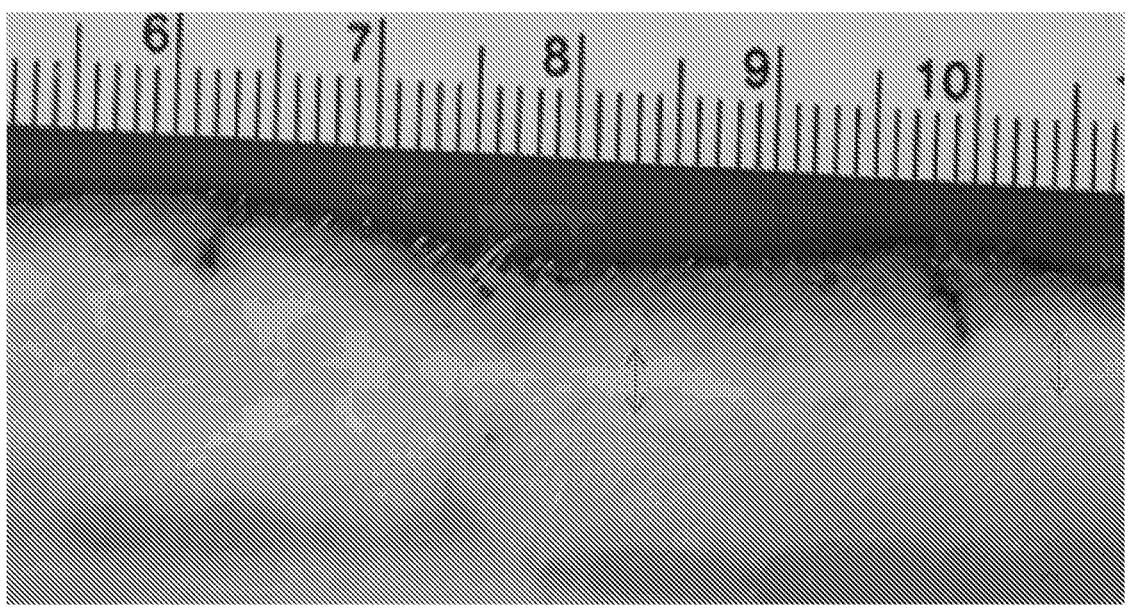

FIGS. 34A and 34B provides images of gross biopsies taken at time of sacrifice three months post-procedure. FIG. 34A is a cross-section of tissue at a site injected with with a cold slurry of normal saline+10% glycerol. FIG. 34B is a cross-section of tissue at a site injected with a room temperature solution of normal saline+10% glycerol. In the site receiving cold slurry injection shown in FIG. 34A, dermal thickening of 38.1% was noted at the time of sacrifice. In contrast, the site receiving a room temperature solution of the same composition as slurry shown in FIG. 34A did not show any change in the thickness of the dermis.

Figure 35A:
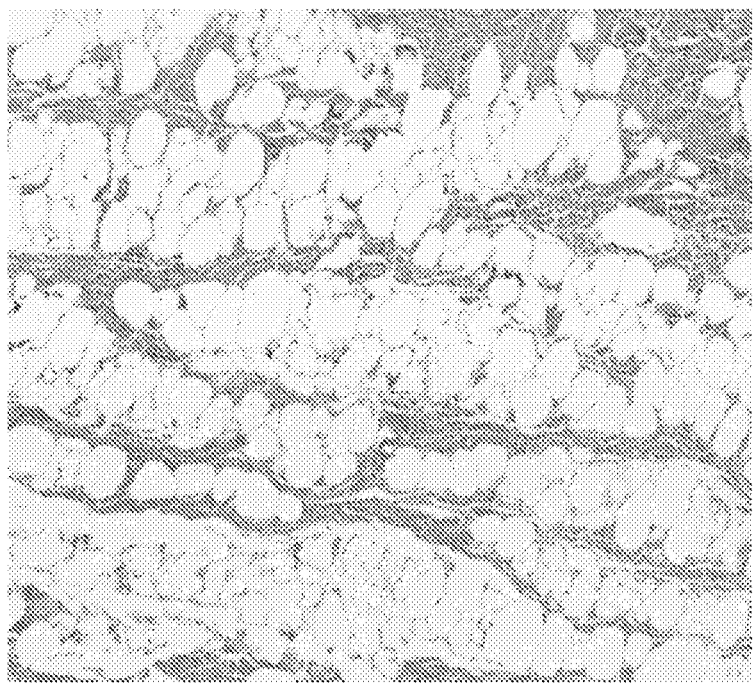
FIGS. 35A and 35B provide images of histology of swine taken at time of sacrifice three months post-procedure and stained with hematoxylin and eosin (H&E).
Figure 35B:
Figure 37A:
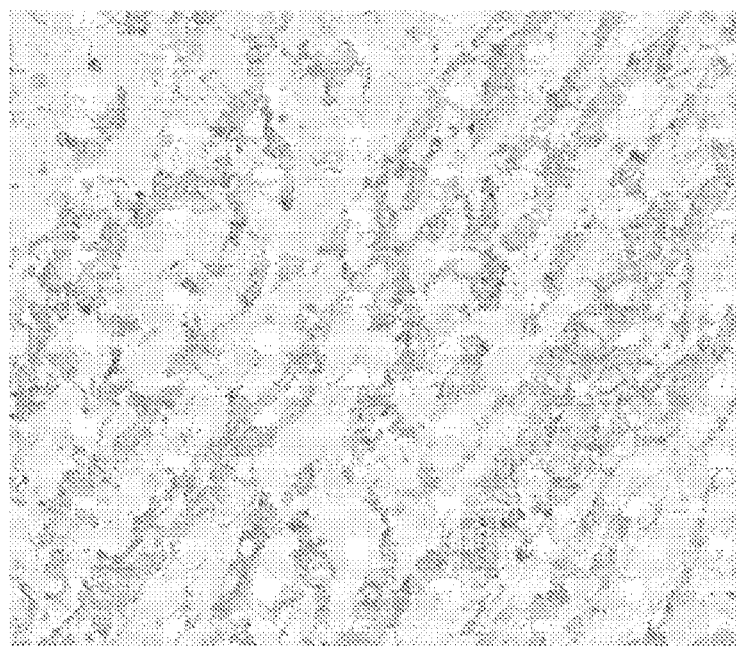
FIGS. 37A and 37B provide images of immunohistochemical (IHC) staining for type I collagen taken at time of sacrifice three months post-procedure.
Figure 37B:
Figure 38A:
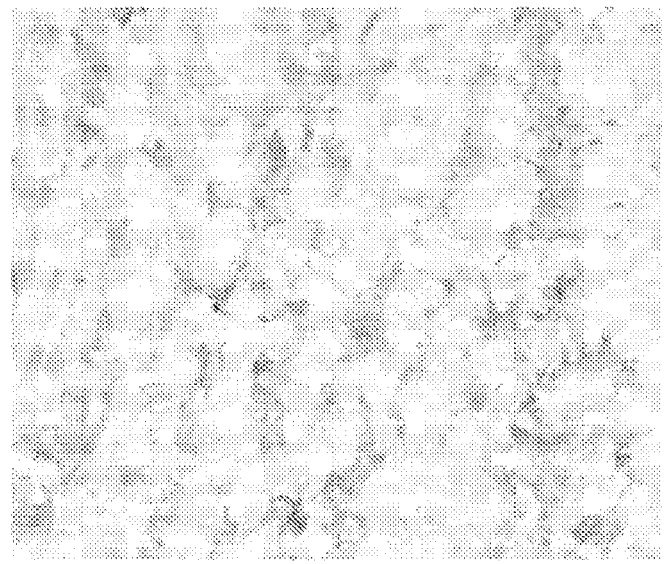
FIGS. 38A and 38B provide images of immunohistochemical (IHC) staining for type III collagen taken at time of sacrifice three months post-procedure.
Figure 38B:
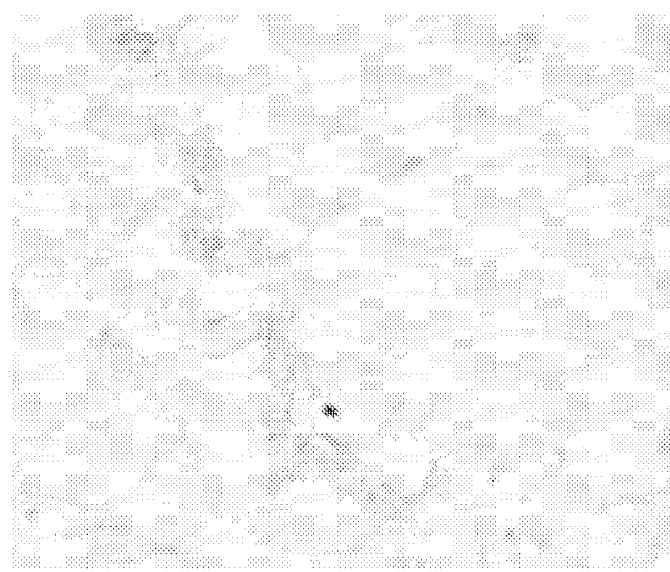

FIGS. 35A and 35B provide images of histology taken at time of sacrifice three months post-procedure and stained with hematoxylin and eosin (H&E). In the site receiving cold slurry injection in FIG. 35A, septal thickening and increase collagen was noted at the time of sacrifice. In contrast, the untreated site in FIG. 35B demonstrates normal connective tissue morphology with thin septae and no collagen production noted. FIGS. 37A and 37B provide images of immunohistochemical (IHC) staining for type I collagen taken at time of sacrifice three months post-procedure. FIGS. 38A and 38B provide images of immunohistochemical (HC) staining for type III collagen taken at time of sacrifice three months post-procedure.

In Vivo Rat Experiments

Safety and Tolerability Experiments

Rats were injected with a variety of slurry formulations detailed in Table 7 to assess safety and tolerability of the slurries. All of the animals tolerated the injection with no sign of infection, ulceration, necrosis or side effects.

TABLE 7

Slurry Injections

| Slurry Composition | Temp. | Amount |
|---|---|---|
| Normal Saline + 20% Glycerol | −5.2° C. | 15 cc |
| Normal Saline + 30% Glycerol | −6.7° C. | 10 cc |
| Normal Saline + 30% Glycerol | −7.4° C. | 9-10 cc |
| Normal Saline + 40% Glycerol | −8.2° C. | 9-10 cc |
| Normal Saline + 40% Glycerol | −10.1° C. | 9-10 cc |
| 5% PEG in LR (Lactated Ringer's Solution) + 5% Dextrose | −0.6° C. | 10 cc |
| 5% PEG in LR + 5% Dextrose | −0.8° C. | 10 cc |
| 5% PEG in LR + 5% Dextrose | −0.2° C. | 10 cc |
| Room Temp. 5% PEG in LR + 5% Dextrose | 8° C. | 10 cc |
| 5% TWEEN ® 20 in LR + 5% Dextrose | −0.6° C. | 10 cc |
| 5% TWEEN ® 20 in LR + 5% Dextrose | −0.6° C. | 10 cc |
| 5% TWEEN ® 20 in LR + 5% Dextrose | −0.6° C. | 10 cc |
| Room Temp. 5% TWEEN ® 20 in LR + 5% Dextrose | 16.0° C. | 8 cc |
| Hetastarch in LR | 0.3° C. | 10 cc |
| Hetastarch in LR | 0.3° C. | 10 cc |
| Hetastarch in LR | 0.4° C. | 10 cc |
| Room Temp. Hetastrach in LR | 15.4° C. | 10 cc |

Comparison of Efficacy of Slurry Compositions and Temperatures

Figure 19:
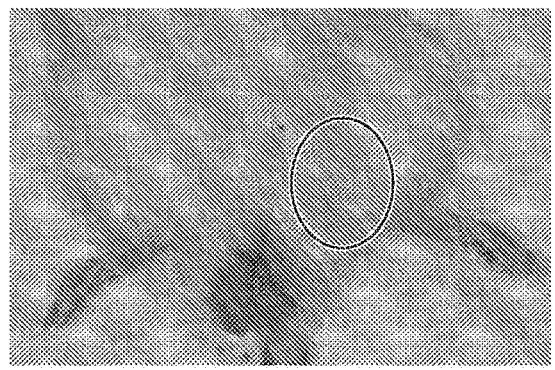
FIG. 19 depicts an injection site in the area of the left inguinal fat pad in adult Sprague-Dawley rats.

Adult Sprague-Dawley rats were anesthetized and given a single subcutaneous injection of 10 cc of either cold slurry or a room temperature fluid of same composition as cold slurry. The injection was given in the area of the left inguinal fat pad as depicted in the encircled area in FIG. 19. The right side was not injected and used as control.

Three slurry compositions were tested in this experiment: (a) 6% hetastarch in lactated Ringer's solution, (b) 5% TWEEN® 20 (polysorbate 20) in lactated Ringer's solution plus 5% dextrose and (c) 5% polyethylene glycol (PEG) in lactated Ringer's solution plus 5% dextrose.

Lactated Ringer's solution is a commonly used intravenous fluid that is isotonic. It is composed of 120 mEq sodium ions, 109 mEq chloride ions, 28 mEq lactate, 4 mEq potassium ions, and 3 mEq calcium ions. Thus, it differs from normal saline in its composition.

Figure 20A:
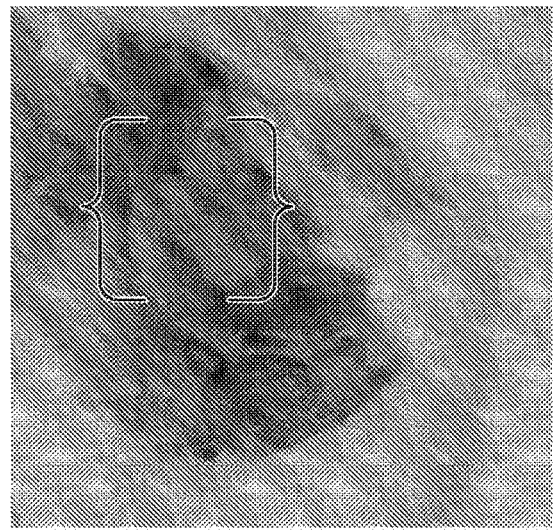
FIGS. 20A, 20B, and 20C depicts the result of injection of room temperature hetastarch solutions, injection of cold hetastarch slurry, and no injection in a control site, respectively, in adult Sprague-Dawley rats.
Figure 20B:
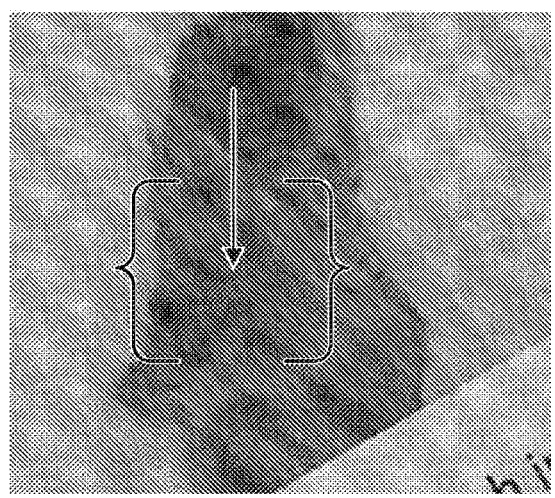
Figure 20C:
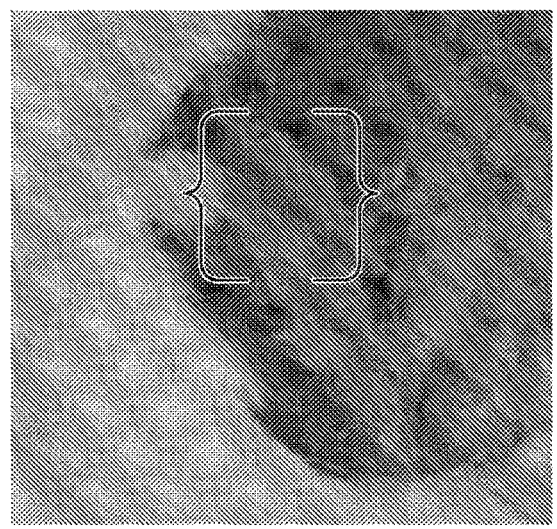
Figure 20D:
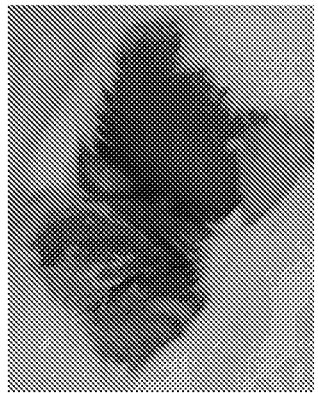
FIGS. 20D, 20E, 20F, and 20G depict tissue surrounding the injection site demonstrating no effects on muscle or surrounding tissue.
Figure 20E:
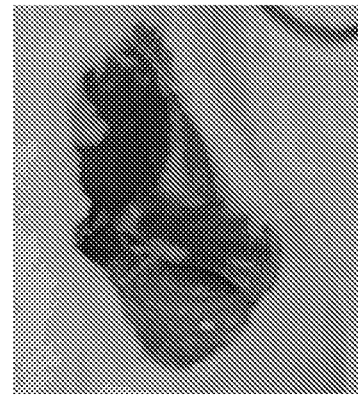
Figure 20F:
Figure 20G:
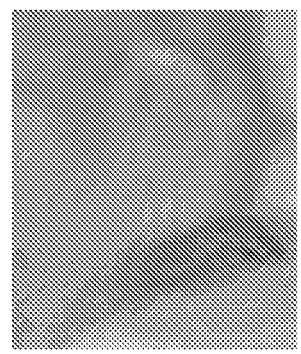

FIGS. 20A and 20B depict the result of injections of 6% hetastarch in lactated Ringer's solution at room temperature (+15.4° C.) and cold slurry (+0.3° C.), respectively. FIG. 20C depicts the control (not injected) side. FIGS. 20D-20G depict tissue surrounding the injection site demonstrating no effects on muscle or surrounding tissue.

All photographs were taken 10 days post-injection procedure. Cold hetastarch slurry resulted in disruption of normal fat morphology (as depicted with a thin arrow). Adipose tissue is highlighted in brackets. Room temperature slurry did not show disruption of fat tissue on gross observation. Cold slurry did not show gross changes in muscle or skin near the injected area. Cooling alone through slurry injection caused the selective disruption of the fat.

Figure 21A:
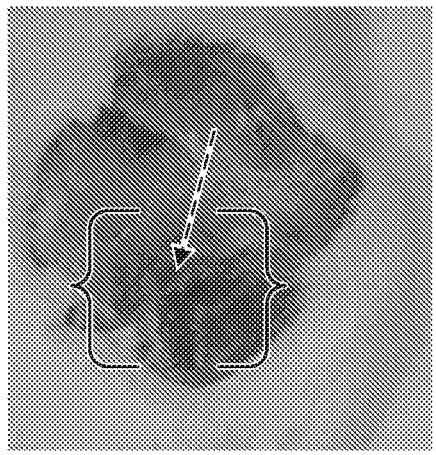
FIGS. 21A and 21B depict the result of injections of 5% TWEEN® 20 (polysorbate 20) in lactated Ringer's solution plus 5% dextrose at room temperature (+16° C.) and cold slurry (0.6° C.), respectively, in adult Sprague-Dawley rats.
Figure 21B:
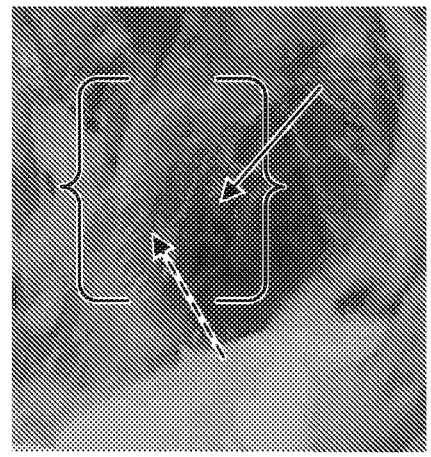
Figure 21C:
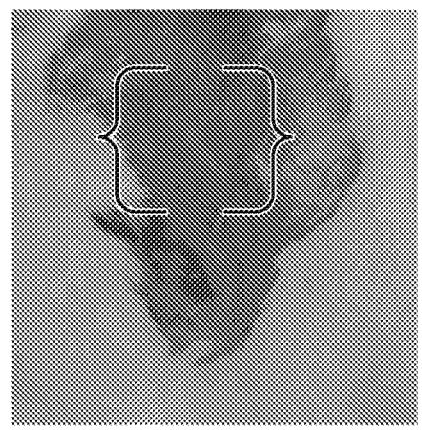
FIG. 21C depicts the control (not injected) side.
Figure 21D:
FIGS. 21D, 21E, 21F, and 21G depict tissue surrounding the injection site demonstrating no effect on muscle or surrounding tissue.
Figure 21E:
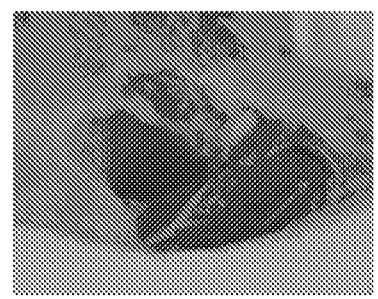
Figure 21F:
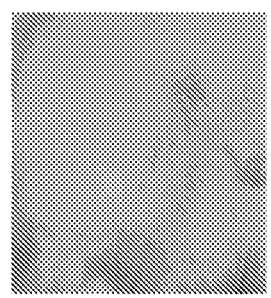
Figure 21G:
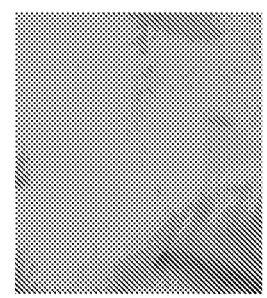

FIGS. 21A and 21B depict the result of injections of 5% TWEEN® 20 (polysorbate 20) in lactated Ringer's solution plus 5% dextrose at room temperature (+16° C.) and cold slurry (−0.6° C.), respectively, in adult Sprague-Dawley rats. FIG. 21C depicts the control (not injected) side. FIGS. 21D-21G depict tissue surrounding the injection site demonstrating no effect on muscle or surrounding tissue.

Both room temperature and cold slurry disrupted normal adipose morphology relative to control as depicted with the dashed arrow. Adipose tissue is highlighted in brackets. Cold slurry resulted in greater disruption and potentially greater fat loss as depicted with the solid arrow. It is possible that adipocytes are sensitive to detergents in general. Cold slurry did not produce gross changes in muscle or skin.

Figure 22A:
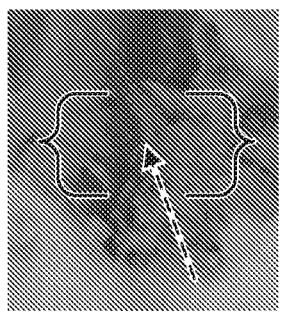
FIGS. 22A and 22B depict the result of injections of 5% polyethylene glycol (PEG) in lactated Ringer's solution plus 5% dextrose at room temperature (+8° C.) and cold slurry (0.8° C.), respectively, in adult Sprague-Dawley rats.
Figure 22B:
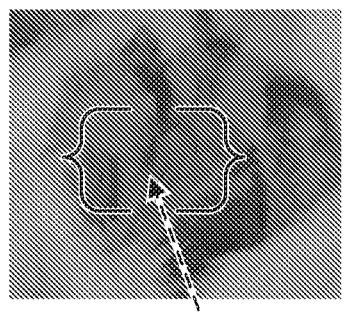
Figure 22C:
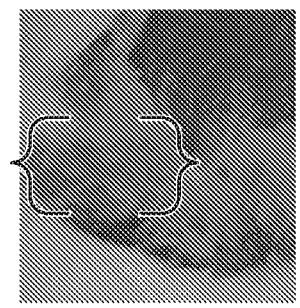
FIG. 22C depicts the control (not injected) side.
Figure 22D:
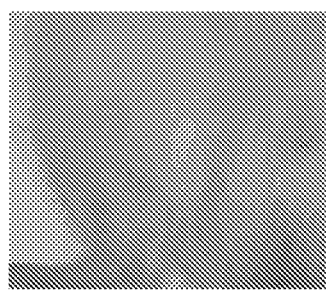
FIGS. 22D, 22E, 22F, and 22G depict tissue surrounding the injection site demonstrating no effect on muscle or surrounding tissue.
Figure 22E:
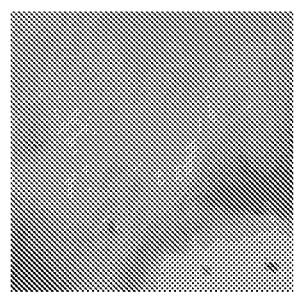
Figure 22F:
Figure 22G:
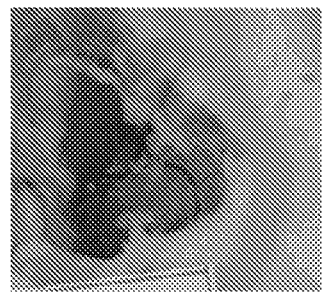

FIGS. 22A and 22B depict the result of injections of 5% polyethylene glycol (PEG) in lactated Ringer's solution plus 5% dextrose at room temperature (+8° C.) and cold slurry (−0.8° C.), respectively, in adult Sprague-Dawley rats. FIG. 19C depicts the control (not injected) side. FIGS. 22D-22G depict tissue surrounding the injection site demonstrating no effect on muscle or surrounding tissue.

Both room temperature and cold slurry disrupted normal adipose morphology as depicted with dashed arrows relative to control. Adipose tissue is highlighted in brackets. PEG acts as a detergent. It is possible that adipocytes are sensitive to detergents in general. Cold slurry did not show gross changes in muscle or skin. It is possible that the single phase liquid also had some cooling effect, as +8° C. is below the point of crystallization of lipids (approximately +14° C.).

These experiments show several results. First, slurries that do not contain glycerol are also capable of disrupting fat. Second, the disruption of tissue is selective for fat; there were no observed gross changes in muscle or overlying skin. Third, in the absence of a lipolytic additive, only cold slurry is capable of disrupting fat, as a cool or room temperature liquid of the same composition as slurry does not result in any changes. The results support the theory that adipocytes may be more sensitive to injury by substances with detergent properties, as mild disruption of adipose tissue was observed in the room temperature variant of slurries containing detergent additives. Fifth, the disruption of tissue was most pronounced in the condition of cold slurry and a detergent additive, providing preliminary evidence that there may be an additive or synergistic effect of slurry and detergent.

Treatment of Visceral Fat

Figure 32A:
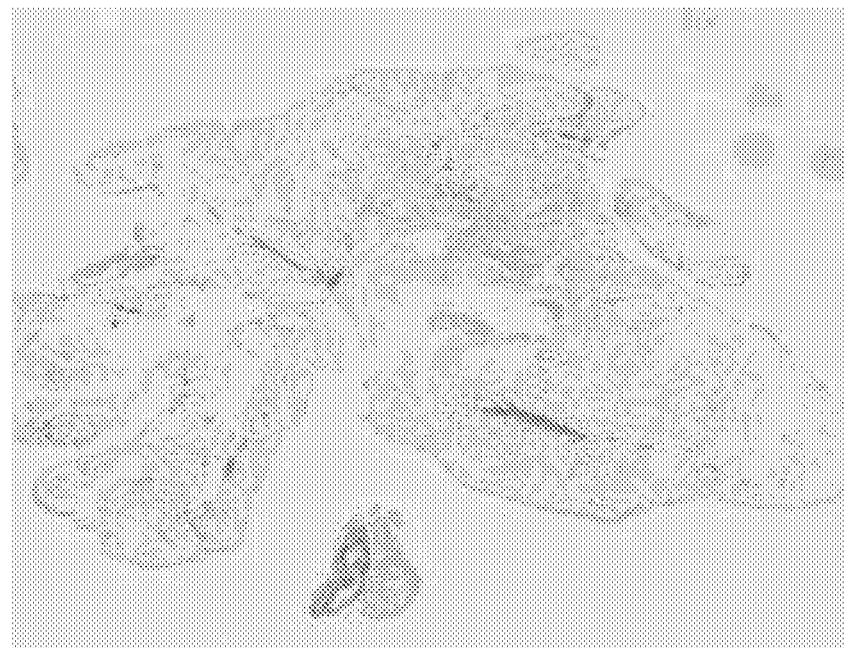
FIGS. 32A, 32B, 32C, and 32D depict histology of the perigonadal visceral fat of obese mice.
Figure 32B:
Figure 32C:
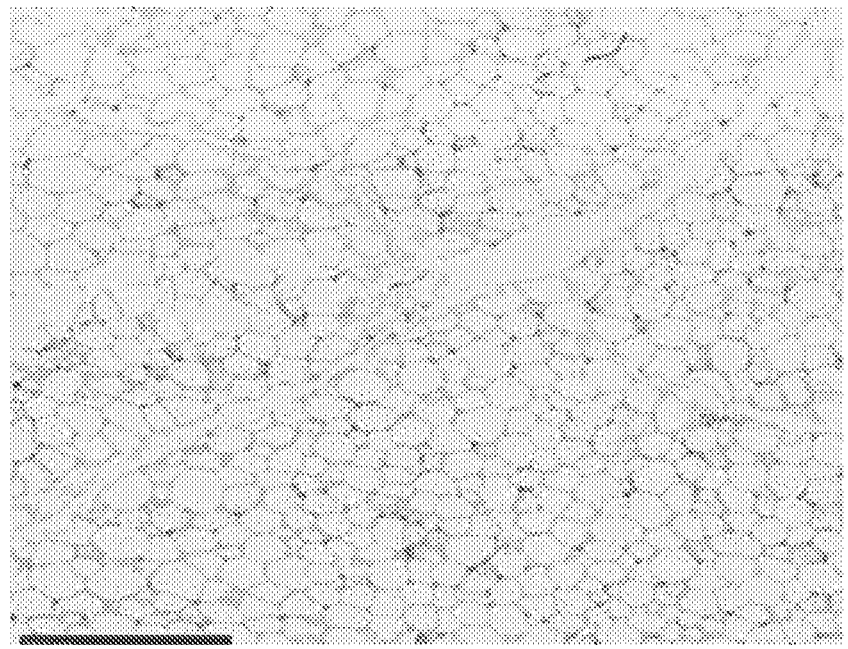
Figure 32D:
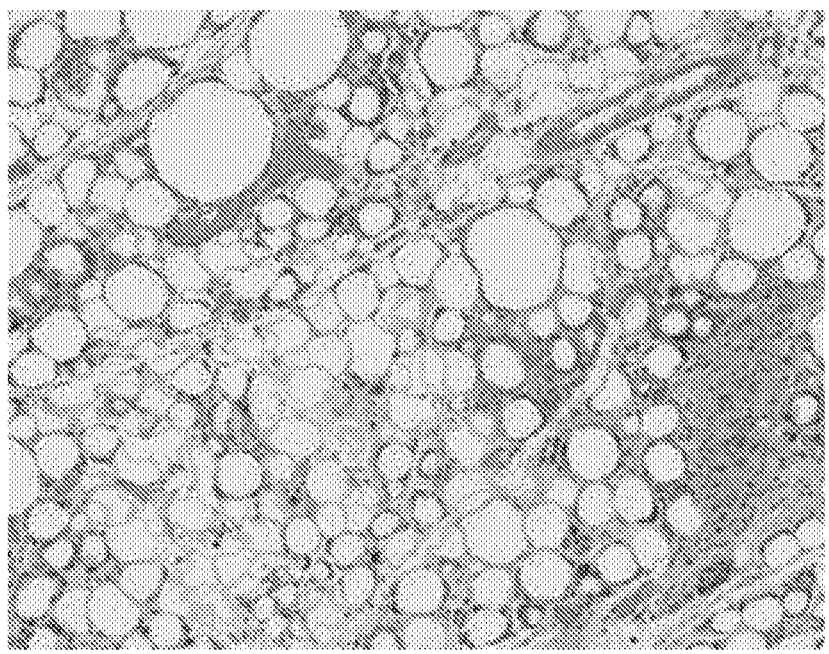

An open laparotomy was performed on obese mice. The perigonadal fat, a visceral fat depot, was exposed and in test mice, was cooled with slurry composed of normal saline. In control mice, normal saline warmed to +37° C. was placed on the visceral fat. The animals were closed using standard surgical technique, and then sacrificed one week post-procedure. The histology of the perigonadal visceral fat at time of sacrifice in the warm saline group is shown in FIGS. 32A and 32C and the histology at the time of sacrifice in the slurry group is shown FIGS. 32B and 32D, respectively. FIGS. 32A and 32C show normal visceral fat morphology in the warmed normal saline group. However, disruption of fat morphology is observed in the saline slurry group depicted in FIGS. 32B and 32D, on both gross histology and high magnification, respectively.

Figure 33:
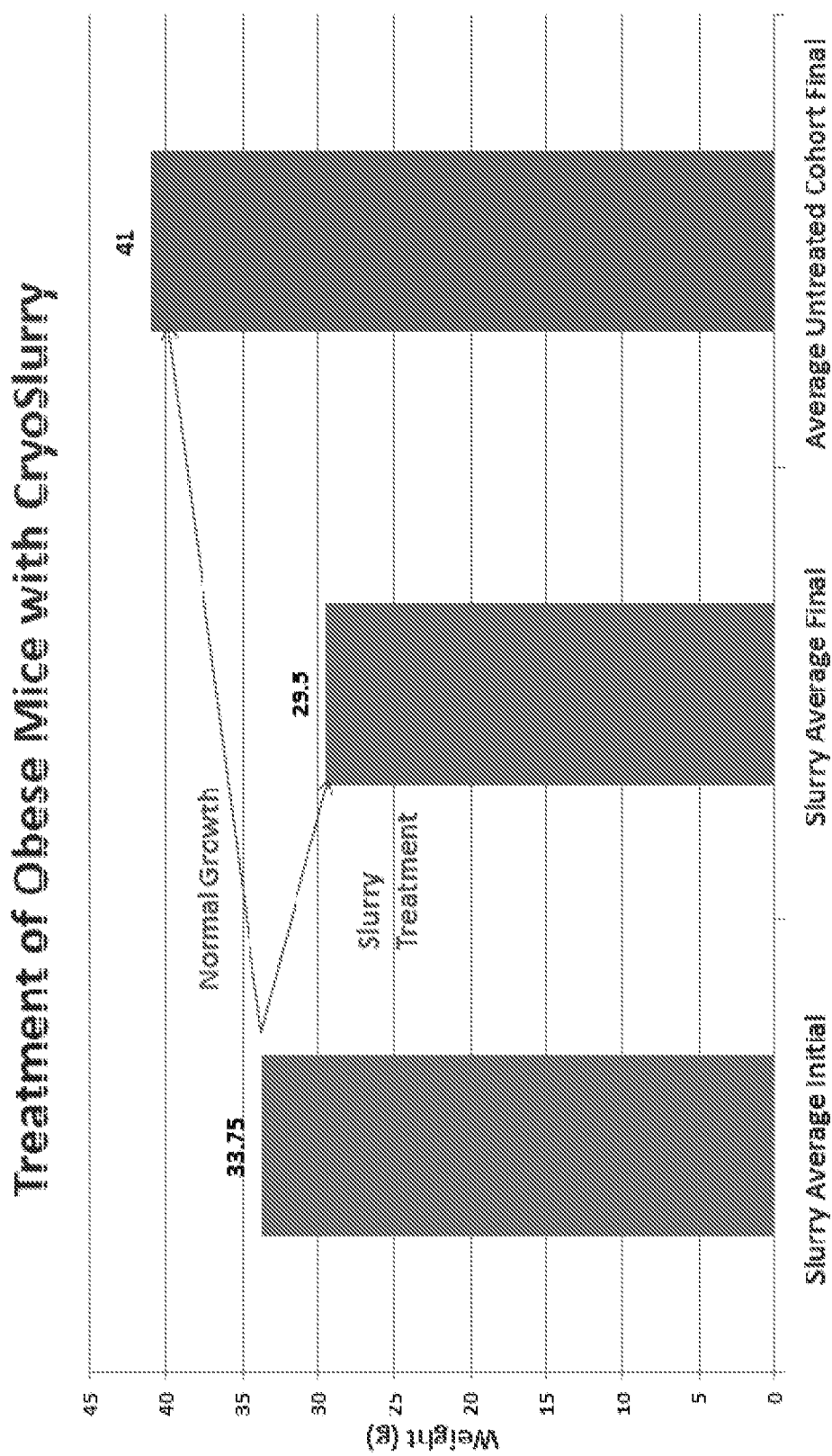
FIG. 33 is a graph of average weight loss of obese mice treated with intraperitoneal injection of cold slurry compared to their untreated cohort.

Referring now to FIG. 33, five obese mice were taken from a larger cohort, anesthetized, weighed, and each administered a 2 cc intraperitoneal injection of slurry. The slurry injected was composed of peritoneal dialysis solution (DIANEAL® available from Baxter International Inc. of Deerfield, Ill.) and 5% glycerol (w/v). The injection temperature was around −1.9° C. The mice were sacrificed 1.5 weeks post injection. At time of sacrifice, both the treated mice and the general cohort were weighed. The mice receiving treatment with slurry lost, on average, 7.9% of their body weight. In contrast, the normal untreated cohort, gained an average of 21.8% of their body weight.

Treatment of Sleep Apnea

Figure 39A:
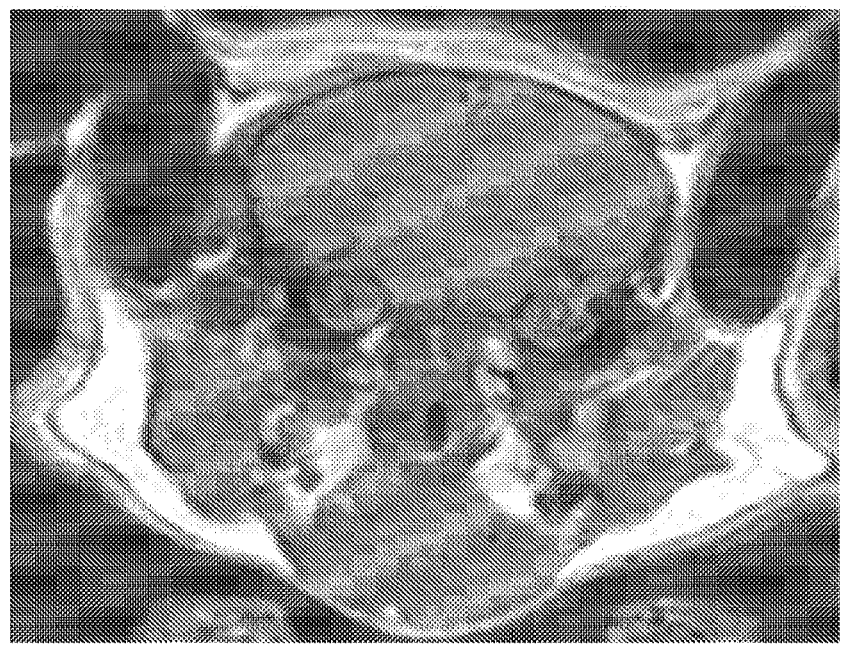
FIGS. 39A and 39B are magnetic resonance (MR) images depicting the cross-sections of a control mouse trachea and adjacent tissue at a baseline and four week follow-up, respectively.
Figure 39B:
Figure 40A:
FIGS. 40A and 40B are magnetic resonance (MR) images depicting the cross-sections of a treated mouse trachea and adjacent tissue at a baseline and four week follow-up, respectively.
Figure 40B:

Referring now to FIGS. 39A-40B, slurry injections were utilized to treat sleep apnea in a mouse model. FIGS. 39A and 39B are magnetic resonance (MR) images depicting the cross-sections of a control mouse trachea and adjacent tissue at a baseline and four week follow-up, respectively. FIGS. 40A and 40B are magnetic resonance (MR) images depicting the cross-sections of a treated mouse trachea and adjacent tissue at a baseline and four week follow-up, respectively. The mouse treated in FIGS. 40A and 40B was injected with slurry at a temperature of −1.9° C.

TABLE 8

Effect of Slurry Injections to Treat Sleep Apnea in Mouse Model

| | Cross-Sectional Area of Trachea | | | Airway Fat |
| --- | --- | --- | --- | --- |
| | Baseline | 4-Week Follow-Up | Change | Change |
| Control | 0.0048 | 0.0029 | −39.6% | +68.0% |
| Treated | 0.0067 | 0.0066 | −1.5% | +45.5% |

Treatment of Vascular Diseases

In general, three swine studies were performed to demonstrate the feasibility, safety, and effectiveness of using injectable slurries to treat vascular diseases. Specifically, the three swine studies targeted pericardial fat, epicardial fat, and thoracic peri-aortic fat. In some non-limiting examples, the success of the following swine studies demonstrates the potential for injectable slurries to be a minimally invasive treatment for vascular diseases including, for example, cardiovascular diseases such as coronary artery disease.

First Swine Study

Figure 41:
FIG. 41 illustrates a slurry injection into epicardial fat around coronary arteries and surrounding a beating swine heart.

A 66 kg Yorkshire pig was utilized for the study. Pericardial fat, epicardial fat including right atrioventricular (A-V) groove fat pad, and thoracic fat were injected with a slurry having an initial temperature of −4° C. The pericardial fat was injected with 10 ml of slurry, the epicardial fat was injected with 10 ml of slurry and 5 ml of slurry, and the thoracic peri-aortic fat tissue was injected with 5 ml of slurry. A thermocouple was placed in the tissue to measure adipose tissue temperature before and after injection (see, e.g., FIG. 41 for injection into epicardial fat tissue on a beating swine heart).

Figure 42:
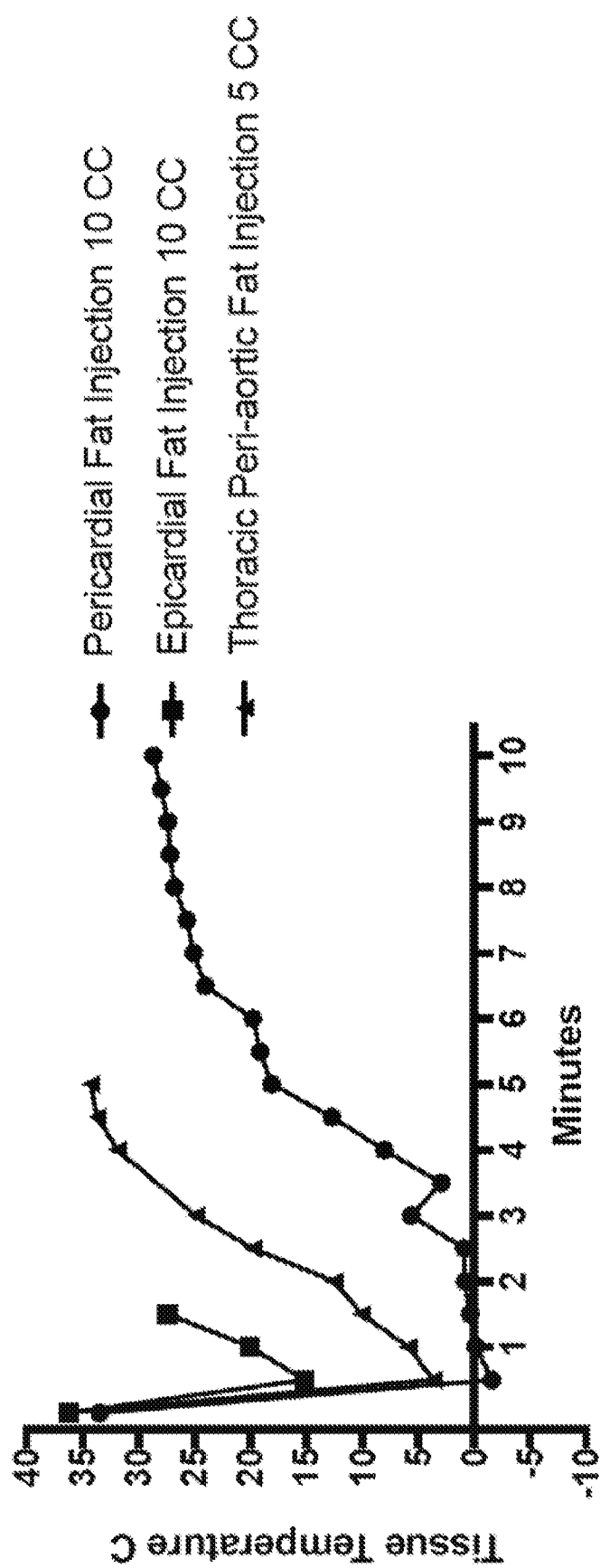
FIG. 42 is a graph illustrating temperature in swine pericardial fat, swine epicardial fat, and swine thoracic peri-aortic fat as a function of time following a slurry injection.

FIG. 42 illustrates the results of the injection into the various adipose tissues before and after the injection of slurry. In all cases, the adipose tissues showed a rapid decrease in temperature following injection of the slurry. For example, the pericardial fat temperature dropped below 0° C. in less than a minute after injection with the slurry, and maintained a temperature generally around 0° C. for between two and three minutes after injection of slurry.

Second Swine Study

A 71 kg Yorkshire pig was utilized for the experiment. Pericardial fat was exposed using a left thoracotomy approach and was injected with 45 ml of slurry having an initial temperature of −5.7° C. In addition, epicardial adipose tissue was injected with 15 ml and 20 ml of slurry having an initial temperature of −5° C., and periappendigial fat was injected with 30 ml of slurry having an initial temperature of −5° C. The animal was hemodynamically stable throughout all of the various slurry injections performed during the experiment.

Figure 43:
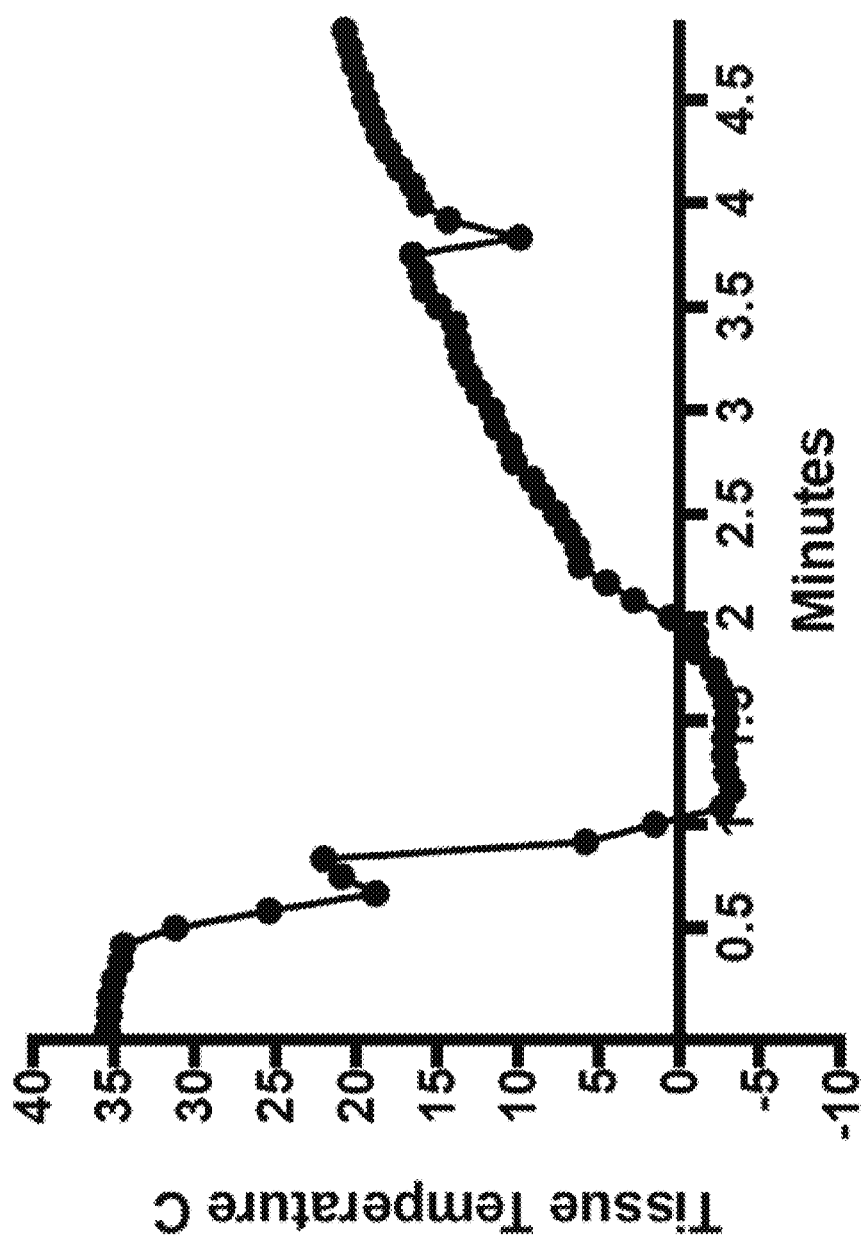
FIG. 43 is a graph illustrating temperature in swine pericardial fat as a function of time following a slurry injection.

FIG. 43 illustrates the temperature of the pericardial fat tissue before and after the 45 ml slurry injection. The pericardial fat temperature decreased to −3.9° C. within 1 minute of injection, and maintained a temperature at or below 0° C. for approximately two minutes after injection.

Third Swine Study

A 80 kg female Yorkshire pig was utilized for the experiment. Pericardial adipose tissue was exposed and two cycles of slurry injections of 14 cubic centimeters (cc) each with one minute apart. The slurry temperature was −4.8° C. at the time of injection. Two metal clips were applied at the injection sites. No hemodynamic instability or any unwanted side effects were noted during and after injection.

Figure 44:
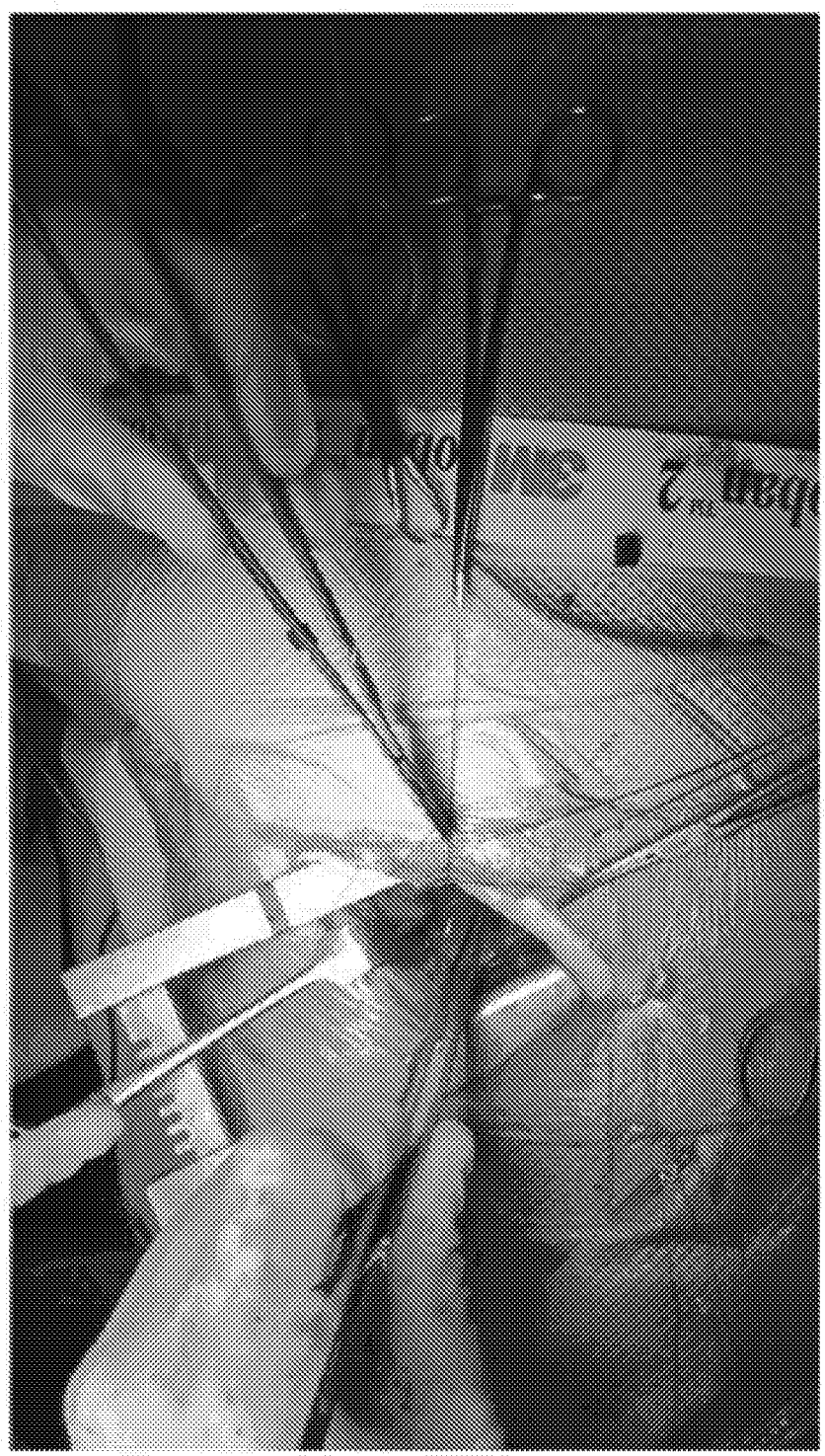
FIG. 44 illustrates a slurry injection into swine perivascular adipose tissue following a left thoracotomy.

In addition, epicardial atrioventricular (A-V) groove fat pad was injected. Two injections of 12 cc and 18 cc were performed with the slurry at a temperature of −5.3° C. and −5.2° C., respectively, at the time of injection. Two clips were applied to the periphery of the injection site and inferior to the left atrial appendage in the left A-V groove (see, e.g., FIG. 44).

During the slurry injections, the animal tolerated the procedure in the operating room by showing no signs of hemodynamic instability or cardiac arrhythmia. As such, deliver slurry to adipose tissue around the heart was safe and tolerated. In addition, the slurry injections brought the adipose tissue close to or below 4° C., which is cold enough to remove adipose tissue. Further, histology after the procedures did not show any sign of scaring or adverse effects to the surrounding tissue.

Adipose Tissue Dose Response Experiments

Yorkshire female pigs weighing between 52-85 kg and 3-6 months old were utilized for the experiments. Slurry and control melted slurry were directly injected into subcutaneous fat ~2 cm deep at various injection sites. The slurry was comprised of normal saline (0.9% sodium chloride) and 10% glycerol, and was injected through a 15 gauge needle.

Ultrasound imaging was used to measure fat thickness (SonoSite 10; 7.5 MHz linear transducer, SonoSite Inc, Bothell, Wash.) at baseline and 8 weeks post treatment. Side-lit photographs of skin indentations were taken at each site to visually demonstrate subcutaneous adipose tissue reduction. Adipose tissue volume loss was obtained by applying Tegaderm™ (3M Medical) tightly over the skin indentation sites and surrounding skin, and measuring the volume of water needed to fill the skin indentation.

Figure 45:
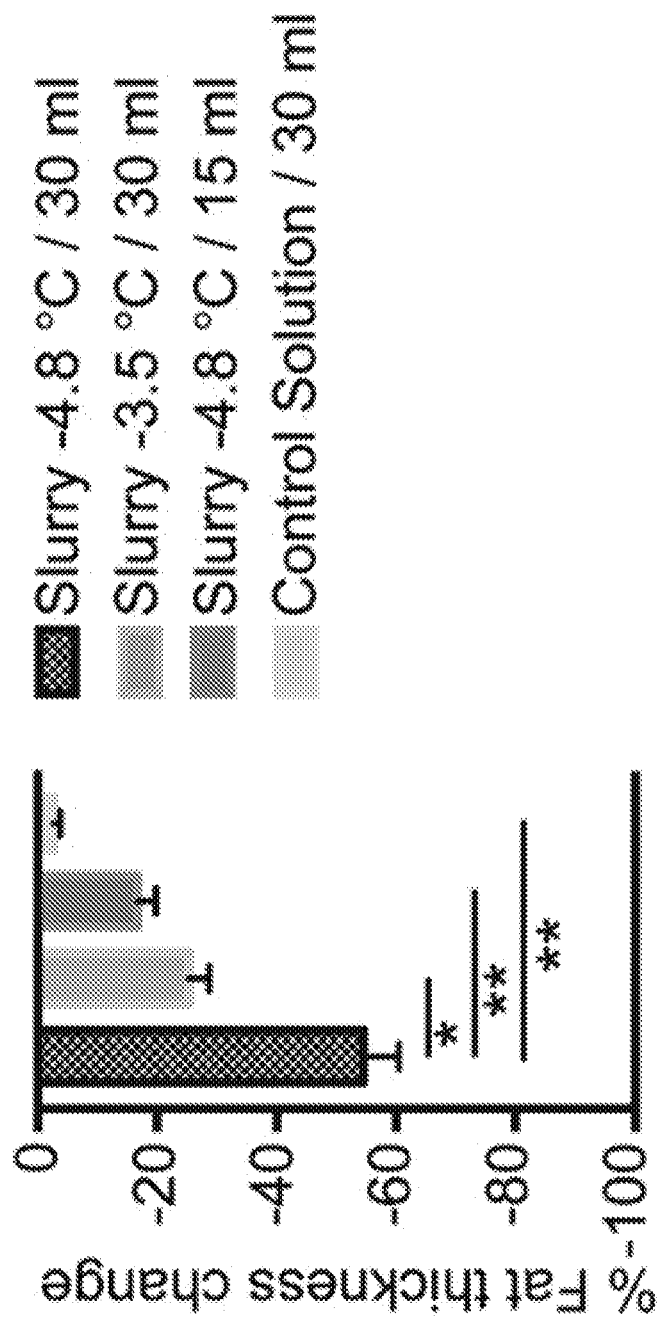
FIG. 45 is a graph illustrating percent change in adipose tissue thickness following slurry injections with varying ice contents and volumes.

In general, the volume of ice injected is equal to the slurry volume times its volume fraction of ice. The influence of slurry volume and slurry ice content on the amount of fat thickness was evaluated by injecting multiple sites with two different volumes (15 ml, 30 ml) at two different ice contents (20% and 40% by volumes, corresponding to −3.5° C. and −4.8° C. slurries, respectively). Comparisons were made of reduction of fat thickness (see Table 9, below, which shows the effect of physical modification of slurry on the amount of subcutaneous adipose tissue reduction in each treatment group). Gross pathology measurements were used for the quantification of the thickness of fat loss because this method allows for animal growth correction to be included in the measurements. Sites in Group 1, treated with 30 ml of slurry with 40% ice content, had total of 12 cm$^3$ ice injected and showed the most reduction in fat thickness (54.5±5.9%). As illustrated in FIG. 45, sites in Group 2, treated with 15 ml of slurry with 40% ice content), and in Group 3, treated with 30 ml of slurry with 20% ice content, both with a total of 6 cm$^3$ ice injected, showed less reduction in fat thickness in comparison to Group 1 (25.3±3.4% vs 16.7±3%; p<0.05 and p<0.001 respectively, Ordinary one-way ANOVA followed by Dunnett's multiple comparison test). There was no significant difference in fat loss between Group 2 and 3.

Figure 46:
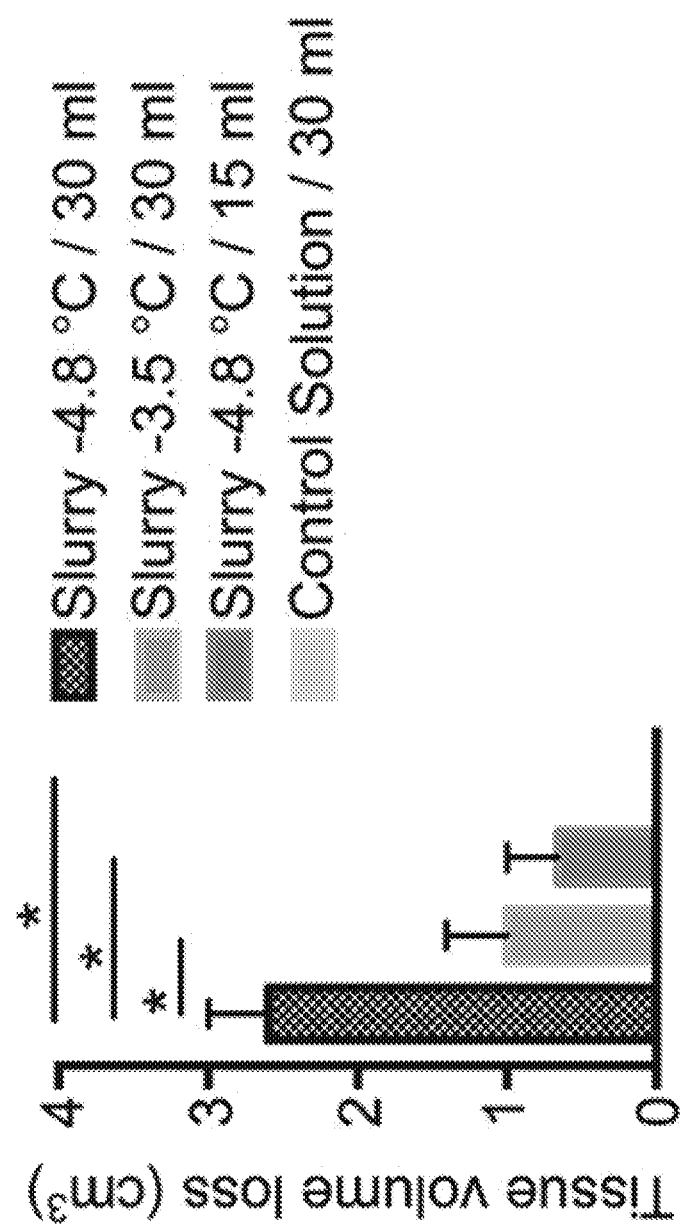
FIG. 46 is a graph illustrating a total volume loss of adipose tissue following slurry injections with varying ice contents and volumes.

After the experiments, no scarring or damage to tissue surrounding the injection sites was observed. As illustrated in FIG. 46, the volume of fat loss in these dose-response experiments, was 2.6±0.4 cm$^3$ in Group 1 sites; 1.0±0.4 cm$^3$ in Group 2 sites; and 0.7±0.3 cm$^3$ in Group 3 sites. Fat volume loss in Group 2 and Group 3 were significantly less than Group 1, and there was again no significant difference between Group 2 and Group 3 sites. Quantitatively, the volume of adipose tissue loss was about one-fifth of the volume of the injected ice content. These dose-response studies highlight the importance of total ice volume for the biologic effect of the slurry, rather than the volume of slurry. Injected ice volume is the major determinant of how much adipose tissue will be lost, and the dosing results disclosed herein may be extrapolated to calculate a desired ice volume for a predetermined amount of adipose tissue removal.

TABLE 9

Thickness and Volume Fat Loss Correlated with Volume and Fractional Ice Content of the Injected Slurry

|  | Group 1 | Group 2 | Group 3 | Control |
| --- | --- | --- | --- | --- |
| Temperature (° C.) | −4.8 | −4.8 | −3.5 | 22 |
| Volume of Injection (ml) | 30 | 15 | 30 | 30 |
| Fractional Ice Content % | 40 | 40 | 20 | 0 |
| Total Ice Volume (cm$^3$) | 12 | 6 | 6 | 0 |
| Gross Fat Thickness Reduction % | 54.5 ± 15.5 | 25.3 ± 6.8 | 16.7 ± 5.2 | 2.64 ± 1.9 |
| Volume of fat loss (cm$^3$) | 2.6 ± 0.9 | 1 ± 0.8 | 0.7 ± 0.6 | 0 ± 0.0 |

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

We claim:

1. A method of transporting and preparing an injectable ice slurry for administration to a patient at a point of care, the method comprising:
preparing a pre-mixed liquid comprising water and an additive;
placing the pre-mixed liquid into a container, wherein the container comprises a sealed internal volume and a sterile barrier;
transporting the container comprising the pre-mixed liquid to the point of care;
transforming the pre-mixed liquid into the injectable ice slurry at the point of care without breaking the sterile barrier of the container; and
administering the injectable ice slurry to the patient at the point of care.

2. The method of claim 1, wherein the additive is a freezing point depressant.

3. The method of claim 2, wherein the freezing point depressant is glycerol.

4. The method of claim 1, wherein the pre-mixed liquid further comprises a salt.

5. The method of claim 4, wherein the salt is sodium chloride.

6. The method of claim 1, wherein an amount of the additive is selected from the group consisting of less than about 20% (w/w) of the pre-mixed liquid, between about 20% (w/w) and about 30% (w/w) of the pre-mixed liquid, and between about 30% (w/w) and about 40% (w/w) of the pre-mixed liquid.

7. The method of claim 1, wherein the water constitutes about 80% (w/w) of the pre-mixed liquid.

8. The method of claim 1, wherein the pre-mixed liquid is configured to be transported to and stored at the point of care in a non-temperature-controlled environment in the container prior to transforming the pre-mixed liquid into the injectable ice slurry.

9. The method of claim 1, wherein the transforming comprises modifying the pre-mixed liquid, wherein the modifying is selected from the group consisting of a mechanical agitation, a thermal shock, a vibration, an ultrasonic energy, a manual shaking, a freezing, a thawing, and a combination thereof.

10. The method of claim 1, wherein the transforming comprises placing the container into a freezer at the point of care.

11. The method of claim 1, wherein the injectable ice slurry comprises a plurality of ice particles and is configured to flow through a lumen.

12. The method of claim 1, wherein transforming the pre-mixed liquid into the injectable ice slurry comprises monitoring a temperature of the pre-mixed liquid while transforming the pre-mixed liquid into the injectable ice slurry.

13. The method of claim 12, wherein monitoring the temperature of the pre- mixed liquid comprises reading a temperature measuring device located on a surface of or external to the container.

14. The method of claim 13, wherein the temperature measuring device is a liquid crystal thermometer.

15. The method of claim 12, wherein monitoring the temperature of the pre- mixed liquid includes reading a temperature measuring device located inside of the container.

16. The method of claim 1, wherein the injectable ice slurry is administered to the patient at the point of care directly from the container without breaking the sterile barrier of the container after the transforming and prior to the administration.

17. A method of transporting a container comprising a pre-mixed liquid to a point of care, the method comprising:
preparing the pre-mixed liquid, wherein the pre-mixed liquid comprises water and a freezing point depressant;
placing the pre-mixed liquid into the container, wherein the container comprises a sealed internal volume and a sterile barrier; and
transporting the container comprising the pre-mixed liquid to the point of care, wherein the pre-mixed liquid is transformed into an injectable ice slurry at the point of care without breaking the sterile barrier of the container, and wherein the injectable ice slurry is configured to be administered to a patient at the point of care.

18. The method of claim 17, wherein the freezing point depressant is glycerol.

19. The method of claim 17, further comprising transforming the pre-mixed liquid into the injectable ice slurry by placing the container into a freezer at the point of care.

20. The method of claim 17, wherein the injectable ice slurry comprises between about 0.1% and 1%, between about 1% and 10%, between about 10% and about 20%, between about 20% and about 30%, between about 30% and about 40%, between about 40% and about 50%, between about 50% and about 60%, between about 60% and about 70%, or greater than about 50% of the slurry by weight.

21. The method of claim 17, wherein the injectable ice slurry is administered to the patient via direct injection into a tissue region.

22. The method of claim 17, wherein the container comprises a visible temperature indicator, wherein the visible temperature indicator is configured to:
visually indicate a temperature of the pre-mixed liquid; and
dynamically track the temperature over time.

23. A method of administering an injectable ice slurry at a point of care to a patient, the method comprising:
receiving at the point of care a container comprising:
a pre-mixed liquid disposed in a sealed internal volume; and
a sterile barrier;
transforming the pre-mixed liquid into the injectable ice slurry without breaking the sterile barrier of the container; and
administering the injectable ice slurry to the patient, wherein the pre-mixed liquid comprises water and a freezing point depressant.

24. The method of claim 23, wherein the freezing point depressant is glycerol, and wherein the pre-mixed liquid further comprises sodium chloride or a derivative thereof.

25. The method of claim 23, wherein an amount of the freezing point depressant is selected from the group consisted of about 30% (w/w) of the pre-mixed liquid, about 20% (w/w) of the pre-mixed liquid, and about 10% (w/w) of the pre-mixed liquid.

26. The method of claim 23, wherein the container is received in a sealed state configured to maintain a sterility of the pre-mixed liquid and of the injectable ice slurry prior to the administration of the injectable ice slurry to the patient.

27. The method of claim 23, wherein transforming the pre-mixed liquid into the injectable ice slurry comprises monitoring a temperature of the pre-mixed liquid.

28. The method of claim 27, wherein monitoring the temperature of the pre-mixed liquid comprises reading a temperature measuring device located on a surface of or external to the container.

29. The method of claim 28, wherein the temperature measuring device is a liquid crystal thermometer.

30. The method of claim 27, wherein monitoring the temperature of the pre-mixed liquid comprises reading a temperature measuring device located inside of the container.

* * * * *

UNITED STATES PATENT AND TRADEMARK OFFICE
CERTIFICATE OF CORRECTION

PATENT NO. : 11,471,401 B2
APPLICATION NO. : 17/535493
DATED : October 18, 2022
INVENTOR(S) : Lilit Garibyan et al.

It is certified that error appears in the above-identified patent and that said Letters Patent is hereby corrected as shown below:

On the Title Page

Under the Related U.S. Application Data header, item (60) is replaced with the following paragraph:
(60) Provisional application No. 62/635,918, filed on Feb. 27, 2018, provisional application No. 62/121,472, filed on Feb. 26, 2015, provisional application No. 62/121,329, filed on Feb. 26, 2015, provisional application No. 62/042,979, filed on Aug. 28, 2014.

In the Specification

Starting at Column 1, Line 4, the paragraph titled "CROSS-REFERENCES TO RELATED APPLICATIONS" is replaced with the following paragraph:
CROSS-REFERENCES TO RELATED APPLICATIONS
The present application is a continuation of and claims priority to U.S. Patent Application Ser. No. 16/288,073, filed February 27, 2019, which is a continuation-in-part of U.S. Patent Application Ser. No. 15/505,042, which is a U.S. National Phase of PCT/US2015/047301, filed on August 27, 2015, which claims priority to U.S. Provisional Patent Application Ser. No. 62/042,979, filed Aug. 28, 2014, U.S. Provisional Patent Application Ser. No. 62/121,329, filed Feb. 26, 2015, and U.S. Provisional Patent Application Ser. No. 62/121,472, filed Feb. 26, 2015. U.S. Patent Application Ser. No. 16/288,073, filed February 27, 2019 also claims priority to U.S. Provisional Patent Application Ser. No. 62/635,918, filed February 27, 2018. The present application also claims priority to U.S. Patent Application Ser. No. 17/188,359, which is a continuation of U.S. Patent Application Ser. No. 15/505,042, which is a U.S. National Phase of PCT/US2015/047301, filed on August 27, 2015, which claims priority to U.S. Provisional Patent Application Ser. No. 62/042,979, filed Aug. 28, 2014, U.S. Provisional Patent Application Ser. No. 62/121,329, filed Feb. 26, 2015, and U.S. Provisional Patent Application Ser. No. 62/121,472, filed Feb. 26, 2015. The present application also claims priority to U.S. Patent Application Ser. No. 17/236,567, which is a continuation of U.S. Patent Application Ser. No. 15/505,039, which is a U.S. National Phase of PCT/US2015/047292, filed on Aug. 27, 2015, which claims priority to U.S. Provisional Patent Application Ser. No. 62/042,979, filed Aug. 28, Signed and Sealed this
Fourth Day of March, 2025

Coke Morgan Stewart
*Acting Director of the United States Patent and Trademark Office*

2014, U.S. Provisional Patent Application Ser. No. 62/121,329, filed Feb. 26, 2015, and U.S. Provisional Patent Application Ser. No. 62/121,472, filed Feb. 26, 2015. The entire disclosures of the aforementioned applications are incorporated herein by reference.